US012488900B2

(12) United States Patent

Baronov et al.

(10) Patent No.: US 12,488,900 B2

(45) **Date of Patent: *Dec. 2, 2025**

(54) SYSTEMS AND METHODS FOR TRANSITIONING PATIENT CARE FROM SIGNAL-BASED MONITORING TO RISK-BASED MONITORING

(71) Applicant: Etiometry Inc., Boston, MA (US)

(72) Inventors: Dimitar V. Baronov, Weston, MA (US); Evan J. Butler, New Haven, CT (US); Jesse M. Lock, Winchester, MA (US); Michael F. McManus, Pembroke, MA (US)

(73) Assignee: Etiometry Inc., Boston, MA (US)

( * ) Notice: Subject to any disclaimer, the term of this patent is extended or adjusted under 35 U.S.C. 154(b) by 142 days.

This patent is subject to a terminal disclaimer.

(21) Appl. No.: 18/206,752

(22) Filed: Jun. 7, 2023

(65) Prior Publication Data

US 2023/0317296 A1 Oct. 5, 2023

Related U.S. Application Data

(63) Continuation of application No. 17/033,591, filed on Sep. 25, 2020, now Pat. No. 11,676,730, which is a (Continued)

(51) Int. Cl.

| | |
|---|---|
| ***G16H 50/30*** | (2018.01) |
| ***G16H 50/20*** | (2018.01) |
| ***G16H 50/50*** | (2018.01) |

(52) U.S. Cl.

CPC ............. *G16H 50/30* (2018.01); *G16H 50/20* (2018.01); *G16H 50/50* (2018.01)

(58) Field of Classification Search

None

See application file for complete search history.

(56) References Cited

U.S. PATENT DOCUMENTS

| | | | |
|---|---|---|---|
| 5,595,181 | A | 1/1997 | Hubbard |
| 6,067,466 | A | 5/2000 | Selker et al. |

(Continued)

FOREIGN PATENT DOCUMENTS

| | | | |
|---|---|---|---|
| EP | 765134 | B1 | 7/2007 |
| EP | 3499513 | A1 | 6/2019 |

(Continued)

OTHER PUBLICATIONS

Barnea et al., Balancing the Circulation: Theoretic Optimization of Pulmonary/Systemic Flow Ratio in Hypoplastic Left Heart Syndrome, JACC vol. 24, No. 5, Nov. 1, 1994, pp. 1376-1381. (Year: 1994), 6 pages.

(Continued)

*Primary Examiner* — Jonathan Ng

(74) *Attorney, Agent, or Firm* — Nutter McClennen & Fish LLP

(57) ABSTRACT

A risk-based patient monitoring system for critical care patients combines data from multiple sources to assess the current and the future risks to the patient, thereby enabling providers to review a current patient risk profile and to continuously track a clinical trajectory. A physiology observer module in the system utilizes multiple measurements to estimate Probability Density Functions (PDF) of a number of Internal State Variables (ISVs) that describe components of the physiology relevant to the patient treatment and condition. A clinical trajectory interpreter module in the system utilizes the estimated PDFs of ISVs to identify under which probable patient states the patient can be currently categorized and assign a probability value that the patient will be in each of the identified states. The combination of patient states and their probabilities is defined as the clinical risk to the patient.

18 Claims, 58 Drawing Sheets

Related U.S. Application Data continuation-in-part of application No. 16/113,486, filed on Aug. 27, 2018, now Pat. No. 10,796,804, which is a continuation of application No. 14/727,696, filed on Jun. 1, 2015, now Pat. No. 10,062,456, which is a continuation of application No. 13/826,441, filed on Mar. 14, 2013, now abandoned, which is a continuation-in-part of application No. 13/689,029, filed on Nov. 29, 2012, now abandoned, and a continuation-in-part of application No. 13/328,411, filed on Dec. 16, 2011, now abandoned.

(60) Provisional application No. 62/906,518, filed on Sep. 26, 2019, provisional application No. 61/774,274, filed on Mar. 7, 2013, provisional application No. 61/727,820, filed on Nov. 19, 2012, provisional application No. 61/699,492, filed on Sep. 11, 2012, provisional application No. 61/684,241, filed on Aug. 17, 2012, provisional application No. 61/620,144, filed on Apr. 4, 2012, provisional application No. 61/614,846, filed on Mar. 23, 2012, provisional application No. 61/614,861, filed on Mar. 23, 2012.

(56) References Cited

U.S. PATENT DOCUMENTS 7,149,756 B1 12/2006 Schmitt et al.
7,590,550 B2 9/2009 Schoenberg
10,062,456 B2 8/2018 Baronov et al.
10,490,309 B1 11/2019 McNair
11,972,872 B1* 4/2024 McNair .................. G16H 20/00
2002/0035315 A1 3/2002 Ali et al.
2002/0077863 A1 6/2002 Rutledge et al.
2002/0099686 A1 7/2002 Schwartz et al.
2003/0050568 A1 3/2003 Green et al.
2003/0065535 A1* 4/2003 Karlov .................. G16H 50/20 705/2
2003/0233250 A1 12/2003 Joffe et al.
2004/0064357 A1 4/2004 Hunter et al.
2004/0078232 A1 4/2004 Troiani
2004/0097460 A1 5/2004 Ivey et al.
2004/0158132 A1 8/2004 Zaleski
2004/0199332 A1 10/2004 Tiff
2004/0230105 A1 11/2004 Geva et al.
2005/0010444 A1 1/2005 Iliff
2005/0240444 A1 10/2005 Wooten et al.
2006/0064396 A1 3/2006 Wei et al.
2006/0167722 A1 7/2006 Mrf Struys et al.
2006/0265249 A1 11/2006 Follis et al.
2006/0289020 A1 12/2006 Tabak et al.
2007/0010723 A1 1/2007 Jutela et al.
2007/0031902 A1 2/2007 Pestano et al.
2007/0055552 A1 3/2007 St. Clair et al.
2007/0185391 A1 8/2007 Morgan
2007/0239043 A1 10/2007 Patel et al.
2007/0239409 A1 10/2007 Alan
2007/0260285 A1 11/2007 Libbus et al.
2008/0147763 A1 6/2008 Levin
2008/0172214 A1 7/2008 Col et al.
2008/0208631 A1 8/2008 Morita et al.
2008/0228531 A1 9/2008 Kenedy et al.
2008/0235057 A1 9/2008 Weidenhaupt et al.
2008/0300449 A1 12/2008 Gerber et al.
2009/0125333 A1 5/2009 Heywood et al.
2009/0300417 A1 12/2009 Bonissone et al.
2010/0057490 A1 3/2010 Kocis et al.
2010/0070300 A1 3/2010 Anderson et al.
2010/0198101 A1 8/2010 Song et al.
2010/0205138 A1 8/2010 Zhang et al.
2010/0324437 A1* 12/2010 Freeman ................ A61B 5/085 600/529
2011/0004071 A1 1/2011 Faiola et al.
2011/0010197 A1 1/2011 Schoenberg
2011/0112380 A1 5/2011 Robinson
2011/0119212 A1 5/2011 De Bruin et al.
2011/0125046 A1 5/2011 Burton et al.
2011/0276342 A1 11/2011 Kazmierczak
2011/0306845 A1 12/2011 Osorio
2012/0022336 A1 1/2012 Teixeira
2012/0123232 A1 5/2012 Najarian et al.
2012/0130743 A1 5/2012 Gotthardt et al.
2013/0054264 A1 2/2013 Baronov et al.
2013/0185096 A1 7/2013 Giusti et al.
2013/0231949 A1 9/2013 Baronov et al.
2013/0253348 A1 9/2013 Tremper
2013/0261472 A1* 10/2013 Parkin .................... G16H 40/63 600/526
2013/0317378 A1 11/2013 Krivitski et al.
2014/0046683 A1* 2/2014 Michelson ............. G16H 40/20 705/2
2014/0352697 A1 12/2014 Lee et al.
2015/0006088 A1 1/2015 Eshelman et al.
2015/0347704 A1 12/2015 Baronov et al.
2017/0281020 A1* 10/2017 Mulligan ........... A61B 5/02042
2017/0281051 A1 10/2017 Evans et al.
2018/0169335 A1 6/2018 Baronov et al.
2018/0344919 A1 12/2018 Jones et al.
2021/0090742 A1 3/2021 Baronov et al.
2021/0104328 A1 4/2021 Baronov et al.
2021/0142915 A1* 5/2021 Haber .................... G16H 50/30
2021/0272696 A1* 9/2021 DeMazumder ........ G16H 15/00
2022/0293279 A1 9/2022 Baronov et al.
2022/0310266 A1 9/2022 Baronov et al.

FOREIGN PATENT DOCUMENTS

JP 2013536971 A 9/2013
RU 2345705 C2 2/2009
RU 2442531 C2 2/2012
WO 1999/09887 A1 3/1999
WO 2008036212 A2 3/2008
WO 2009103156 A1 8/2009
WO 2011/156587 A2 12/2011
WO 2012033771 A2 3/2012

OTHER PUBLICATIONS

Checchia et al., The Cardiac Intensive Care Unit Perspective on Hemodynamic Monitoring of Oxygen Transport Balance, Pediat. Crit. Care Med. 2011, vol. 12, No. 14 (Suppl), pp. S69-S71.

European Patent Office, Communication pursuant to Article 94(3) EPC in European Patent Application No. 13764131.2, 14 pages, dated Sep. 29, 2016.

European Patent Office, Supplemental European Search Report-Application No. EP 13764131, 10 pages, dated Oct. 21, 2015.

European Search Report for Application No. 20187516.8 issued Nov. 26, 2020 (9 pages).

Ghanayem et al., Home Monitoring of Infants After Stage One Palliation for Hypoplastic Left Heart Syndrome, Pediatric Cardiac Surgery Annual of the Seminars in Thoracic and Cardiovascular Surgery, vol. 7, 2004: pp. 32-38 (Year: 2004).

Harle et al., Information Visualization for Chronic Disease Risk Assessment, AI & Health, IEEE Computer Society, Nov./Dec. 2012, 5 pages.

International Searching Authority; Authorized Officer: M. Smirnov, International Search Report-International Application No. PCT/US2013/031512, dated Jul. 11, 2013, together with the Written Opinion of the International Searching Authority, 6 pages.

International Searching Authority; International Search Report-International Application No. PCT/ US2020/052903, dated Dec. 23, 2020, together with the Written Opinion of the International Searching Authority, 19 pages.

Japanese Patent Office, Japanese Office Action for Japanese Patent Application No. 2015-503307, 6 pages, dated Feb. 2017.

Leach et al., The pulmonary physician in critical care c 2: Oxygen delivery and consumption in the critically ill, Thorax 2002; 57:170-177 (Year: 2002).

(56) References Cited

OTHER PUBLICATIONS

Li et al., Profiles of hemodynamics and oxygen transport derived by using continuous measured oxygen consumption after the Norwood, procedure, The Journal of Thoracic and Cardiovascular Surgery—vol. 133, No. 2 (2007) (Year: 2007).

McMahon et al., "Comparison of non-invasive and invasive blood pressure in aeromedical care," Anaesthesia 2012, 67, pp. 1343-1347.

Moons et al., Limitations of Sensitivity, Specificity, Likelihood Ratio, and Bayes' Theorem in Assessing Diagnostic Probabilities: A Clinic Example, Epidemiology, vol. 8, No. 1, dated Jan. 1997, pp. 12-17.

Moss et al., Heart disease in infants, children, and adolescents: including the fetus and young adult, seventh edition, vol. 2, 2008, 37 pages (Year: 2008).

Mussatto, Kathleen, Management of infants with hypoplastic left heart syndrome integrating research in Nursing practice, Critical Care Nurse, Jan. 2005, 17 pages (Year: 2005).

Parati et al., "Comparison of Finger and Intra-arterial Blood Pressure Monitoring at Rest and During Laboratory Testing," Jun. 1989, Hypertension, vol. 13, No. 6, Part 1, pp. 647-655.

Rose, Cedric "A Dynamic Bayesian Network for Handling Uncertainty in a Decision Support System Adapted to the Monitoring of Patients Treated by Hemodialysis," Proceedings fo the 17th IEEE International Conference on Tools with Artificial Intelligence, 2005.

United States Patent and Trademark Office—Non-Final Office Action, U.S. Appl. No. 14/535,149, filed Nov. 6, 2014, dated Jul. 28, 2017, 28 pages.

United States Patent and Trademark Office, Final Office Action, dated Nov. 12, 2014, pertaining to U.S. Appl. No. 13/826,441, 9 pages.

United States Patent and Trademark Office, Non-final Office Action dated Dec. 27, 2013, pertaining to U.S. Appl. No. 13/826,441, 59 pages.

United States Patent and Trademark Office, Non-Final Office Action, dated Apr. 10, 2014, pertaining to U.S. Appl. No. 13/328,411, 27 pages.

United States Patent and Trademark Office, Non-Final Office Action, dated Jul. 14, 2014, pertaining to U.S. Appl. No. 13/826,441, 16 pages.

United States Patent and Trademark Office, Non-Final Office Action, dated Jun. 6, 2014, pertaining to U.S. Appl. No. 13/689,029, 25 pages.

United States Patent and Trademark Office, Notice of Allowance and Fees Due, dated May 12, 2014, pertaining to U.S. Appl. No. 13/826,441, 45 pages.

United States Patent and Trademark Office: Before the Patent Trial and Appeal Board (PTAB), Examiner's Decision on Appeal- Affirmed, dated Oct. 20, 2017, pertaining to U.S. Appl. No. 13/826,441, 12 pages.

* cited by examiner

HLHS Dynamics Model $$DO_{2_k} = DO_{2_{k-1}} + c_{DO_2}\left(\overline{DO_2} - DO_{2_{k-1}}\right) + w_{k_{DO_2}} \qquad w_{k_{DO_2}} \sim N(0, Q_{DO_2}) \qquad (1)$$

$$VO_{2_k} = VO_{2_{k-1}} + c_{VO_2}\left(\overline{VO_2} - VO_{2_{k-1}}\right) + w_{k_{VO_2}} \qquad w_{k_\beta} \sim N(0, Q_\beta) \qquad (2)$$

$$PVR_k = PVR_{k-1} + \Delta PVR_{k-1} + w_{k_{PVR}} \qquad w_{k_{PVR}} \sim N(0, Q_{PVR}) \qquad (3)$$

$$SVR_k = SVR_{k-1} + \Delta SVR_{k-1} + w_{k_{SVR}} \qquad w_{k_{SVR}} \sim N(0, Q_{SVR}) \qquad (4)$$

$$\Delta PVR_k = \Delta PVR_{k-1} + w_{k_{\Delta PVR}} \qquad w_{k_{\Delta PVR}} \sim N(0, Q_{\Delta PVR}) \qquad (5)$$

$$\Delta SVR_k = \Delta SVR_{k-1} + w_{k_{\Delta SVR}} \qquad w_{k_{\Delta SVR}} \sim N(0, Q_{\Delta SVR}) \qquad (6)$$

$$Hb_k = Hb_{k-1} + c_{Hb}\left(\overline{Hb} - Hb_{k-1}\right) + w_{k_{Hb}} \qquad w_{k_{Hb}} \sim N(0, Q_{Hb}) \qquad (7)$$

$$HR_k = HR_{k-1} + w_{k_{HR}} \qquad w_{k_{HR}} \sim N(0, Q_{HR}) \qquad (8)$$

$$SpvO_{2_k} = 100 - w_{k_{SpvO_2}} \qquad w_{k_{SpvO_2}} \sim \exp(\lambda) \qquad (9)$$

$$\eta_k \sim N(0, \Sigma_\eta) \qquad (10)$$

$$CVP_k \sim gamma(A_{CVP}, B_{CVP}) \qquad (11)$$

*Fig. 33*

HLHS Derived Variables $$SaO_2 = \frac{DO_{2_k} SVR_k SpvO_{2_k}}{VO_{2_k} PVR_k + DO_{2_k} SVR_k} \tag{12}$$

$$SvO_{2_k} = \left(1 - \frac{VO_{2_k}}{DO_{2_k}}\right) \frac{SVR_k SpvO_{2_k}}{VO_{2_k} PVR_k + DO_{2_k} SVR_k} \tag{13}$$

$$\Delta P_k = \frac{VO_{2_k} PVR_k + DO_{2_k} SVR_k}{HR_k SVR_k \left(-c_3 (VO_{2_k} PVR_k + DO_{2_k} SVR_k - c_5 SpvO_{2_k} Hb_k (c_3 CVP_k + c_4 + \eta_k)\right)} \tag{14}$$

$$ABPm_k = \frac{VO_{2_k} PVR_k + DO_{2_k} SVR_k}{c_5 SpvO_{2_k} Hb_k} + CVP_k \tag{15}$$

$$CO_k = \frac{VO_{2_k} PVR_k + DO_{2_k} SVR_k}{c_5 SpvO_{2_k} Hb_k} \left(\frac{1}{SVR_k} + \frac{1}{PVR_k}\right) \tag{16}$$

$$Q_p : Q_{s_k} = \frac{SVR_k}{PVR_k} \tag{17}$$

$$\Delta Q_p : Q_{s_k} = \frac{SVR_k}{PVR_k} \left(\frac{\Delta SVR_k}{\Delta t} - \frac{\Delta PVR_k}{\Delta t}\right) \tag{18}$$

*Fig. 34*

HLHS Observation Model $$\widetilde{SaO}_{2_k} = SaO_2 + n_{k_{SaO_2}} \qquad n_{k_{SaO_2}} \sim N(0, R_{SaO_2}) \tag{19}$$

$$\widetilde{SvO}_{2_k} = SvO_{2_k} + n_{k_{SvO_2}} \qquad n_{k_{SvO_2}} \sim N(0, R_{SvO_2}) \tag{20}$$

$$\widetilde{\Delta P}_k = \Delta P_k + n_{k_{\Delta P}} \qquad n_{k_{\Delta P}} \sim N(0, R_{\Delta P}) \tag{21}$$

$$\widetilde{ABPm}_k = ABPm_k + n_{k_{ABPm}} \qquad n_{k_{ABPm}} \sim N(0, R_{ABPm}) \tag{22}$$

$$\widetilde{HR}_k = HR_k + n_{k_{HR}} \qquad n_{k_{HR}} \sim N(0, R_{HR}) \tag{23}$$

$$\widetilde{CVP}_k = CVP_k + n_{k_{CVP}} \qquad n_{k_{CVP}} \sim N(0, R_{CVP}) \tag{24}$$

$$\widetilde{Hb}_k = Hb_k + n_{k_{Hb}} \qquad n_{k_{Hb}} \sim N(0, R_{Hb}) \tag{25}$$

Fig. 35A $$P(ISVs(t_{k+1}) \mid M(t_{k+1})) = N(\widetilde{ISVs}(t_{k+1} \mid t_{k+1}), \Sigma(t_{k+1} \mid t_{k+1}))$$

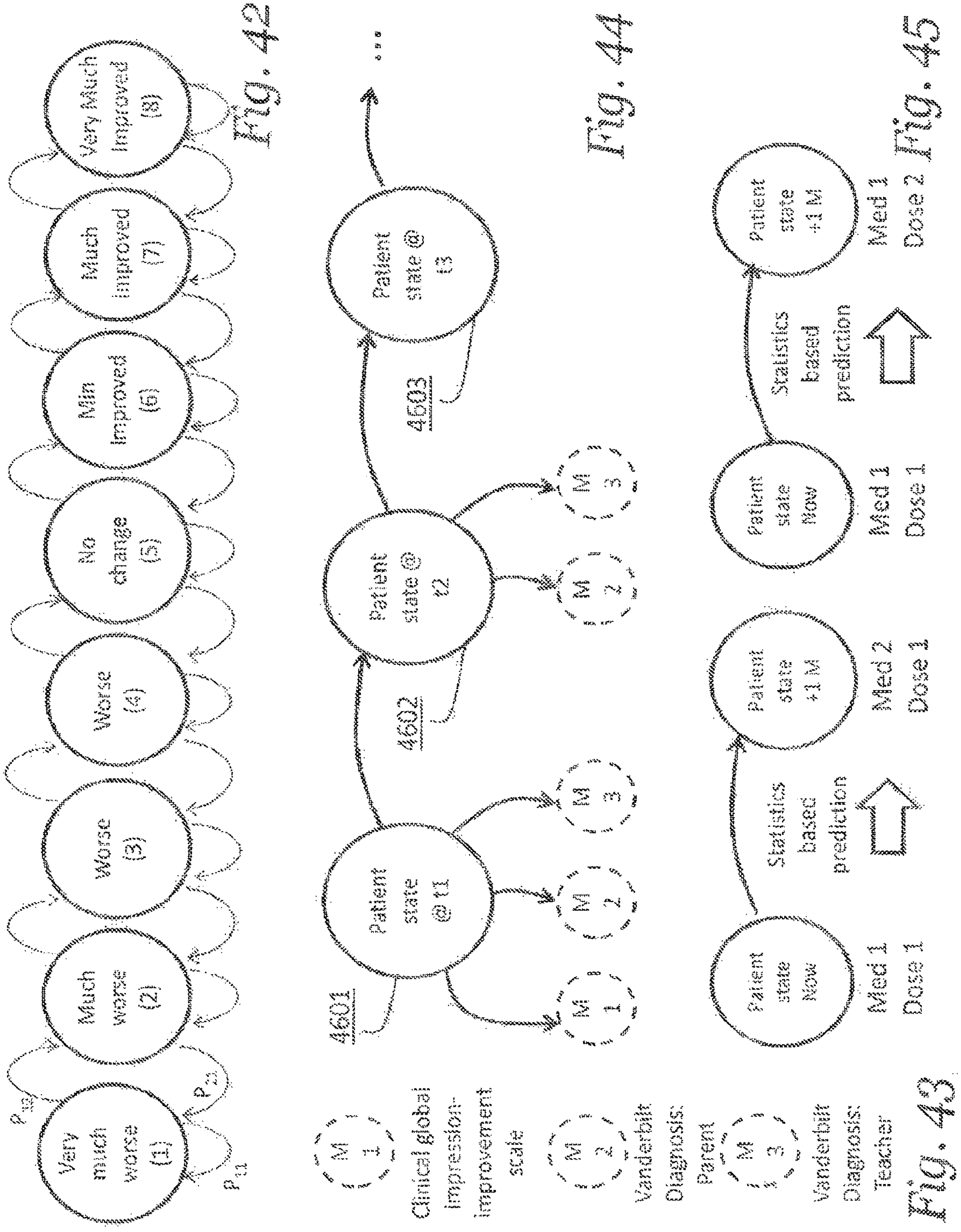
Very much worse (1)
Much worse (2)
Worse (3)
Worse (4)
No change (5)
Min improved (6)
Much improved (7)
Very Much improved (8)
P11
P12
P21
Fig. 42
M 1 Clinical global impression-improvement scale
M 2 Vanderbilt Diagnosis: Parent
M 3 Vanderbilt Diagnosis: Teacher
Fig. 43
4601
Patient state @ t1
4602
Patient state @ t2
4603
Patient state @ t3
Fig. 44
Patient state Now
Med 1 Dose 1
Statistics based prediction
Patient state +1 M
Med 2 Dose 1
Patient state Now
Med 1 Dose 1
Statistics based prediction
Patient state +1 M
Med 1 Dose 2
Fig. 45

SYSTEMS AND METHODS FOR TRANSITIONING PATIENT CARE FROM SIGNAL-BASED MONITORING TO RISK-BASED MONITORING

PRIORITY CLAIM

This application is a continuation of U.S. application Ser. No. 17/033,591, filed Sep. 25, 2020, titled "System and Methods for Transitioning Patient Care from Signal Based Monitoring to Risk Based Monitoring,", which claims priority to U.S. provisional application Ser. No. 62/906,518 filed Sep. 26, 2019 and entitled "Systems and Methods for Transitioning Patient Care from Signal-Based Monitoring to Risk-Based Monitoring". U.S. application Ser. No. 17/033,591 is a continuation-in-part of U.S. non-provisional patent application Ser. No. 16/113,486 filed Aug. 27, 2018 and entitled "Systems and Methods for Transitioning Patient Care from Signal-Based Monitoring to Risk-Based Monitoring,", which is a continuation of U.S. non-provisional patent application Ser. No. 14/727,696, filed Jun. 1, 2015 and entitled "Systems and Methods for Transitioning Patient Care from Signal-Based Monitoring to Risk-Based Monitoring," issued Aug. 28, 2018 as U.S. Pat. No. 10,062,456, which is a continuation of U.S. non-provisional patent application Ser. No. 13/826,441, filed Mar. 14, 2013 and entitled "Systems and Methods for Transitioning Patient Care from Signal-Based Monitoring to Risk-Based Monitoring, which is a Continuation-In-Part of the following non-provisional patent applications:

U.S. patent application Ser. No. 13/689,029, filed on Nov. 29, 2012, entitled SYSTEMS AND METHODS FOR OPTIMIZING MEDICAL CARE THROUGH DATA MONITORING AND FEEDBACK TREATMENT; and U.S. application Ser. No. 13/328,411, filed on Dec. 16, 2011, entitled METHOD AND APPARATUS FOR VISUALIZING THE RESPONSE OF A COMPLEX SYSTEM TO CHANGES IN A PLURALITY OF INPUTS;

and also claims priority to the following provisional patent applications:

U.S. Provisional Application No. 61/727,820, filed on Nov. 19, 2012, entitled USER INTERFACE DESIGN FOR RAHM;

U.S. Provisional Application No. 61/699,492, filed on Sep. 11, 2012, entitled SYSTEMS AND METHODS FOR EVALUATING CLINICAL TRAJECTORIES AND TREATMENT STRATEGIES FOR OUTPATIENT CARE;

U.S. Provisional Application No. 61/684,241, filed on Aug. 17, 2012, entitled SYSTEM AND METHODS FOR PROVIDING RISK ASSESSMENT IN ASSISTING CLINICIANS WITH EFFICIENT AND EFFECTIVE BLOOD MANAGEMENT;

U.S. Provisional Application No. 61/620,144, filed on Apr. 4, 2012, entitled SYSTEMS AND METHODS FOR PROVIDING MOBILE ADVANCED CARDIAC SUPPORT;

U.S. Provisional Application No. 61/614,861, filed on Mar. 23, 2012 entitled SYSTEMS AND METHODS FOR REDUCING MORBIDITY AND MORTALITY WHILE REDUCING LENGTH OF STAY IN A HOSPITAL SETTING;

U.S. Provisional Application No. 61/614,846, filed Mar. 23, 2012, entitled SYSTEMS AND METHODS FOR PROVIDING MOBILE ADVANCED CARDIAC SUPPORT; and U.S. Provisional Application No. 61/774,274, filed on Mar. 7, 2013, entitled SYSTEMS AND METHODS FOR TRANSITIONING PATIENT CARE FROM SIGNAL-BASED MONITORING TO RISK-BASED MONITORING.

The entire subject matter of each of the foregoing applications being incorporated herein by this reference for all purposes.

STATEMENT REGARDING FEDERALLY SPONSORED RESEARCH OR DEVELOPMENT

This invention was made with government support under R43HL117340 awarded by the National Heart, Lung, And Blood Institute of the National Institutes of Health. The government has certain rights in the invention.

BACKGROUND ART

The present disclosure relates to systems and methods for risk-based patient monitoring. More particularly, the present disclosure relates to systems and methods for assessing the current and future risks of a patient by combining data of the patient from various different sources.

Practicing medicine is becoming increasingly more complicated due to the introduction of new sensors and treatments. As a result, clinicians are confronted with an avalanche of patient data, which needs to be evaluated and well understood in order to prescribe the optimal treatment from the multitude of available options, while reducing patient risks. One environment where this avalanche of information has become increasingly problematic is the Intensive Care Unit (ICU). There, the experience of the attending physician and the physician's ability to assimilate the available physiologic information have a strong impact on the clinical outcome. It has been determined that hospitals which do not maintain trained intensivists around the clock experience a 14.4% mortality rate as opposed to a 6.0% rate for fully staffed centers. It is estimated that raising the level of care to that of average trained physicians across all ICUs can save 160,000 lives and $4.3 Bn annually. As of 2012, there is a shortage of intensivists, and projections estimate the shortage will only worsen, reaching a level of 35% by 2020.

The value of experience in critical care can be explained by the fact that clinical data in the ICU is delivered at a rate far greater than even the most talented physician can absorb, and studies have shown that errors are six times more likely under conditions of information overload and eleven time more likely with an acute time shortage. Moreover, treatment decisions in the ICU heavily rely on clinical signs that are not directly measurable, but are inferred from other physiologic information. Thus clinician expertise and background play a more significant role in the minute to minute decision making process. Not surprisingly, this leads to a large variance in hidden parameter estimation. As an example, although numerous proxies for cardiac output are continuously monitored in critical care, studies have demonstrated poor correlation between subjective assessment by clinicians, and objective measurement by thermodilution. Experienced intensivists incorporate this inherent uncertainty in their decision process by effectively conducting risk management, i.e. prescribing the treatment not only based on the most probable patient state, but also weighing in the risks of the patient being in other more adverse states. From this perspective, experienced intensivists confront the data overload in intensive care by converting the numerous heterogeneous signals from patient observations into a risk assessment.

Therefore, there is a clear need for a decision support system in the ICU that achieves a paradigm shift from signal-based patient monitoring to risk based patient monitoring, and consequently helps physicians overcome the barrage of data in the ICU.

BRIEF SUMMARY

Disclosed herein is a risk-based patient monitoring system for critical care patients that combines data from any of bedside monitors, electronic medical records, and other patient specific information, to assess the current and the future risks to the patient. The system may be also embodied as a decision support system that prompts the user with specific actions according to a standardized medical plan, when patient specific risks pass a predefined threshold. Yet another embodiment of the described technologies is an outpatient monitoring system which combines patient and family evaluation, together with information about medication regiments and physician evaluations to produce a risk profile of the patient, continuously track its clinical trajectory, and provide decision support to clinicians regarding when to schedule a visit or additional tests.

According to one implementation, a risk-based monitoring application executing on a system processor comprises a data reception module, a physiology observer module, a clinical trajectory interpreter module, and a visualization and user interaction module. In an exemplary embodiment, the data reception module may be configured to receive data from bedside monitors, electronic medical records, treatment device, and any other information that may be deemed relevant to make informed assessment regarding the patient's clinical risks, and any combination thereof of the preceding elements.

The physiology observer module utilizes multiple measurements to estimate Probability Density Functions (PDF) of Internal State Variables (ISVs) that describe the components of the physiology relevant to the patient treatment and condition. The clinical trajectory interpreter module may be configured with multiple possible patient states, and determine which of those patient states are probable and with what probability, given the estimated probability density functions of the internal state variables.

In various embodiments, the clinical trajectory interpreter module determines the patient conditions under which a patient may be categorized and is capable of also determining the probable patient states under which the patient can be currently categorized, given the estimated probability density functions of the internal state variables. In this way, each of the possible patient states is assigned a probability value from 0 to 1. The combination of patient states and their probabilities is defined as the clinical risk to the patient.

The visualization and user interactions module takes i) time series of physiologic measurements acquired continuously or intermittently and patient specific identifiers such as condition, demographics, visual examinations from the data reception module; ii) time series of probability density functions of internal state variables estimated from the physiology observer module; and time series of the probabilities that the patient is at particular state and the hazard level of the respective risks from the clinical trajectory interpreter module. Then it visualizes this data on graphs which represent the dependence of the variables with time, by either directly plotting them on a screen, or in the case of probability density functions plotting them by encoding the likelihood at particular point of time and at particular value with a color scheme. The visualization and user interactions module may also visualize the current risks to the patient by representing them with boxes of different size and color, the size of the box corresponding to the probability of a patient state at particular point in time and the color of the box corresponding to its hazard level. Additionally, the visualization and user interactions module can allow the users to set alarms based on the patient state probabilities, share those alarms with other users, take notes related to the patient risks and share those notes with other users, and browse other elements of the patient medical history.

According to one aspect of the disclosure, a computer-implemented medium and method for risk based monitoring of patients comprises: A) acquiring, with a computer, data associated with a plurality of the internal state variables each describing a parameter physiologically relevant to one of a treatment and a condition of a patient; B) storing, in a computer accessible memory, the acquired data associated with the plurality of the internal state variables; C) generating, with a computer, estimated probability density functions for the plurality of the internal state variables; and D) identifying, with a computer, from the generated probability density functions of the internal state variables, into which of a plurality of possible patient states the patient is currently categorizable and generating a probability value associated with each identified possible patient state. In one embodiment, the probability value associated with the identified possible patient states is between 0 and 1. In another embodiment, the method further comprises: E) presenting on a screen the probability values and their associated respective identified possible patient states, wherein the combination of identified possible patient states and their associated respective probability values is defined as the clinical risk to the patient.

According to another aspect of the disclosure, a risk based monitoring system for monitoring patients comprises: a processor; a memory coupled to the processor; a data reception module, operably coupled to a plurality of sources of information relative to a patient, for acquiring data associated with a plurality of the internal state variables each describing a parameter physiologically relevant to one of a treatment and a condition of a patient; a physiology observer module, in communication with the data reception module, and configured to generate probability density functions of the internal state variables; a clinical trajectory interpreter module, in communication with the physiology observer module, and configured to identify into which of a plurality of possible patient states the patient is currently categorizable and to generate a probability value associated with each identified possible patient state. In one embodiment, the method further comprises: a user interaction module, in communication with the clinical trajectory interpreter and the data reception module and memory, for presenting the probability values and their associated respective identified possible patient states, wherein the combination of identified possible patient states and the associated respective probability values is defined as the clinical risk to the patient.

According to still other aspects of the disclosure, certain measurements, such as Hemoglobin, are available to the system with an unknown amount of time latency, meaning the measurements are valid in the past relative to the current time and the time they arrive over the data communication links. The physiology observer module may handle such out of sequence measurements using back propagation, in which the current estimates of the ISVs are projected back in time to the time of validity of the measurements, so that the information from the latent measurement can be incorporated correctly. Accordingly, in accordance with another aspect of the disclosure, a computer-implemented method for risk based monitoring of patients, comprises: A) acquiring, with a computer, data associated with a plurality of the internal state variables each describing a parameter physiologically relevant to one of a treatment and a condition of a patient, not all of the data associated with the plurality of the internal state variables with at the same periodicity; B) storing, in a computer accessible memory, the acquired data associated with the plurality of the internal state variables; C) generating, with a computer, estimated probability density functions for the plurality of the internal state variables; and D) identifying, with a computer, from the generated probability density functions of the internal state variables, into which of a first plurality of possible patient states $P(S_1)$, $P(S_2)$, $P(S_3)$, . . . , $P(S_n)$, the patient could has previously been categorizable and generating a probability value associated with each identified possible prior patient state. In one embodiment, generating estimated probability density functions comprises: C1) generating estimated probability density functions for the first plurality of the internal state variables at a current time step $t_k$; and C2) generating probability density functions for the plurality of the internal state variables at a another time step $t_{k-N}$, where N is an integer value greater than 1, by evolving backwards from the probability estimates at time step $t_k$ to the time step $t_{k-N}$ using a defined transition probability kernel.

BRIEF DESCRIPTION OF THE DRAWINGS

It should be understood at the outset that although illustrative implementations of one or more embodiments of the present disclosure are provided below, the disclosed systems and/or methods may be implemented using any number of techniques, whether currently known or in existence. The disclosure should in no way be limited to the illustrative implementations, drawings, and techniques illustrated below, including the exemplary designs and implementations illustrated and described herein, but may be modified within the scope of the appended claims along with their full scope of equivalents.

In the Drawings;

FIG. 33 illustrates conceptually several equations that may be used to model the dynamics of the HLHS stage 1 physiology in accordance with the disclosure;

FIG. 34 illustrates conceptually example equations that may be used to abstract the relationships between the dynamic variables in the model and the derived variables in accordance with the disclosure;

FIG. 35A schematically illustrates an embodiment of an observation model that may be used to relate the derived variables with the available sensor data in accordance with the disclosure;

FIG. 42 illustrates conceptually possible patient states that may describe the clinical trajectory of an ADHD patient in accordance with the disclosure;

FIG. 43 lists the available patient evaluation modalities as M1, M2, and M3;

FIG. 44 illustrates conceptually a dynamic model of the patient evolution from state to state abstracted by a Dynamic Bayesian Network in accordance with the disclosure;

FIG. 45 illustrates conceptually an alternative embodiment for two predictions of how the patient state can transition in a single month given medication change or a dosage change in accordance with the disclosure;

DETAILED DESCRIPTION OF SPECIFIC EMBODIMENTS

Figure 1A:
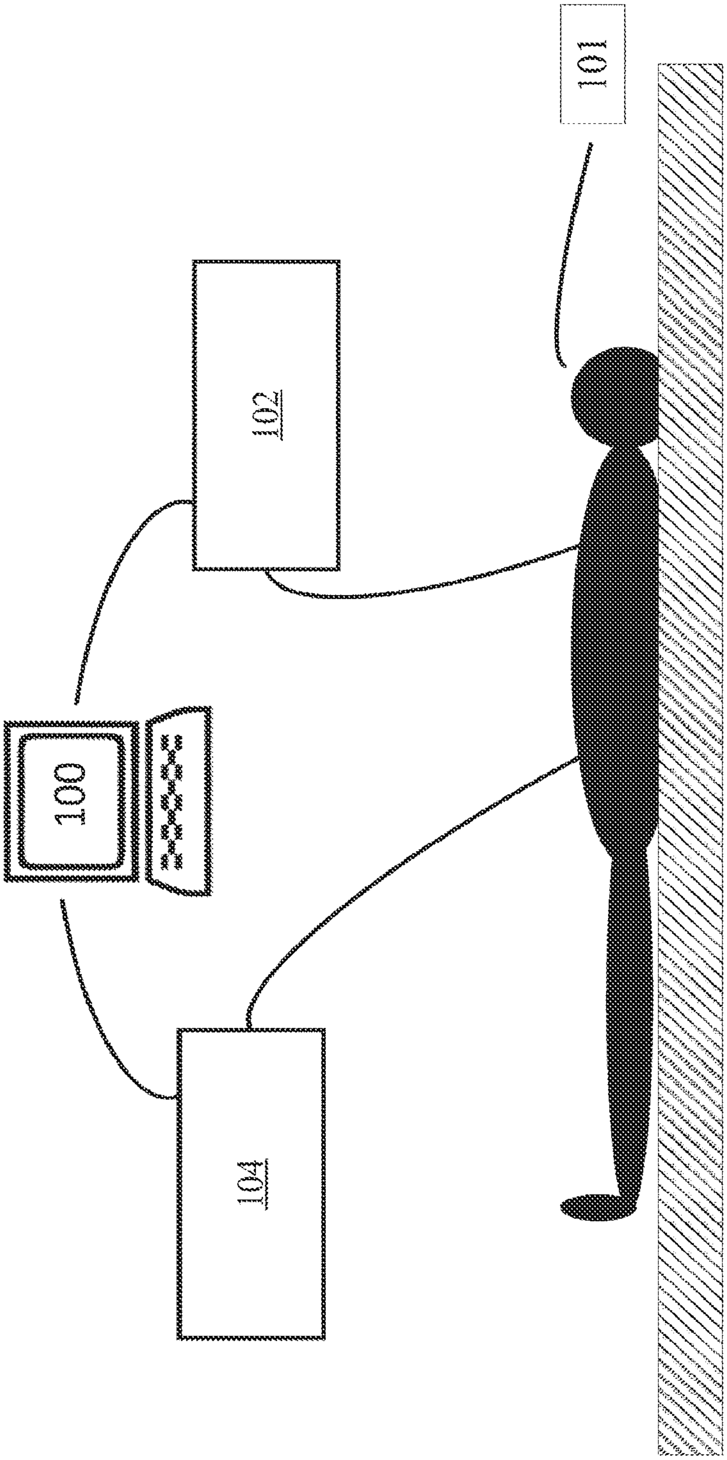
FIG. 1A and FIG. 1B schematically illustrate an embodiment of a medical care risk-based monitoring environment in accordance with the disclosure.

Technologies are provided herein for providing risk-based patient monitoring of individual patients to clinical personnel. The technologies described herein can be embodied as a monitoring system for critical care, which combines data from various bedside monitors, electronic medical records, and other patient specific information to assess the current and the future risks to the patient. The technologies can be also embodied as a decision support system that prompts the user with specific actions according to a standardized medical plan, when patient specific risks pass a predefined threshold. Yet another embodiment of the described technologies is an outpatient monitoring system which combines patient and family evaluation, together with information about medication regiments and physician evaluations to produce a risk profile of the patient, continuously track its clinical trajectory, and provide decision support to clinicians as regarding when to schedule a visit or additional tests.

Definitions

As used in this description and the accompanying claims, the following terms shall have the meanings indicated, unless the context otherwise requires.

A "set" includes at least one member.

The term "Internal State Variable" (or "ISV") means a parameter of a patient's physiology that is physiologically relevant to one of a treatment and a condition of a patient.

Examples of ISVs include, without limitation, ISVs may be directly observable with noise (as a non-limiting example, heart rate is a directly observable ISV), hidden (as a non-limiting example, oxygen delivery (DO2) defined as the flow of blood saturated oxygen through the aorta cannot be directly measured and is thus hidden), or measured intermittently (as a non-limiting example, hemoglobin concentration as measured from Complete Blood Count tests is an intermittently observable ISV). Other examples of ISVs include, without limitation, Pulmonary Vascular Resistance (PVR); Cardiac Output (CO); hemoglobin, and rate of hemoglobin production/loss.

The term "hidden," in reference to an Internal State Variable, means an ISV that is not directly measured by a sensor coupled to the patient. Some hidden ISVs cannot be directly measured by a sensor coupled to the patient. Some hidden ISVs require laboratory analysis of a sample (e.g., blood) taken from the patient.

The term "Patient State" means a qualitative description of the physiology at a particular point of time of the patient clinical course which is recognizable by medical practice, and may have implications to clinical decision-making. A patient state may be a medical condition, such as an adverse medical condition, for example.

Examples of particular patient states include, but are not limited to, adverse medical conditions such as inadequate delivery of oxygen, inadequate ventilation of carbon dioxide, hyperlactatemia, acidosis; amongst others. In addition, these patient states may be specific to a particular medical condition, and the bounds of each of the patient states may be defined by threshold values of various physiological variables and data.

The term "Clinical Risk" means the probability of a patient being in a particular patient state.

The term "Clinical Trajectory" means the sequence of patient states that a patient evolves through during a patient's clinical course.

System Modules And Interaction

Figure 1B:
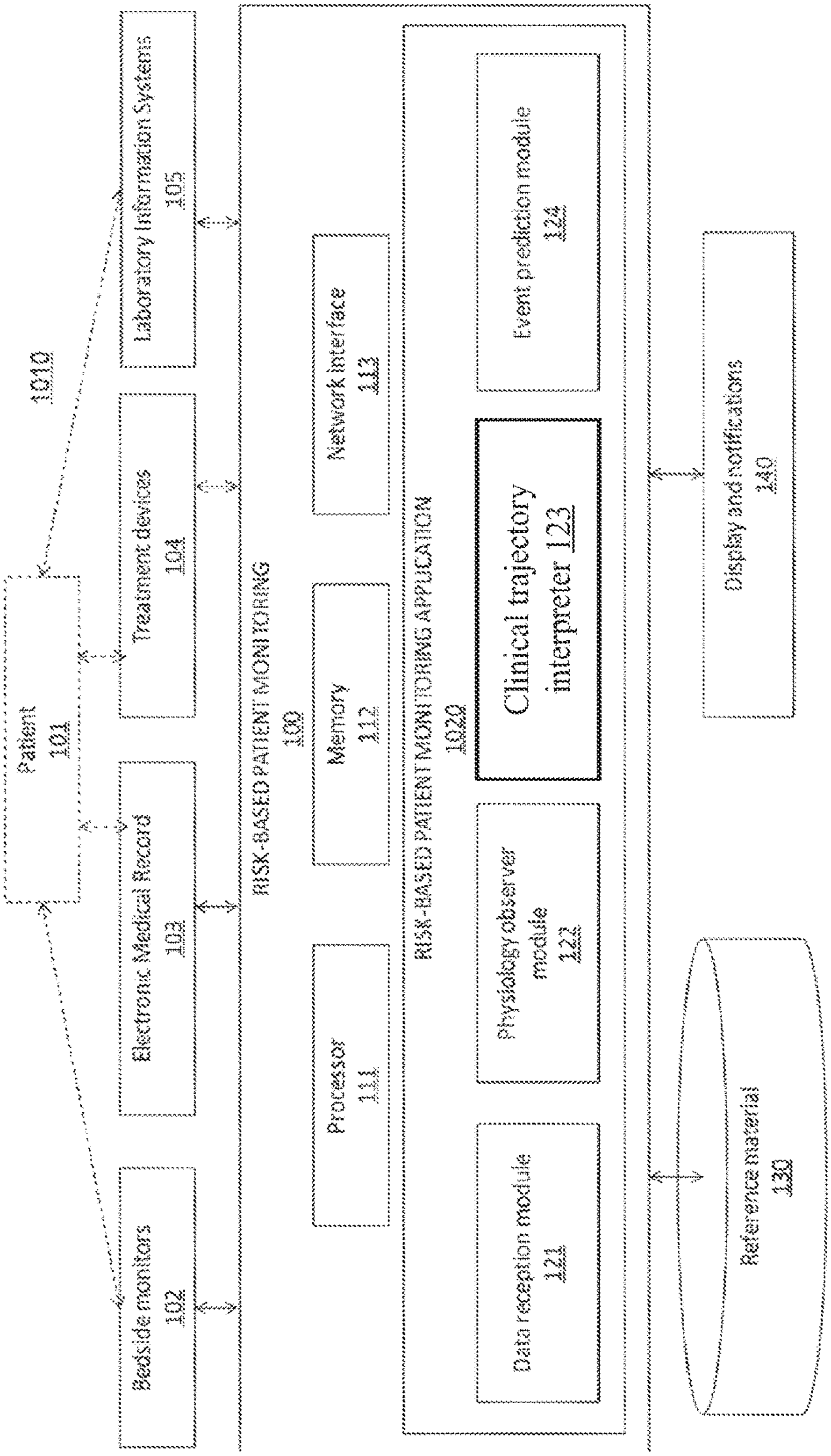

Referring now to the figures, FIG. 1A and FIG. 1B illustrate an embodiment of a medical care risk-based monitoring environment 1010 for providing health providers, such as physicians, nurses, or other medical care providers, risk-based monitoring in accordance with various embodiments of the present disclosure. A patient 101 may be coupled to one or more physiological sensors or bedside monitors 102 that may monitor various physiological parameters of the patient. It should be noted that a patient may be a human, or not human (a non-human being).

These physiological sensors may include but are not limited to, a blood oximeter, a blood pressure measurement device, a pulse measurement device, a glucose measuring device, one or more analyte measuring devices, an electrocardiogram recording device, amongst others. In addition, the patient may be administered routine exams and tests and the data stored in an electronic medical record (EMR) 103. The electronic medical record 103 may include but is not limited to stored information such as hemoglobin, arterial and venous oxygen content, lactic acid, weight, age, sex, ICD-9 code, capillary refill time, subjective clinician observations, patient self-evaluations, prescribed medications, medications regiments, genetics, etc. In addition, the patient 101 may be coupled to one or more treatment devices 104 that are configured to administer treatments to the patient. In some embodiments, one or more treatment devices 104 may be controlled by a system 100 as disclosed herein, for example in response to output defining a patient state or medical condition from a trajectory interpreter module. In various embodiments, the treatments devices 104 may include extracorporeal membrane oxygenator, ventilator, medication infusion pumps, etc.

By way of the present disclosure, the patient 101 may be afforded improved risk-based monitoring over existing methods. A patient specific risk-based monitoring system, generally referred to herein as system 100, may be configured to receive patient related information, including real-time information from bed-side monitors 102, EMR patient information from electronic medical record 103, information from treatment devices 104, such as settings, infusion rates, types of medications, and other patient related information, which may include the patient's medical history, previous treatment plans, results from previous and present lab work, allergy information, predispositions to various conditions, and any other information that may be deemed relevant to make an informed assessment of the possible patient conditions and states, and their associated probabilities. For the sake of simplicity, the various types of information listed above will generally be referred to hereinafter as "patient-specific information". In addition, the system may be configured to utilize the received information, determine the clinical risks, which then can be presented to a medical care provider, including but not limited to a physician, nurse, or other type of clinician.

The system, in various embodiments, includes one or more of the following: a processor 111, a memory 112 coupled to the processor 111, and a network interface 113 configured to enable the system to communicate with other devices over a network. In addition, the system may include a risk-based monitoring application 1020 that may include computer-executable instructions, which when executed by the processor 111, cause the system to be able to afford risk based monitoring of the patients, such as the patient 101.

The risk based monitoring application 1020 includes, for example, a data reception module 121, a physiology observer module 122, a clinical trajectory interpreter module 123 (or, in some embodiments, risk calculation engine 123), and a visualization and user interaction module 124. In an exemplary embodiment, the data reception module 121 may be configured to receive data from bedside monitors 102, electronic medical records 103, treatment devices 104, and any other information that may be deemed relevant to make an informed assessment regarding the patient's clinical risks, and any combination thereof of the preceding elements.

The physiology observer module 122 utilizes multiple measurements to estimate probability density functions (PDF) of internal state variables (ISVs) that describe the components of the physiology relevant to the patient treatment and condition in accordance with a predefined physiology model. The ISVs may be directly observable with noise (as a non-limiting example, heart rate is a directly observable ISV), hidden (as a non-limiting example, oxygen delivery ($DO_2$) defined as the flow of blood saturated oxygen through the aorta cannot be directly measured and is thus hidden), or measured intermittently (as a non-limiting example, hemoglobin concentration as measured from Complete Blood Count tests is an intermittently observable ISV). In some embodiments, when the physiology observer module 122 evaluates a set of ISVs at a given time step (e.g., $t_k$; $t_{k+1}$; generally $t_{k+n}$), the system 100 may not have a complete set of ISV measurements contemporaneous with that given time step. For example, the system 100 may have measurements for that given time step for some internal state variables, but may not have measurements for that given time step for some other internal state variables (e.g., a contemporaneous measurement for an intermittent ISV may not be available for the given time step). Consequently, that intermittent ISV is, for purposes of evaluating ISVs at the given time step, a hidden ISV. However, evaluation of the set of ISVs by the physiology observer module 122 (as described herein) is nevertheless possible according to embodiments described herein because the predicted PDFs of ISVs 211 carry in them the influence of past measurements of that intermittent ISV, and consequently those predicted PDFs of ISVs 211 are, in illustrative embodiments, sufficient input for the physiology observer module 122.

In one embodiment, instead of assuming that all variables can be estimated deterministically without error, the physiology observer module 122 of the present disclosure provides probability density functions as an output. Additional details related to the physiology observer module 122 are provided herein.

The clinical trajectory interpreter module 123 may be configured, for example, with multiple possible patient states, and may determine which of those patient states are probable and with what probability, given the estimated probability density functions of the internal state variables. Examples of particular patient states include, but are not limited to, hypotension with sinus tachycardia, hypoxia with myocardial depression, compensated circulatory shock, cardiac arrest, hemorrhage, amongst others. In addition, these patient states may be specific to a particular medical condition, and the bounds of each of the patient states may be defined by threshold values of various physiological variables and data. In various embodiments, the clinical trajectory interpreter module 123 may determine the patient conditions under which a patient may be categorized using any of information gathered from reference materials, information provided by health care providers, other sources of information. The reference materials may be stored in a database or other storage device 130 that is accessible to the risk based monitoring application 1020 via network interface 113, for example. These reference materials may include material synthesized from reference books, medical literature, surveys of experts, physician provided information, and any other material that may be used as a reference for providing medical care to patients. In some embodiments, the clinical trajectory interpreter module 123 may first identify a patient population that is similar to the subject patient being monitored. By doing so, the clinical trajectory interpreter module 123 may be able to use relevant historical data based on the identified patient population to help determine the possible patient states.

The clinical trajectory interpreter module 123 is capable of also determining the probable patient states under which the patient can be currently categorized, given the estimated probability density functions of the internal state variables, as provided by physiology observer module 122. In this way, each of the possible patient states is assigned a probability value from 0 to 1. The combination of patient states and their probabilities is defined as the clinical risk to the patient. Additional details related to the clinical trajectory interpreter module 123 are provided herein.

Visualization and user interactions module 124 may be equipped to take the outputs of the data reception module 121 the physiology observer module 122, and the clinical trajectory interpreter module 123 and present them to the clinical personnel. The visualization and user interactions module 124 may show the current patient risks, their evolution through time, the probability density functions of the internal state variables as functions of time, and other features that are calculated by the two modules 122 and 123 as by-products and are informative to medical practice. Additionally, visualization and user interactions module 124 enables the users to set alarms based on the patient state probabilities, share those alarms with other users, take notes related to the patient risks and share those notes with other users, and browse other elements of the patient medical history. Additional details related to the visualization and user interactions module 124 are provided herein.

I. Physiology Observer Module 122

Figure 2A:
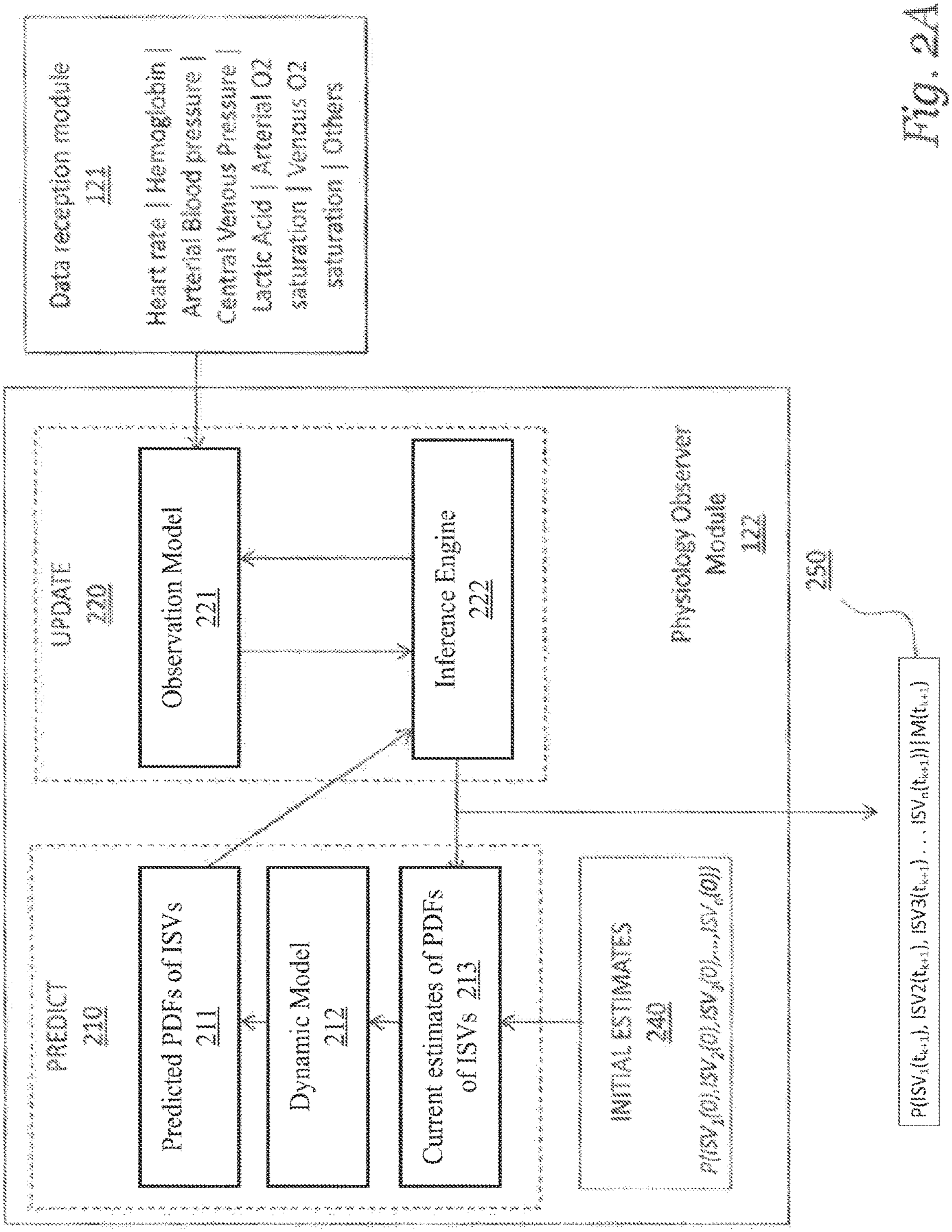
FIG. 2A illustrates conceptually a basic schematic of the physiology observer module in accordance with the disclosure.

FIG. 2A illustrates a basic schematic of the physiology observer module 122, which utilizes two models of the patient physiology: a dynamic model (or dynamic module) 212 and an observation model (or observation module) 221. The dynamic model 212 captures the relationship arising between the internal state variables at some time $t_k$ and another close, subsequent time $t_{k+1}$, thereby enabling modeling of the patient physiology as a system whose present state has information about the possible future evolutions of the system. Given the propensity of the patient physiology to remain at homeostasis through auto-regulation, and the physical laws guiding different processes in the human body, e.g. fluid mechanics, chemical reactions; there is a clear rational of introducing dynamic equations that capture the evolution of the system from a present state to a future state.

The observation model 221 may capture the relationships between measured physiology variables and other internal state variables. Examples of such models include: a) the dependence of the difference between systolic and diastolic arterial blood pressures (also called pulse pressure) on the stroke volume; b) the relationship between measured heart rate and actual heart rate; c) the relationship between pulse oximetry and arterial oxygen saturation; and d) any other dependence between measurable and therefore observable parameters and internal state variables.

The physiology observer module 122 functions as a recursive filter by employing information from previous measurements to generate predictions of the internal state variables and the likelihood of probable subsequent measurements (i.e., future measurements, relative to the previous measurements) and then comparing them with subsequent measurements (e.g., the most recently acquired measurements). Specifically the physiology observer module 122 utilizes the dynamic model 212 in the predict step or mode 210 and the observation model 221 in the update step or mode 220. In the following illustrative example, operation of the physiology observer module 122 over successive time steps is described using FIG. 2B and FIG. 2C. For purposes of illustration in those figures, the previous time step will be denoted $t_k$, the subsequent time step will be denoted $t_{k+1}$. It should be noted that the previous time step $t_k$, itself was preceded by an earlier time step $t_{k-1}$. Consequently, the time steps in this illustrative embodiment proceed from $t_{k-1}$ to $t_k$ to $t_{k+1}$.

A. Predict Module 210 {FIG. 2B}

During the prediction mode 210, at or after time step $t_k$ and on or before time step $t_{k+1}$, the physiology observer module 122 takes the estimated probability density functions (PDFs) of ISVs 213 at a time step $t_k$ (which were produced at time step $t_k$ based in part from data from earlier time step $t_{k-1}$, and which may be referred-to as the posterior probabilities for time step $t_k$) and feeds them to the dynamic model 212, which produces predictions of the probability density functions of the ISVs 211 for the next time step $t_{k+1}$. This is accomplished using the following equation:

$$P(\mathrm{ISVs}(t_{k+1})|M(t_k))=\int_{ISVs\in ISV}P(\mathrm{ISVs}(t_{k+1})|\mathrm{ISVs}(t_k))P(\mathrm{ISVs}(t_k)|M(t_k))d\mathrm{ISVs}$$

Where:

$$\mathrm{ISVs}(t_k)=\{\mathrm{ISV}_1(t_k),\mathrm{ISV}_2(t_k),\mathrm{ISV}_3(t_k),\ldots \mathrm{ISV}_n(t_k)\};$$

and $M(t_k)$ is the set of all measurements up to time $t_k$.

The probability $P(\mathrm{ISVs}(t_k+1)|\mathrm{ISVs}(t_k))$ defines a transition probability kernel describing the dynamic model 212, which defines how the estimated PDFs evolve with time.

The probabilities $P(\mathrm{ISVs}(t_k)|M(t_k))$ are provided by the inference engine 222 and are the posterior probabilities of the ISVs given the measurements acquired at the earlier time step $t_{k-1}$.

B. Update Module 220

During the update mode 220 of the physiology observer module 122, the predicted probability density functions of the ISVs 211 (i.e., which were produced using the predict module and the density function at the preceding time step $t_k$) are compared against the measurements received (at time $t_{k+1}$) from data reception module 121 with the help of the observation model 221, and as a result the ISVs are updated to reflect the new available information. Processes of the Observation Model 221 are described in more detail, below.

1. Observation Model {221}

The observation model 221 consequently produces a conditional likelihood kernel [for example: $[P(m_1(t_{k+1}), m_2(t_{k+1}), \ldots m_n(t_{k+1})|\mathrm{ISVs}(t_{k+1}))]$ and provides the conditional likelihood kernel 230 to the Inference Engine 222. The conditional likelihood kernel 230 provided by the observation model 221 determines how likely the currently received measurements are given the currently predicted ISVs. Criteria for determining how likely the currently received measurements are, given the currently predicted ISVs, may be established by the discretion of the system's designer, based on the particular application faced by the designer.

Note that the observation model 221 has two inputs and one output. The inputs are (1) the received measurements from data reception module 121, and (2) the predicted probability density functions of the ISVs 211 [e.g., P(ISVs (tk+1)|M(tk))], provided via the Inference Engine 222, represented by the arrow pointing from the Inference Engine 222 to the Observation Module 221. The output of the observation model 221 is the conditional likelihood kernel 230.

2. Operation of the Observation Model 221

The processes of the Observation Model 221 are described below.

Note that the measurements received at the Data Reception Module 121 are individual measurements at discrete points in time, but subsequent processing steps (e.g. Bayes Theorem at the Inference Engine 222, and the operation of the Clinical Trajectory Interpreter Module 123) require PDFs (probability density functions) as inputs, rather than discrete data points. Consequently, one of the functions of the Observation Model 221 is to intake the discrete measurements and output PDFs. This functionality is explained below, along with an (optional) step that reduces noise in the signals.

A. Comparing the Received Measurements to the Predicted PDFs of ISVs 211 {and Reducing Noise}

During the update mode 210 of the physiology observer module 122, the predicted PDFs of ISVs 211 (which were generated using the predict module and the PDFs of the ISVs at from time step $t_k$) are compared against the measurements received at the subsequent time step ($t_{k+1}$) from data reception module 121 with the help of the observation model 221, and as a result the ISVs are updated to reflect the new available information.

Figure 6:
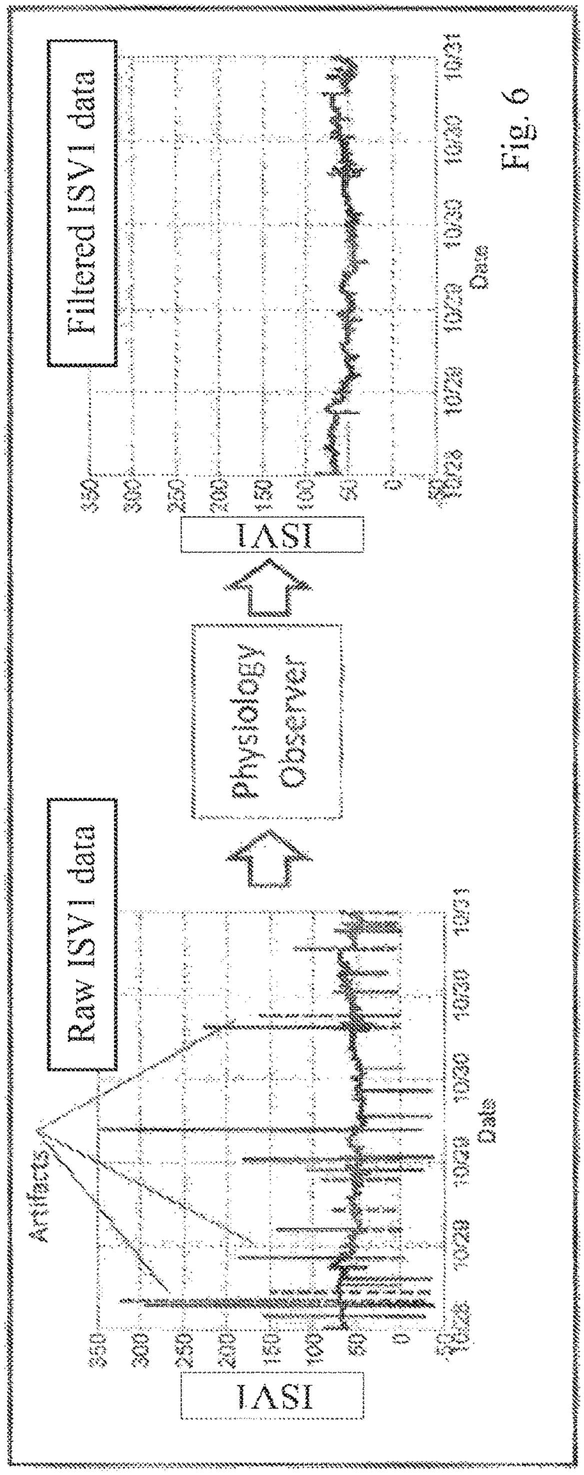
FIG. 6 illustrates conceptually an example of a process involving mean arterial blood pressure (ABPm) in accordance with the disclosure.

In addition, because physiology observer module 122 maintains estimates of each of the measurements available to the system 100 based on physiologic and statistical models, module 122 may filter artifacts of the measurements that are unrelated to the actual information contained in the measurements. This is performed by comparing the newly acquired measurements with the predicted likelihoods of probable measurements given the previous measurements. If the new measurements are considered highly unlikely by the model, they are not incorporated in the estimation. The process of comparing the measurements with their predicted likelihoods effectively filters artifacts and reduces noise. FIG. 6 shows an example of such a process involving mean arterial blood pressure (ABPm). FIG. 6 shows the raw ABPm measurements prior to being processed by the physiology observer with the measurement artifacts identified, as well as the filtered measurements after being processed by the physiology observer module 122. As can be seen, the measurement artifacts have been removed and the true signal is left.

B. Creating the Conditional Likelihood Kernel

The "Conditional Likelihood Kernel" 230 $[P(m_1(t_{k+1}), m_2(t_{k+1}), \ldots m(t_{k+1})|\mathrm{ISVs}(t_{k+1}))]$ determines how likely the currently received measurements are given the currently predicted ISVs. As can be seen from the foregoing formula, the Conditional Likelihood Kernel 230 includes a set of probability density functions of the measurements $\{m_n$ at time $t_{k+1}\}$ assuming the ISVs predicted for time step $t_{k+1}$. (i.e., the predicted PDFs of ISVs 211 for time step $t_{k+1}$). Note that from this point forward, the algorithms no longer operate on the discrete measurements from the data reception module per se.

In general, creating probably density functions of ISVs (i.e., the components of the Conditional Likelihood Kernel 230) is performed by an "inference scheme." There are several such inference schemes, including for example exact inference schemes.

In various embodiments, physiology observer module 122 may utilize a number of algorithms for estimation or inference. Depending on the physiology model used, the physiology observer module 122 may use exact inference schemes, such as the Junction Tree algorithm, or approximate inference schemes using Monte Carlo sampling such as a particle filter, or a Gaussian approximation algorithms such as a Kalman Filter or any of its variants.

As discussed, the physiology model used by physiology observer module 122 may be implemented using a probabilistic framework known as a Dynamic Bayesian Network, which graphically captures the causal and probabilistic relationship between the ISVs of the system, both at a single instance of time and over time. Because of the flexibility this type of model representation affords, the physiology observer module 122 may utilize a number of different inference algorithms. The choice of algorithm is dependent on the specifics of the physiology model used, the accuracy of the inference required by the application, and the computational resources available to the system. Used in this case, accuracy refers to whether or not an exact or approximate inference scheme is used. If the physiology observer model is of limited complexity, then an exact inference algorithm may be feasible to use. In other cases, for more complex physiology observer models, no closed form inference solution exists, or if one does exist, it is not computationally tractable given the available resources. In this case, an approximate inference scheme may be used.

The simplest case in which exact inference may be used, is when all of the ISVs in the physiology model are continuous variables, and relationships between the ISVs in the model are restricted to linear Gaussian relationships. In this case, a standard Kalman Filter algorithm can be used to perform the inference. With such algorithm, the probability density function over the ISVs is a multivariate Gaussian distribution and is represented with a mean and covariance matrix.

When all of the ISV's in the model are discrete variables, and the structure of the graph is restricted to a chain or tree, the physiology observer module 122 may use either a Forward-backward algorithm, or a Belief Propagation algorithm for inference, respectively. The Junction Tree algorithm is a generalization of these two algorithms that can be used regardless of the underlying graph structure, and so the physiology observer module 122 may also use this algorithm for inference. Junction Tree algorithm comes with additional computational costs that may not be acceptable for the application. In the case of discrete variables, the probability distribution functions can be represented in a tabular form. It should be noted that in the case where the model consists of only continuous variables with linear Gaussian relationships, these algorithms may also be used for inference, but since it can be shown that in this case these algorithms are equivalent to the Kalman Filter, the Kalman Filter is used as the example algorithm.

When the physiology model consists of both continuous and discrete ISVs with nonlinear relationships between the variables, no exact inference solution is possible. In this case, the physiology observer module 122 may use an approximate inference scheme that relies on sampling techniques. The simplest version of this type of algorithm is a Particle Filter algorithm, which uses Sequential Importance Sampling. Markov Chain Monte Carlo (MCMC) Sampling methods may also be used for more efficient sampling. Given complex and non-linear physiologic relationships, this type of approximate inference scheme affords the most flexibility. A person reasonably skilled in the relevant arts will recognize that the model and the inference schemes employed by the physiology observer module may be any combination of the above described or include other equivalent modeling and inference techniques.

Figure 7:
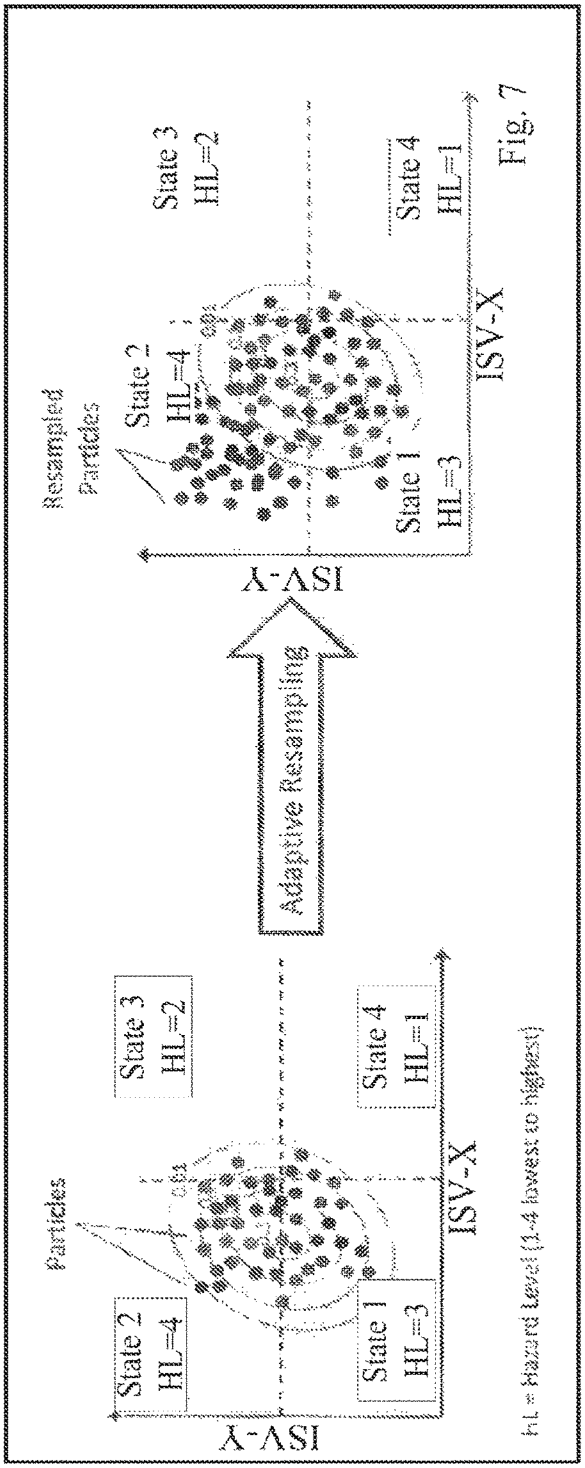
FIG. 7 illustrates conceptually an example of resampling in accordance with the disclosure.

When using particle filtering methods, a resampling scheme is necessary to avoid particle degeneracy. The physiology observer may utilize an adaptive resampling scheme. As described in detail below, regions of the ISV state space may be associated with different patient states, and different levels of hazard to the patient. The higher the number, the more hazardous that particular condition is to the patient's health. In order to ensure accurate estimation of the probability of a particular patient condition, it may be necessary to have sufficient number of sampled particles in the region. It may be most important to maintain accurate estimates of the probability of regions with high hazard level and so the adaptive resampling approach guarantees sufficient particles will be sampled in high hazard regions of the state space. FIG. 7 illustrates an example of this resampling based on two internal state variables ("ISV-X" and "ISV-Y"), which may be any internal state variables of the patient, including without limitation any of the internal state variables described herein. State 1 and State 2 have the highest hazard level. The left plot depicts the samples generated from the standard resampling. Notice there are naturally more particles in state 1 and state 2 region because these states are most probable. The right plot shows the impact of the adaptive resampling. Notice how the number of samples in the areas of highest risk has increased significantly. FIG. 35A, described further below, illustrate an example of creating the Conditional Likelihood Kernel 230 in the context of "HLHS Stage 1" example, (where "HLHS" is Hypoplastic Left Heart Syndrome").

Figure 35B:
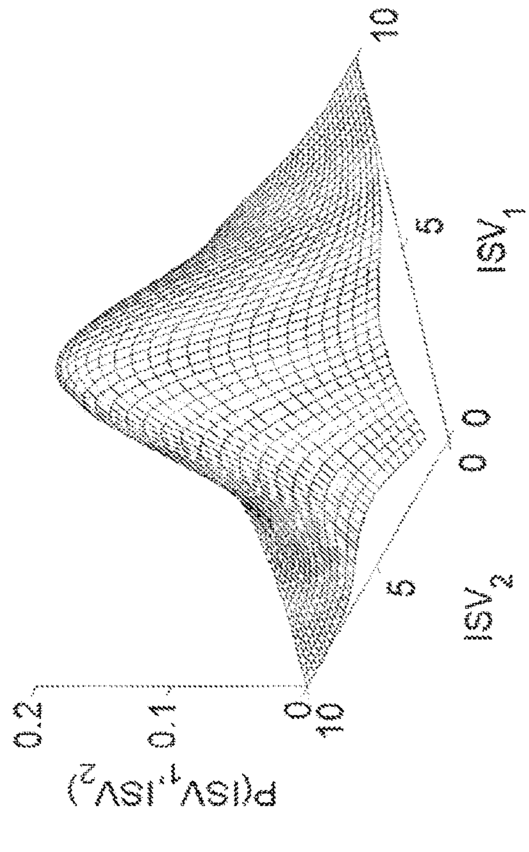
FIG. 35B and FIG. 35C schematically illustrate the Gaussian representation of the PDF of the ISVs, and the schematic of the EKF inference engine implementation.

As described in connection with FIG. 35A, in the observation model 221 inference over the DBN is performed using an Extended Kalman Filter ("EKF"), which is a variant of the Kalman Filter that extends the inference engine algorithm for use on applications where the underlying models have non-linear relationships. The extension is accomplished using a Taylor-series expansion of the non-linear relationships of the model. This approximation allows the algorithm analytically calculate a Gaussian approximation to the posterior density given the measurements provided to the system. FIG. 35B depicts this Gaussian approximation for $P(ISVs(t_{k+1})|M(t_{k+1}))$. The depicted density is a multivariate Gaussian that can be fully represented using the conditional mean of the ISVs at the current time, $\overline{ISVs}\,(t_{k+1}|t_{k+1})$, and the conditional covariance matrix of the ISVs, $\Sigma(t_{k+1}|t_{k+1})$. These quantities are conditioned on all of the available measurements up to the current time step.

Figure 35C:
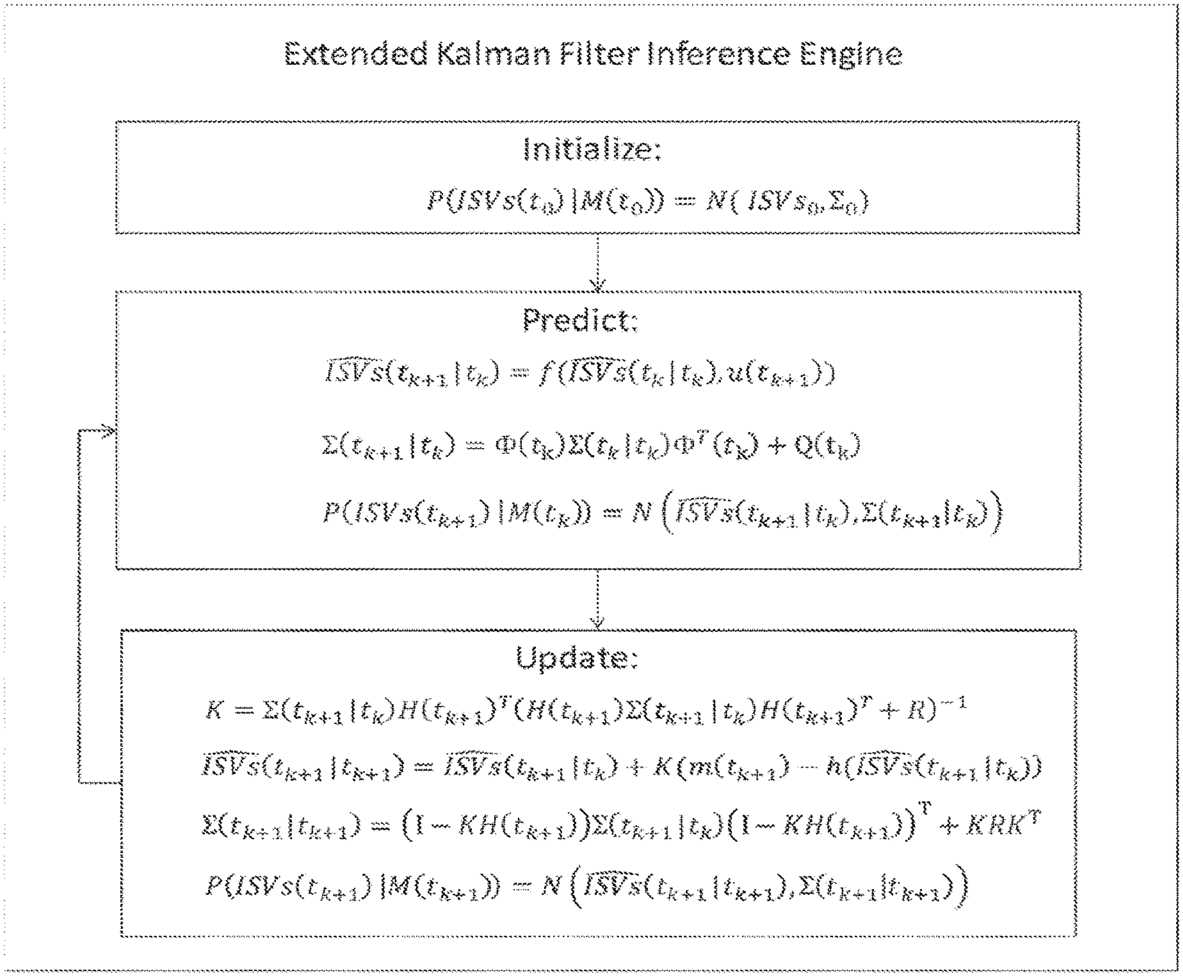

FIG. 35C, depicts the computation steps of the EKF as they relate to the current implementation. In the first step, the density is initialized using assumed initial mean and covariance conditions for the ISVs which can be informed by patient population norms or medical literature. After initialization, the density is passed to the predict step in which the ISV density is predicted forward to the time of the current measurement. This prediction is accomplished by predicting the conditional mean forward in time using the dynamic model specified in the physiology observer module, and by predicting the conditional covariance matrix utilizing a linearization of this dynamic model with the addition of "process noise" to account for uncertainty in the model of the dynamics. Note, this is the same calculation that is described in the predict module of physiology observer module except specifically for Gaussian densities. Because the EKF algorithm has a predict step incorporated in the calculation, so the physiology observer is able to utilize this predict method as part of the processing.

It should be noted that the Extended Kalman Filter, as described above, is not limited to use in creating the Conditional Likelihood Kernel 230 in the context of "HLHS Stage 1." Rather, the Extended Kalman Filter may be used to create any Conditional Likelihood Kernel 230 supported by this disclosure.

Following the prediction of the PDF to the current measurement time, the posterior density is calculated using Bayes Rule combining the new information provided by the current measurement $m(t_k)$ with the prior predicted PDF in the update step. Because of the Gaussian approximation, this calculation is analytically tractable and only involves calculating the posterior conditional mean and posterior conditional covariance matrix. Once these quantities have been updated, the entire density can be calculated.

The update step takes as an input the observation model specified in the physiology observer. Using this model, the calculation first calculates the Kalman Gain (K) which determines how much to the posterior conditional mean and covariance matrix change from prior given on the new data. The Kalman Gain is a function of the prior conditional covariance matrix, the expected noise associated with the measurement and a linearization of the observation model provided by the observer. Once the Kalman Gain is computed, the posterior conditional mean is updated from the prior mean using the difference between the measurement value and the expected measured value scaled by this gain. The posterior conditional covariance is updated from the prior in a similar manner, reducing the overall uncertainty proportional to the amount of information that the measurement provides about the underlying ISVs. Following this step, the conditional density is passed back to the predict method where it is predicted to the next (i.e., subsequent) measurement step. It is also returned to the physiology observer module.

3. Inference Engine {222}

The inference engine 222 of module 122 achieves this update by using the predicted probability density functions of the ISVs 211 as a-priori probabilities, which are updated with the statistics (i.e., the conditional likelihood kernel 230) of the received measurements from data reception module 121 to achieve the posterior probabilities reflecting the current (at time $t_{k+1}$) probability density functions of the ISVs 213. The inference engine 222 accomplishes the update step 220 with the following equation which is Bayes' Theorem, $$P(ISVs(t_{k+1})|M(t_{k+1})) = \frac{P(m_1(t_{k+1}), m_2(t_{k+1}), \ldots m_n(t_{k+1})|ISVs(t_{k+1}))P(ISVs(t_{k+1})|M(t_k))}{P(m_1(t_{k+1}), m_2(t_{k+1}), \ldots m_n(t_{k+1})|M(t_k))}$$

where:

- $P(ISVs(t_{k+1})|M(t_{k+1}))$ are the "posterior probabilities" at time step $t_{k+1}$ expressed as conditional probabilities;
- $P(m_1(t_{k+1}), m_2(t_{k+1}), \ldots m_n(t_{k+1})|ISVs(t_{k+1}))$ is the conditional likelihood kernel provided by the observation model 221 that determines how likely the currently received measurements are given the currently predicted ISVs;
- $P(ISVs(t_{k+1})|M(t_k))$ are the predicted PDFs of ISVs 211 produced in the predict model at the previous time step $t_k$ (see, e.g., FIG. 2B); and $P(m_1(t_{k+1}), m_2(t_{k+1}), \ldots m_n(t_{k+1})|M(t_k))$ is the predicted PDFs of the measurements received at the time step given the measurements received up to that time step.

At the initialization time (e.g., t=0 or $t=t_{init}$) when no then-current estimate of probability density functions of the ISVs is available, the physiology observer module 122 may utilize initial estimates 240, which may be derived from an educated guess of possible values for the ISVs or statistical analysis of previously collected patient data.

Referring now to FIG. 2A, it can be seen that the output of the Inference Engine 222 at time step $t_{k+1}$ (i.e., the "posterior probabilities" of time step $t_{k+1}$) is sent in two directions.

Figure 2B:
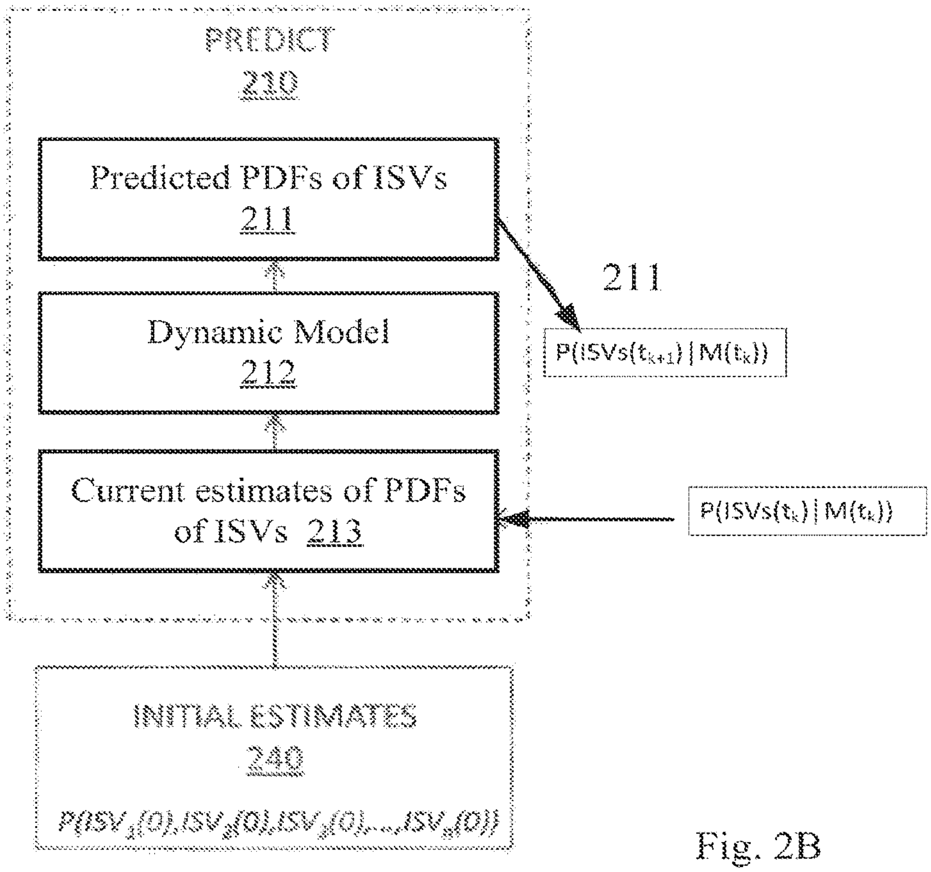
FIG. 2B schematically illustrates an embodiment of a predict module.

In the first direction, the output of the Inference Engine 222 is provided to the predict module 210, where it may be referred-to as the "current estimates of PDFs of ISVs" 213 (see, e.g., FIG. 2B and its related description).

Figure 8A:
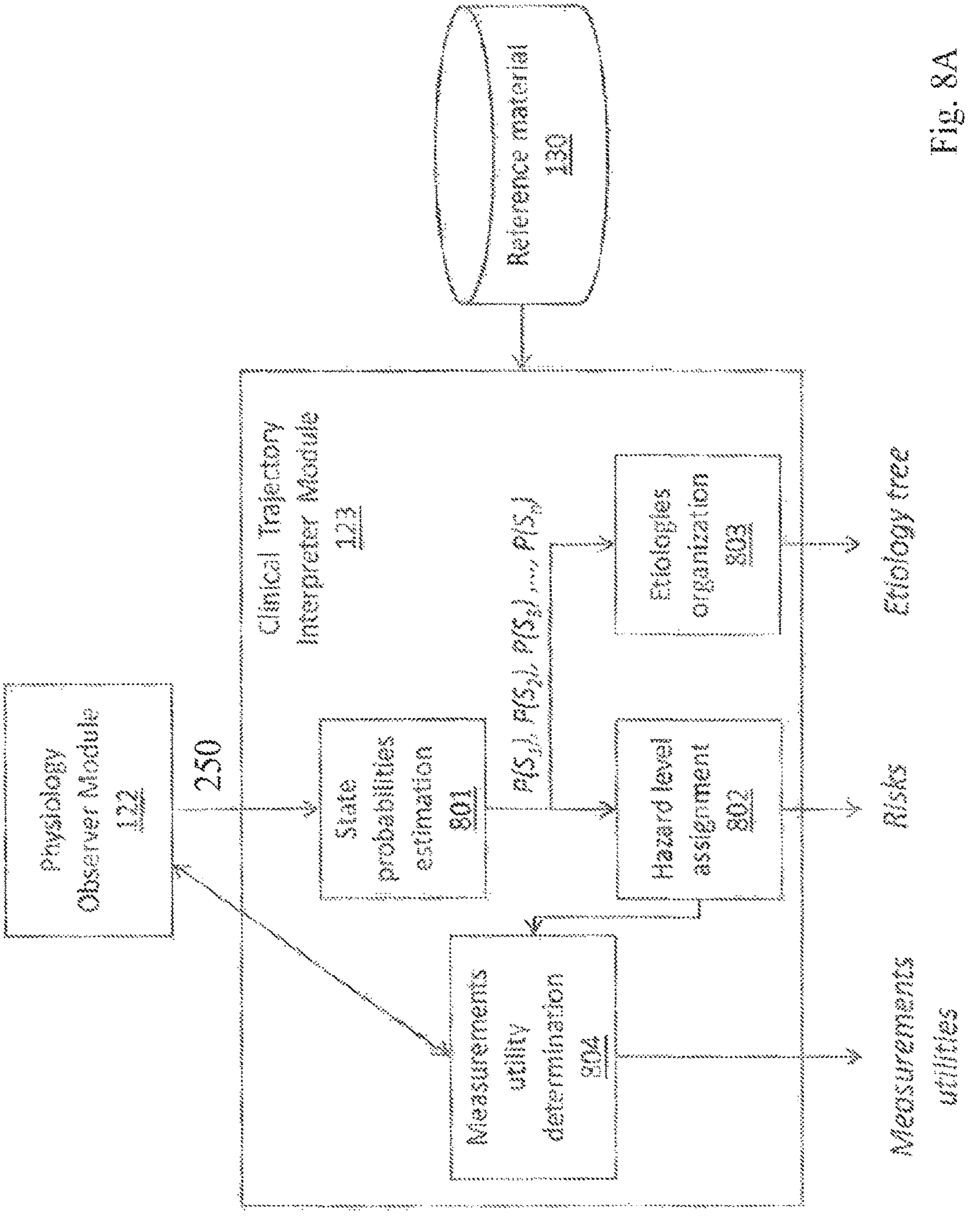
FIG. 8A and FIG. 8B each schematically illustrates, respectively, an embodiment of a clinical trajectory interpreter module using joined Probability Density Functions of ISVs and performing state probability estimation to calculate the probabilities of different patient states in accordance with the disclosure.
Figure 8B:
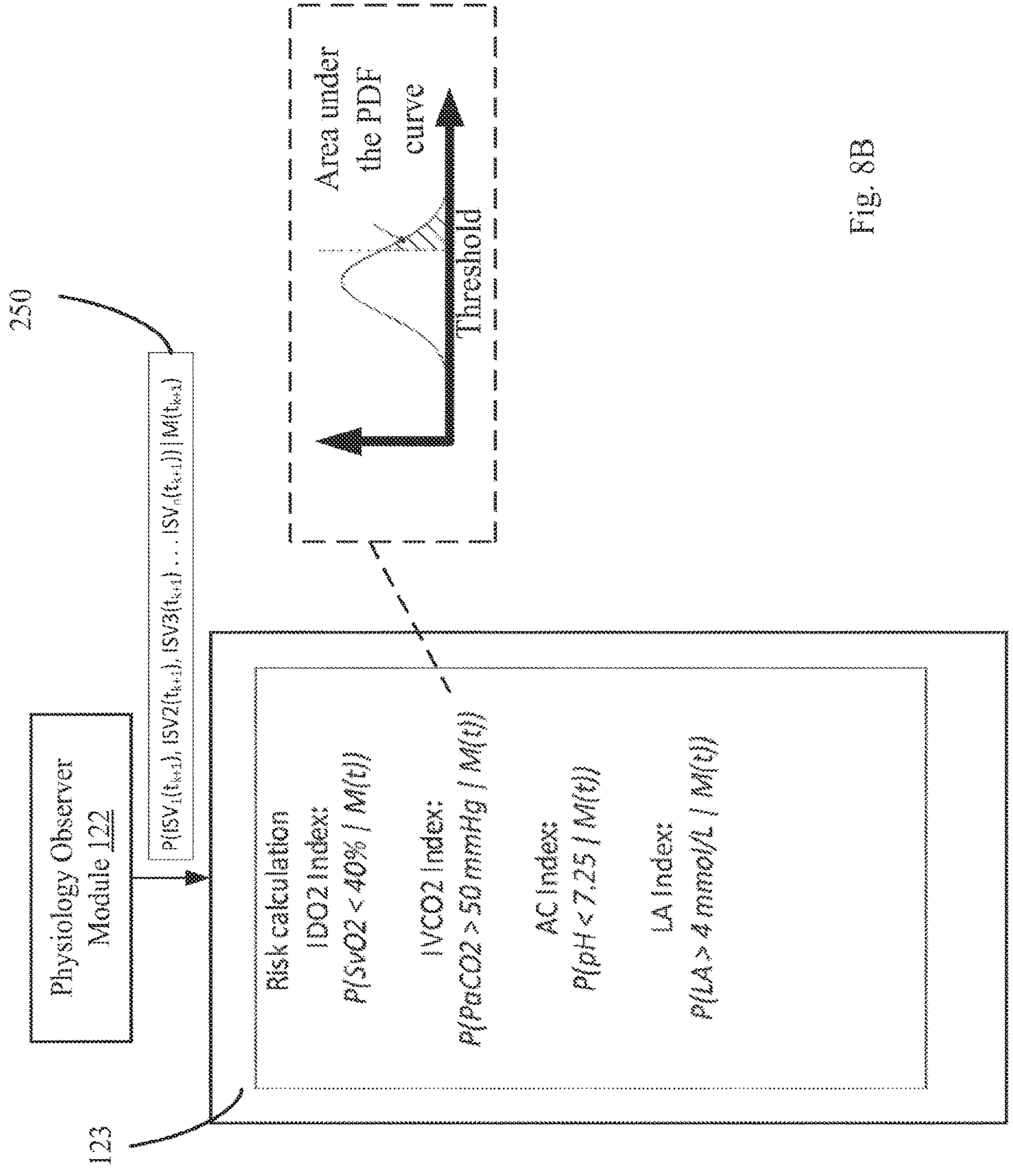

In the second direction, the output of the Inference Engine 222 at time step $t_{k+1}$ (expressed in the figures simply as probabilities) is provided to the to the clinical trajectory interpreter module 123, where that output may be referred-to as the "joint Probability Density Functions of the ISVs from the physiology observer module") 250. Operation of the to the clinical trajectory interpreter module 123 is described further herein (see, e.g., FIG. 2C and its related description; FIG. 8A and FIG. 8B).

II. Clinical Trajectory Interpreter Module {123} {Determining Patient States}

Using the posterior probabilities (250) from the Inference Engine 222 for time step $t_{k+1}$, the Clinical Trajectory Interpreter Module 123 performs state probability estimation 801 to calculate the probabilities of different patient states.

Figure 2C:
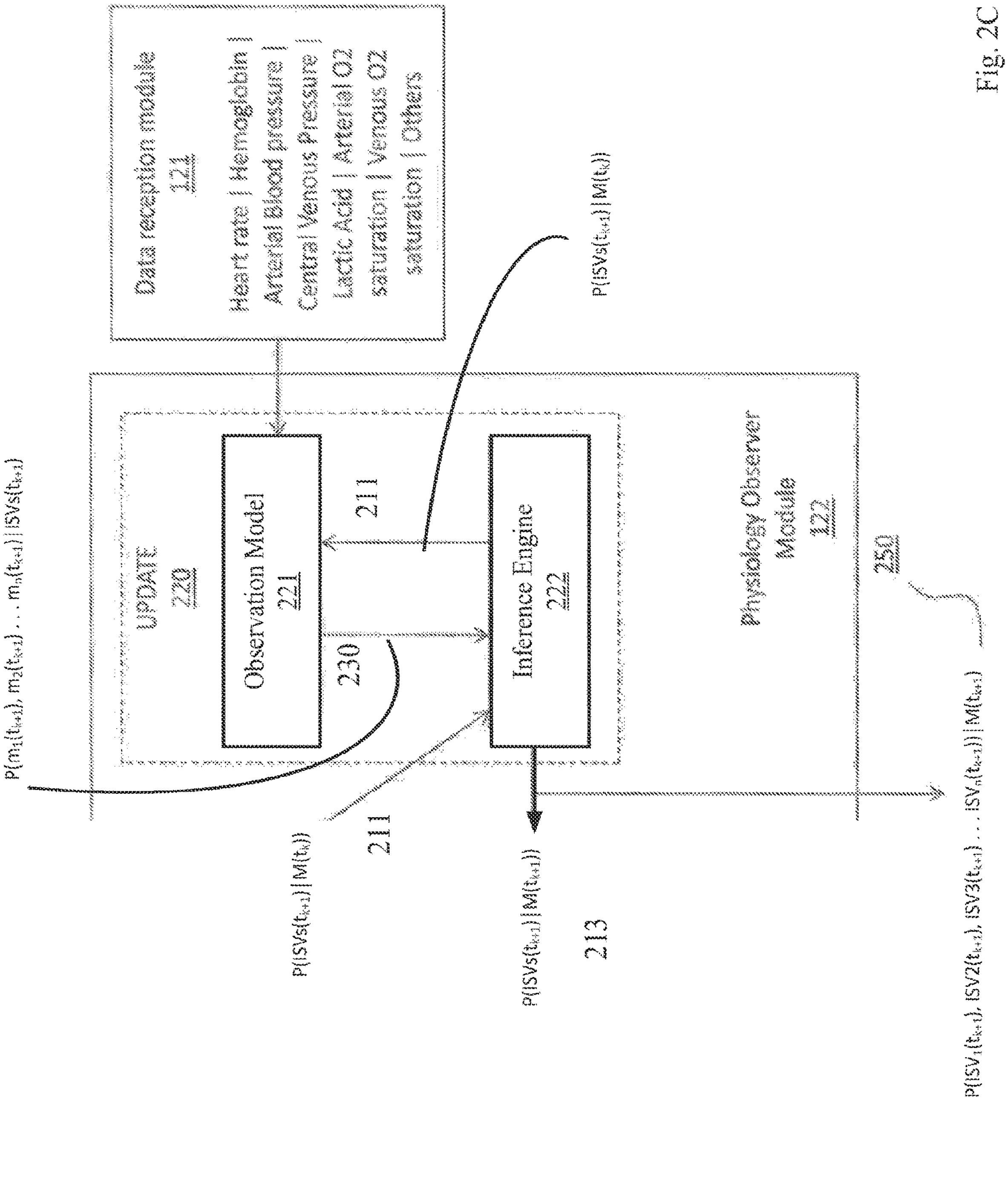
FIG. 2C schematically illustrates an embodiment of an update module.
Figure 2D:
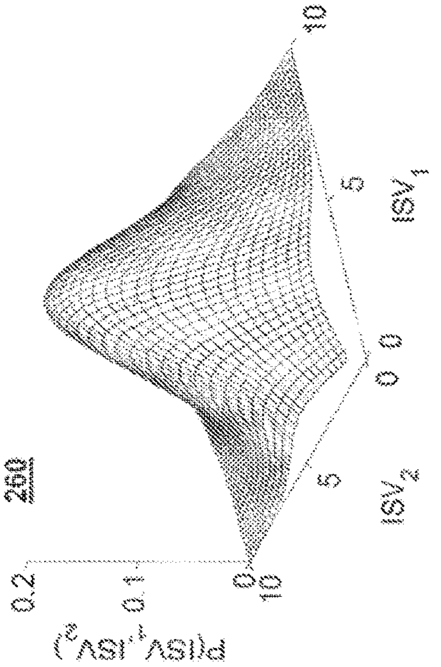
FIG. 2D, FIG. 2E and FIG. 2F illustrate conceptually exemplary graphs of probability density functions for select ISVs as generated by the physiology observer module in accordance with the disclosure.
Figure 2E:
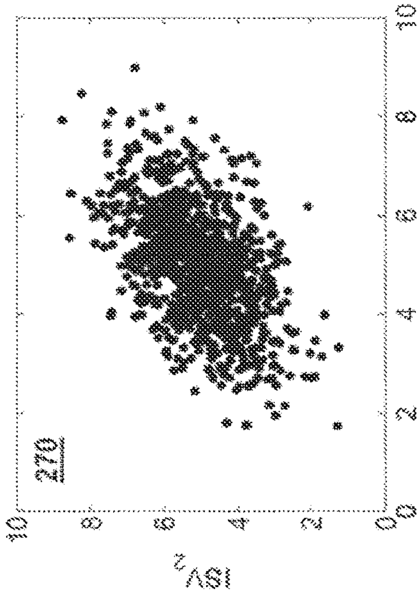
Figure 2F:
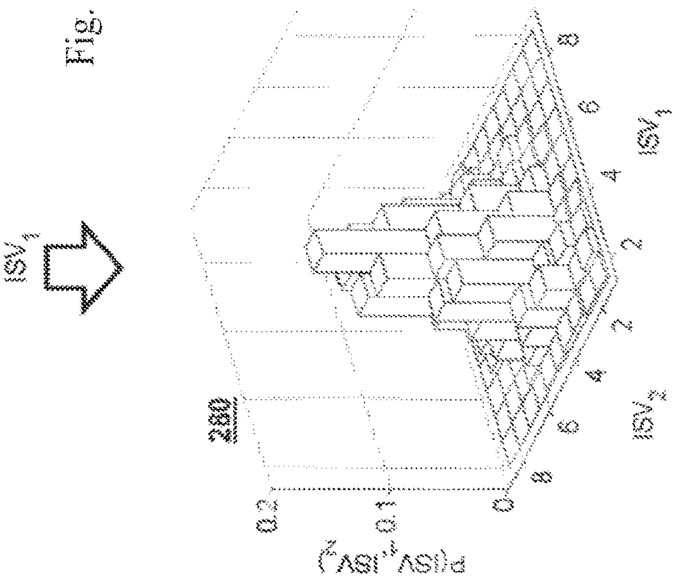

Referring now to FIG. 8A, the Clinical Trajectory Interpreter 123 takes the joint Probability Density Functions of the ISVs 250 from physiology observer module 122, and performs state probability estimation 801 to calculate the probabilities of different patient states. The Probability Density Functions of the ISVs may be defined in closed form, for example multidimensional Gaussians 260, or approximated by histogram 280 of particles 270, as illustrated in FIG. 2D, FIG. 2E and FIG. 2F. In both cases, the probability density functions of the ISVs can be referred to as: (ISV1(t), ISV2(t), . . . , ISVn(t)), where tis the time they refer to.

FIG. 8A may refer to the output 250 of the Inference Engine 222 as "the joint Probability Density Functions of the ISVs from the physiology observer module." This data may be represented in a variety of ways: the Probability Density Functions of the ISVs may be defined in closed form, for example multidimensional Gaussians 260, or approximated by histogram 280 of particles 270, as illustrated in FIG. 2D, FIG. 2F and FIG. 2G.

Determining the patient states (i.e., "determining the probability of the patient being in a particular state $S_i$") may be done in a variety of ways.

Generally, the PDFs of the ISVs define a domain. In illustrative embodiments, the domain is partitioned into quadrants, each quadrant representing a patient state. The probability that the patient is in a given one of the four patient states is determined by the quantity of the PDFs of the ISV's located within the given quadrant.

This may be described as:

(i) partitioning a domain spanned by the internal state variables into different regions, each region defining a separate patient state; and (ii) integrating the probability density functions over the regions corresponding to each particular patient state to produce probabilities that the patient may be classified under each of said possible patient states.

FIG. 2B: Multidimensional Gaussian 260

Where the data is in the form of a multidimensional Gaussian 260, integration may be performed directly:

$$P(S_i(t)) = \int_{-\infty}^{\infty} \ldots \int_{-\infty}^{\infty} P(S|ISV_1, ISV_2, \ldots, ISV_n)P(ISV_1(t), ISV_2(t), \ldots, ISV_n(t))dISV_1 \ldots dISV_n$$

FIG. 2E and FIG. 2F: Histogram of Particles 270

Figure 9:
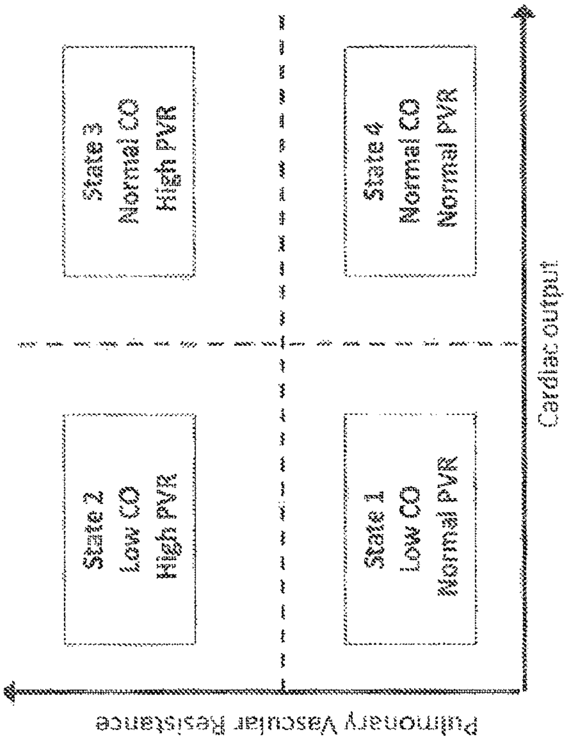
FIG. 9 illustrates conceptually a non-limiting example of a definition of a patient state employed by the clinical trajectory interpreter module in accordance with the disclosure.

In case that the output 250 of the Inference Engine 222 is approximated by a histogram 280 of particles 270 and $P(S|ISV_1, ISV_2, \ldots, ISV_n)$ is defined by a partition of the space spanned by $ISV_1, ISV_2, \ldots, ISV_n$ into regions as shown in FIG. 9, the probability $P(S_i(t))$ may be calculated by calculating the fraction of particles 270 in each region.

Example: FIG. 9

FIG. 9 illustrates a non-limiting example of a definition of a patient state that may be employed by the clinical trajectory interpreter module 123. Specifically, it assumes that the function $P(S|ISV_1, ISV_2, \ldots, ISV_n)$ may be defined by partitioning the domain spanned by the internal state variables $ISV_1, ISV_2, \ldots, ISV_n$. The particular example assumes that the patient physiology is described by two internal state variables: Pulmonary Vascular Resistance (PVR) and Cardiac Output (CO). The particular risks and respective etiologies that may be captured by these two ISVs emanate from the effects of increased pulmonary vascular resistance on the circulation. Specifically, high PVR may cause right-heart failure and consequently reduced cardiac output. Therefore, PVR can be used to define the attributes of Normal PVR and High PVR, and CO to define the attributes of Normal CO and Low CO, by assigning thresholds with the two variables. By combining these attributed, four separate states can be defined: State 1: Low CO, Normal PVR; State 2: Low CO, High PVR; State 3: Normal CO, High PVR; State 4: Normal CO Normal PVR.

Figure 10:
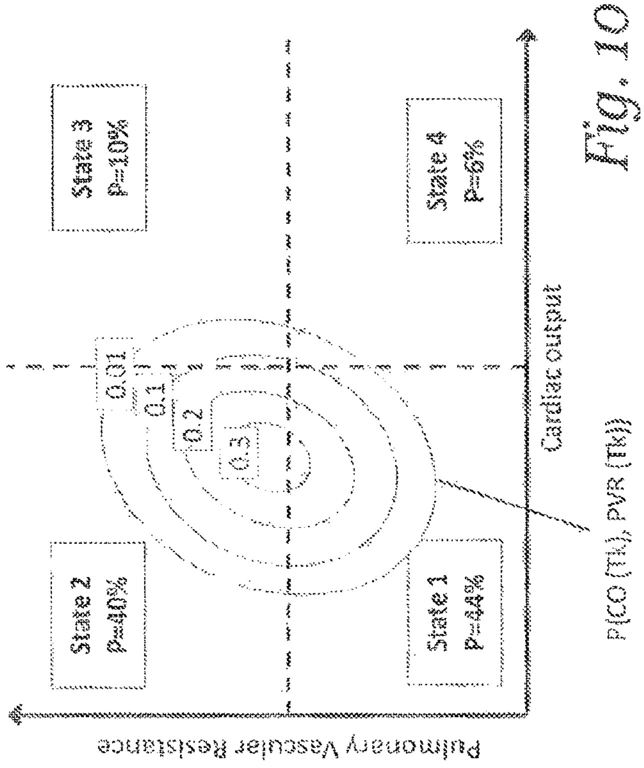
FIG. 10 illustrates conceptually a non-limiting example of how a clinical trajectory interpreter module may employ the definition of patient states to assign probabilities that the patient may be classified under each of the four possible patient states at a particular point of time.

Example: FIG. 10

FIG. 10 illustrates a non-limiting example of how the clinical trajectory interpreter module 123 may employ the definition of patient states to assign probabilities that the patient may be classified under each of the four possible patient states at a particular point of time. In the example, the clinical trajectory interpreter module 123 takes the joint probability density function of P(Cardiac Output (Tk), Pulmonary Vascular Resistance (Tk)) and integrates it over the regions corresponding to each particular state, which produces P(S1(Tk)), P(S2(Tk)), P(S3(Tk)), and P(S4(Tk)). In this way, the clinical trajectory interpreter module 123 assigns a probability that a particular patient state is ongoing, given the information provided by the physiology observer module 122. Note that if the output of the physiology observer module 122 is not a closed form function 260 but a histogram 280 of particles 270, the clinical interpreter will not perform integration but just calculate the relative fraction of particles 270 within each region.

Figure 11:
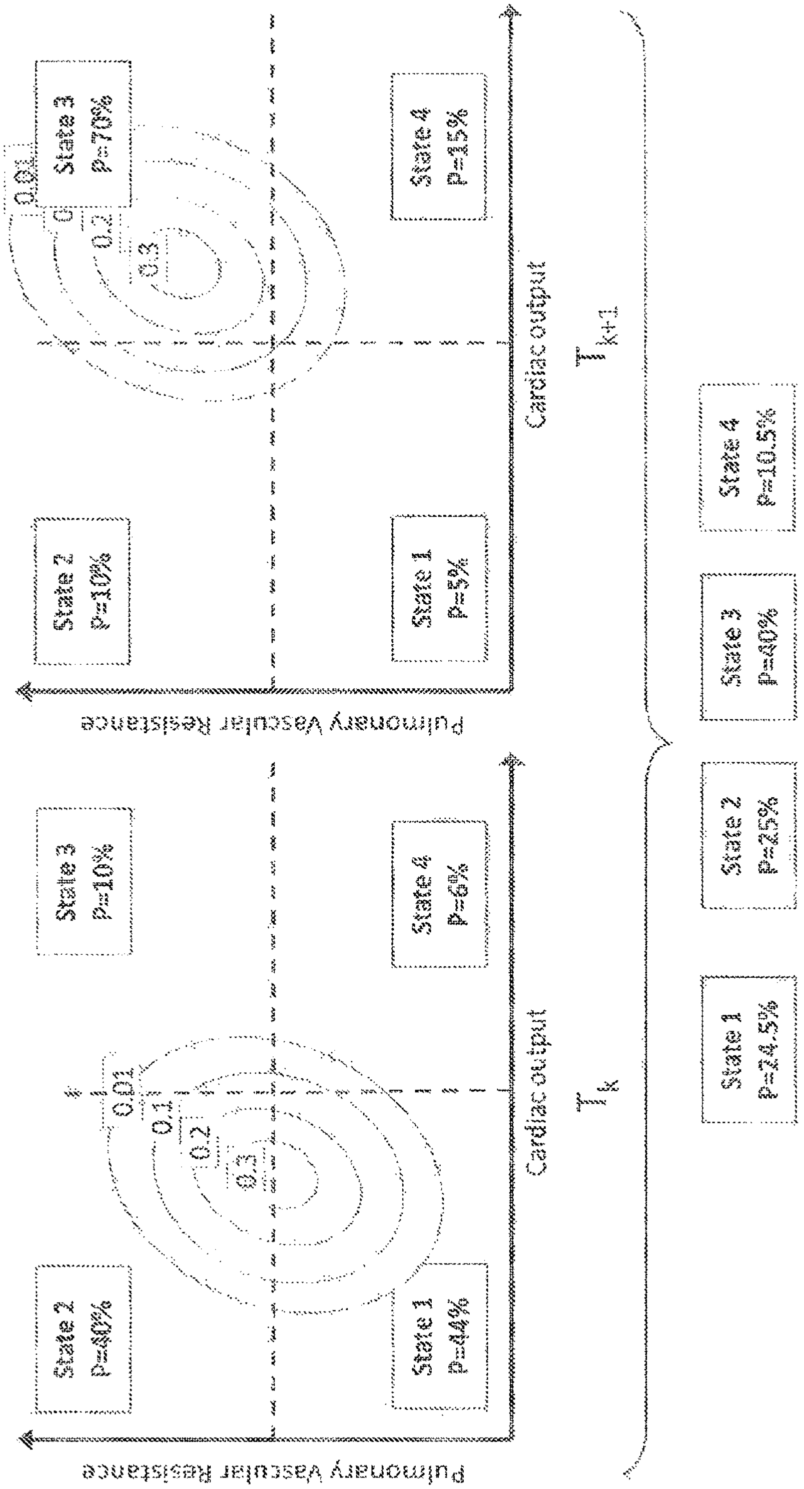
FIG. 11 illustrates conceptually an alternative approach of estimating the probabilities for different patient states in accordance with the disclosure.

Example: FIG. 11

FIG. 11 illustrates an alternative approach of estimating the probabilities for different patient states. In this alternative approach, to calculate the probabilities P(S1), P(S2), P(S3) and P(S4), the clinical trajectory interpreter module 123 employs the joint probability functions of the ISVs for two consecutive time windows $T_k$ and $T_{k+1}$ to calculate a moving window average. Note in the example that the size of the window is doubled for two time instances, which indicates that the window may be of an arbitrary, suitable size. As a result of this moving window averaging, the clinical trajectory interpreter module 123 performs a dynamic analysis of the trajectory of the ISVs. That is, it gives a metric of the probability that the physiology trajectory, as described by the ISVs, may be found in a particular region in a particular time frame. In other words, this probability calculation gives an estimate of the probability that a particular patient state may be ongoing in the chosen time-frame, as opposed to just at a chosen time instance.

Figure 3:
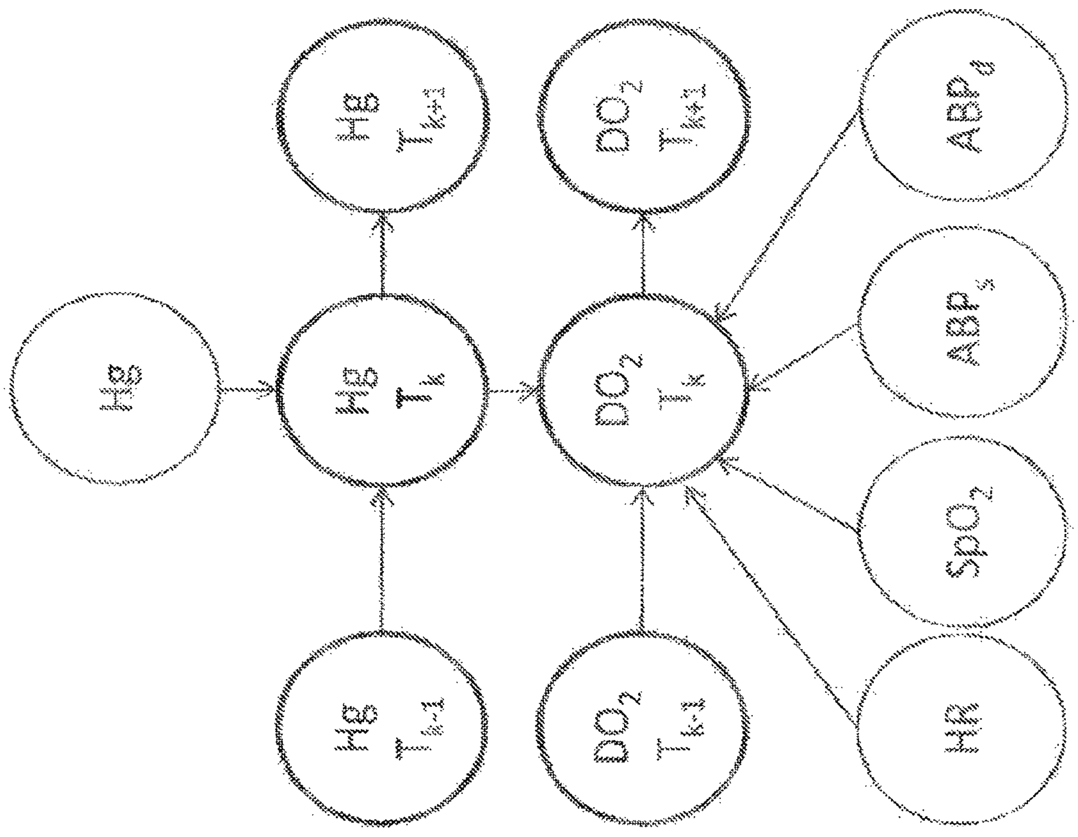
FIG. 3 illustrates conceptually a non-limiting example of a physiology observer process in accordance with the disclosure.

FIG. 3 illustrates a non-limiting example of models that enable the physiology observer in accordance with the present disclosure. While not directly observable, the management of oxygen delivery, DO2, is an important part of critical care. Therefore, precise estimation of DO2 can inform improved clinical practice. In the illustrated example, this estimation is achieved through the measurements of hemoglobin concentration (Hg), heart rate (HR), diastolic and systolic arterial blood pressures, and SpO2. The dynamic model 212 assumes that oxygen delivery is driven by a feedback process which stabilizes it against stochastic disturbances. Similarly, hemoglobin concentration is controlled around the norm value of 15 mg/dL. The observation model 221 takes into account the relationship between arterial oxygen saturation SpO2, hemoglobin concentration and arterial oxygen content CaO2, the dependence of the difference between systolic, ABPs, and diastolic, ABPd, arterial blood pressures (also called pulse pressure) on the stroke volume, and the relationship between heart rate, HR, stroke volume, SV, and cardiac output. The two models are abstracted as a Dynamic Bayesian Network (DBN), and the physiology observer module 122 utilizes the DBN to continuously track the oxygen delivery. A Dynamic Bayesian Network is a systematic way to represent statistical dependencies in terms of a graph whose vertices signify variables (observable and unobservable), and whose edges show causal relationships. Further descriptions of an exemplary DBN for DO2 estimation can be found in U.S. Provisional Application No. 61/699,492, filed on Sep. 11, 2012, entitled SYSTEMS AND METHODS FOR EVALUATING CLINICAL TRAJECTORIES AND TREATMENT STRATEGIES FOR OUTPATIENT CARE, and U.S. Provisional Application No. 61/684,241, filed on Aug. 17, 2012, entitled SYSTEM AND METHODS FOR PROVIDING RISK ASSESSMENT IN ASSISTING CLINICIANS WITH EFFICIENT AND EFFECTIVE BLOOD MANAGEMENT, to which priority is claimed, the disclosure of which is incorporated herein by reference.

Figure 4A:
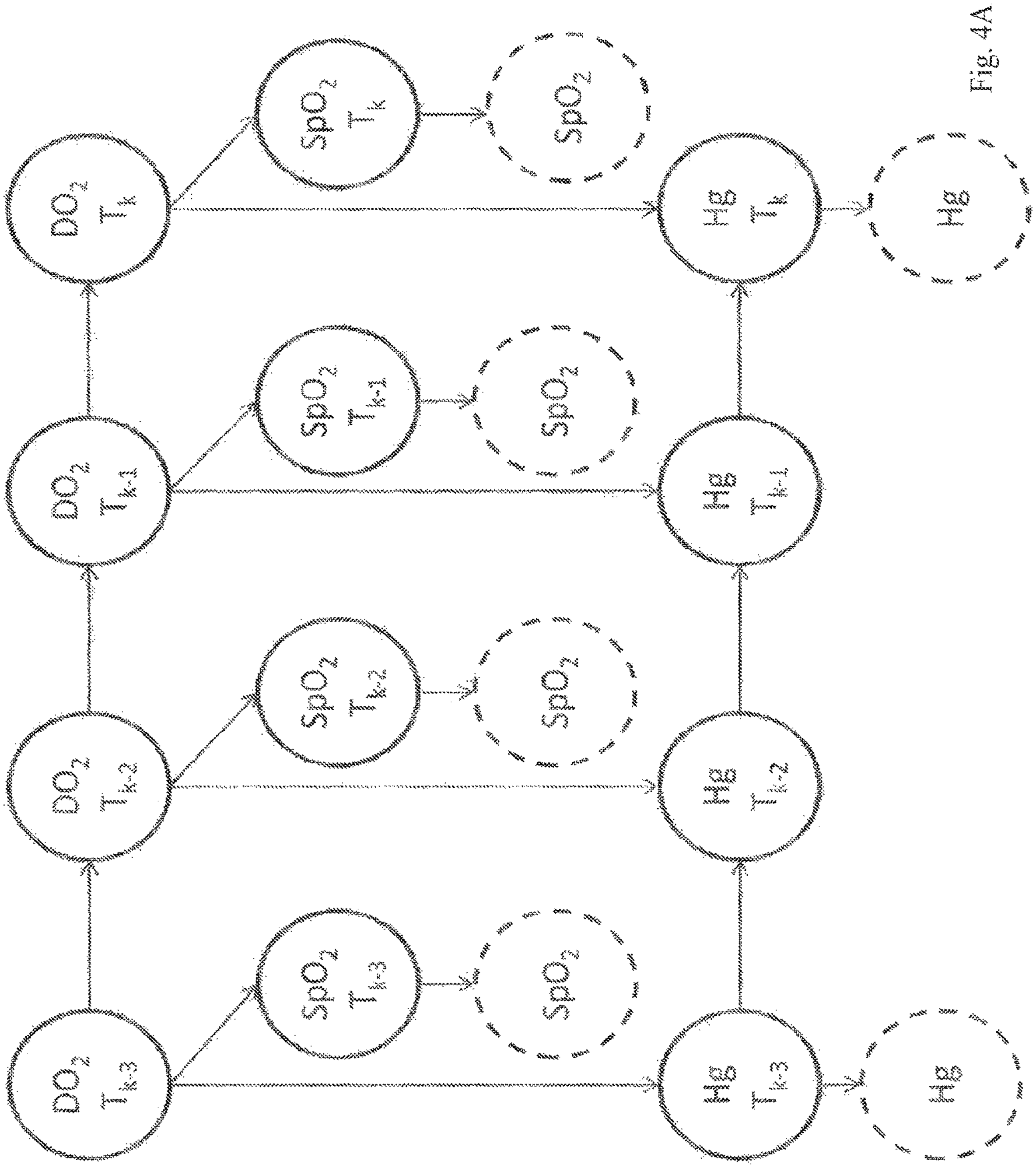
FIG. 4A illustrates conceptually a non-limiting example of the physiology observer process in accordance with the disclosure.

FIG. 4A depicts a non-limiting example of the physiology observer described above tracking DO2, but over a longer time interval, i.e., four (4) time steps. In the observer, the main hidden ISV is the oxygen delivery variable (DO2). The two types of measurements, Hemoglobin (Hg) and oximetry (SpO2) are in dashed circles in FIG. 4A. SpO2 is an example of the continuous or periodic measurements that the physiology observer module 122 receives from sensors, such as bedside monitors 102 and treatment devices 104 connected to the patient 101 that continuously report information. Hemoglobin (Hg) is an example of an intermittent or aperiodic measurement extracted from patient lab work that is available to the observer on a sporadic and irregular basis, and latent at times, relative to current system time. The physiology observer module 122 is capable of handling both types of measurements because, along with tracking the hidden ISVs, e.g. DO2, module 122 also continuously maintains estimates of the observed values for all types of measurements, even when measurements are not present. FIG. 4A depicts these estimates for the case of SpO2 and Hg. As can be seen, the SpO2 measurements are available regularly at each time step, whereas Hg is only available at two of the time steps.

Figure 4B:
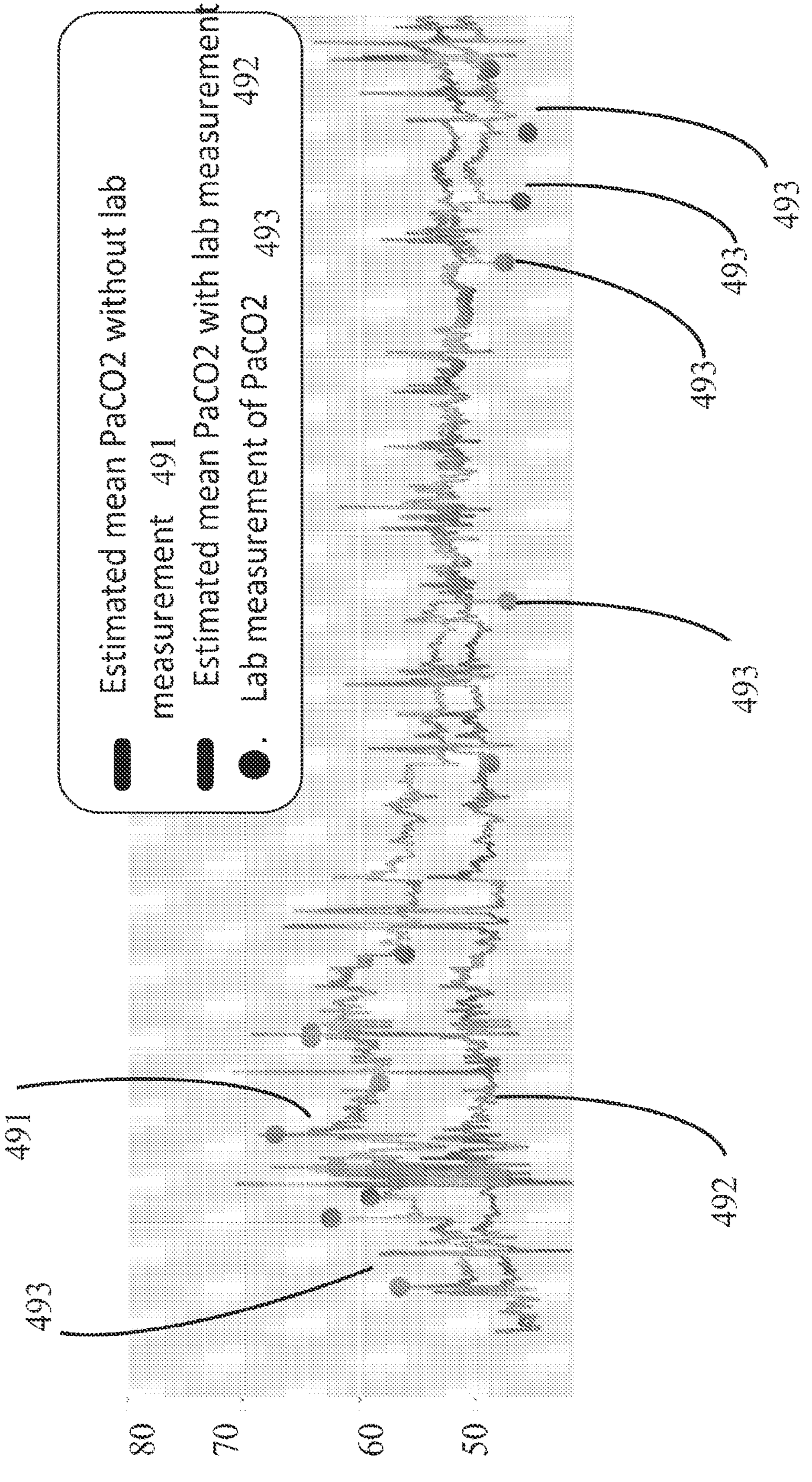
FIG. 4B illustrates a method applying intermittent laboratory data through the physiology observer module to achieve better accuracy in an estimated ISV PDF.

FIG. 4B illustrates a method applying intermittent laboratory data through the physiology observer module to achieve better accuracy in an estimated ISV PDF. The specific example shows what the estimated mean of the PDF of the PaCO2 ISV is without incorporating arterial blood gases that directly measure this internal state variable, and how this estimate changes as arterial blood gas measurements are introduced into the system. Specifically, the estimated mean of the PaCO2 ISV is much closer to the actual measured PaCO2 when these measurements are incorporated as inputs.

This is achieved as follows:

The physiology observer module includes a hidden ISV called alveolar dead space which takes into account that lung ventilation may not be efficiently removing CO2 from the blood. I.e. the higher the alveolar dead space is, the higher the difference is between expired CO2 as measured by end-tidal CO2 measurement (EtCO2) and arterial CO2 as measured by PaCO2 arterial blood gases.

The PDF of this ISV is used to predict various measurements acquired from the patient, some of which might include minute ventilation, end-tidal CO2, and PaCO2 arterial blood gases As a non-limiting example, if minute ventilation and end-tidal CO2 are continuously acquired measurements at every time $t_{k+1}$, the inference engine can use Bayes theorem to update the PDF of the various ISVs, one of which is PaCO2. That is, in the formula, $$P(ISVs(t_{k+1})|M(t_{k+1})) = \frac{P(m_1(t_{k+1}), m_2(t_{k+1})|ISVs(t_{k+1}))P(ISVs(t_{k+1})|M(t_k))}{P(m_1(t_{k+1}), m_2(t_{k+1})|M(t_k))}$$

$m_1$ and, $m_2$ are measured values of EtCO2 and minute ventilation.

When a PaCO2 blood gas measurement is acquired at next time $t_{k+2}$ in conjunction with measurements of end-tidal EtCO2 and minute ventilation, the measurement vector is augmented with the PaCO2 measurement and the above formula becomes:

$$P(ISVs(t_{k+2})|M(t_{k+2})) = \frac{P(m_1(t_{k+2}), m_2(t_{k+2}), m_3(t_{k+2})|ISVs(t_{k+2}))P(ISVs(t_{k+2})|M(t_{k+1}))}{P(m_1(t_{k+2}), m_2(t_{k+2}), m_3(t_{k+2})|M(t_{k+1}))}$$

Where again $m_1$ and, $m_2$ are measured values of EtCO2 and minute ventilation, and $m_3$ is the PaCO2 measurement.

This additional information is utilized in two ways. First, the uncertainty in the PaCO2 ISV PDF is reduced (See FIG. 4B) given the more accurate direct observation of PaCO2 provided by the arterial blood gas. Second, since the PaCO2 and EtCO2 measurements are observed simultaneously, the combined information is used by the physiology observer to estimate alveolar dead-space more precisely.

When the new estimated PDF of alveolar dead-space is propagated forward in time by the dynamic model, the accuracy of the estimated PaCO2 PDF is improved even when $m_3$, the PaCO2 measurement, is not present.

Figure 5:
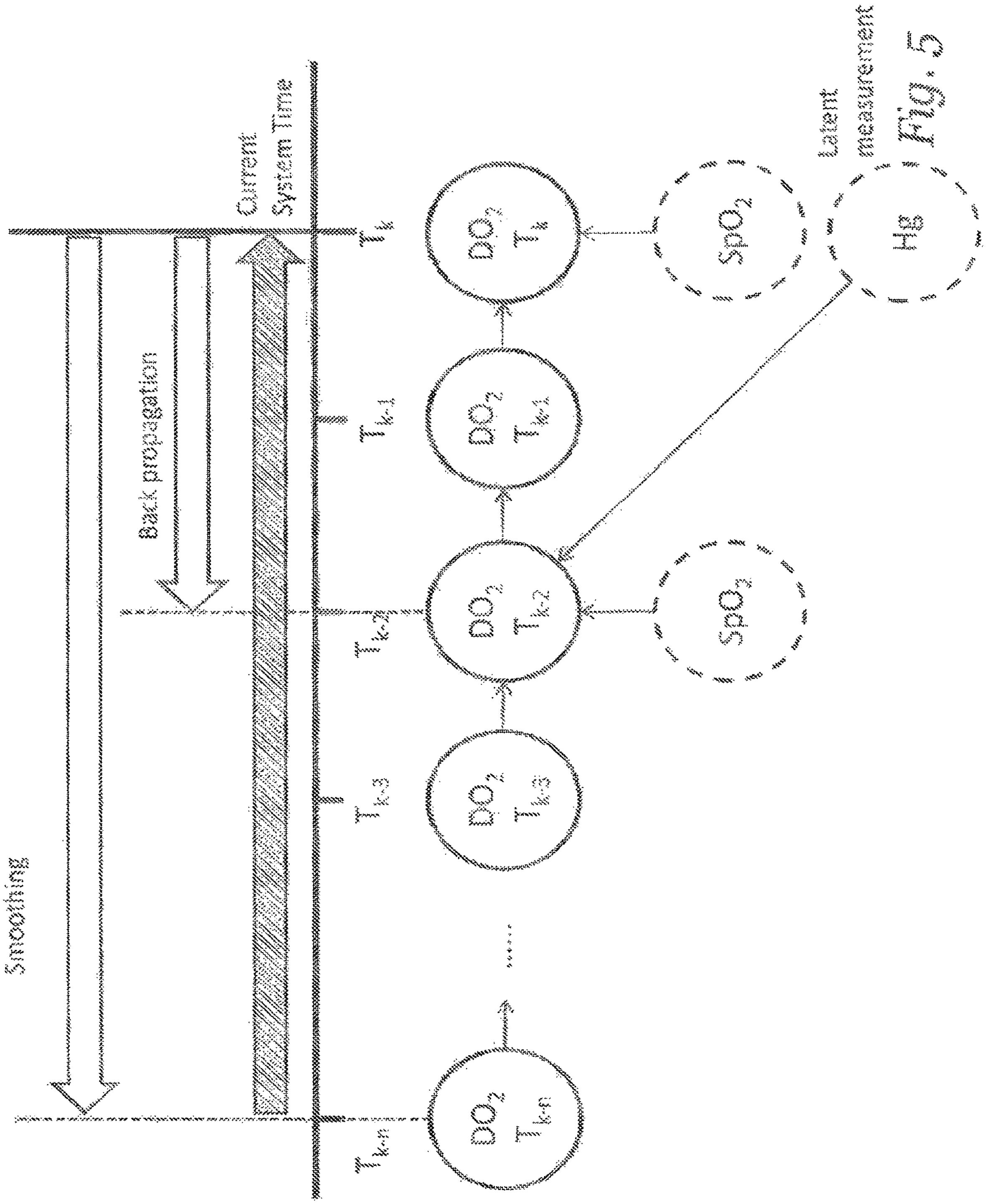
FIG. 5 illustrates conceptually a time line, wherein back propagation is used to incorporate information in accordance with the disclosure.

As mentioned above, certain measurements, such as Hemoglobin, are available to the system with an unknown amount of time latency, meaning the measurements are valid in the past relative to the current time and the time they arrive over the data communication links. The physiology observer module 122 may handle such out of sequence measurements using back propagation, in which the current estimates of the ISVs are projected back in time to the time of validity of the measurements, so that the information from the latent measurement can be incorporated correctly. FIG. 5 depicts such time line. In FIG. 5, hemoglobin arrives at the current system time, $t_k$, but is valid and associated back to the ISV (DO2) at time $T_{k-2}$. Back propagation is the method of updating the current ISVs probability estimates P(ISVs $(t_k)|M(t_k)$) with a measurement that is latent relative to the current time, $m(t_{k-n})$. Back propagation is accomplished in a similar manner to the prediction method described previously. There is a transition probability kernel, P(ISVs($t_{k-n}$) |ISVs($t_k$)), that defines how the current probabilities evolve backwards in time. This can then be used to compute probabilities of the ISVs at time $t_{k-n}$ given the current set of measurements which excludes the latent measurement, as follows:

$$P(\text{ISVs}(t_{k-n})|M(t_k))=\int_{ISVs\in ISV}P(\text{ISVs}(t_{k-n})|\text{ISVs}(t_k))P(\text{ISVs}(t_k)|M(t_k))d\text{ISVs}$$

Once these probabilities are computed, the latent measurement information is incorporated using Bayes' rule in the standard update:

$$P(ISVs(t_{k-n})|M(t_k), m(t_{k-n})) = \frac{P(m(t_{k-n})|ISVs(t_{k-n}))P(ISVs(t_{k-n})|M(t_k)}{P(M(t_k), m(t_{k-n}))}$$

The updated probabilities are then propagated back to the current time $t_k$ using the prediction step described earlier. Back propagation can be used to incorporate the information.

Another functionality of the physiology observer module 122 includes smoothing. The care provider using the system 100 may be interested in the patient state at some past time. With smoothing, the physiology observer module 122 may provide a more accurate estimate of the patient ISVs at that time in the past by incorporating all of the new measurements that the system has received since that time, consequently providing a better estimate than the original filtered estimate of the overall patient state at that time to the user, computing P(ISVs($t_{k-n}$)|M($t_k$)). This is accomplished using the first step of back propagation in which the probability estimates at time $t_k$ which incorporate all measurements up to that time are evolved backwards to the time of interest $t_k$ n using the defined transition probability kernel. This is also depicted in FIG. 5, in which the user is interested in the patient state at $t_k$ n and the estimates are smoothed back to that time.

Because physiology observer module 122 maintains estimates of each of the measurements available to the system 100 based on physiologic and statistical models, module 122 may filter artifacts of the measurements that are unrelated to the actual information contained in the measurements. This is performed by comparing the newly acquired measurements with the predicted likelihoods of probable measurements given the previous measurements. If the new measurements are considered highly unlikely by the model, they are not incorporated in the estimation. The process of comparing the measurements with their predicted likelihoods effectively filters artifacts and reduces noise. FIG. 6 shows an example of such a process involving an internal state variable ("ISV1"), which may be any internal state variable of the patient, including any internal state variable described herein. For example, the internal state variable in some embodiments may be mean arterial blood pressure (ABPm). Because ABPm is collected using an intravenous catheter, the measured signals are often corrupted with artifacts that result in incorrect measurements when the catheter is used for medical procedures such as blood draws or line flushes. FIG. 6 shows the raw ISV (ABPm) measurements prior to being processed by the physiology observer with the measurement artifacts identified, as well as the filtered measurements after being processed by the physiology observer module 122. As can be seen, the measurement artifacts have been removed and the true signal is left.

Clinical Trajectory Interpreter

Referring now to FIG. 8A and FIG. 8B, the Clinical Trajectory Interpreter 123 takes the joint Probability Density Functions of the ISVs from physiology observer module 122, and performs state probability estimation 801 to calculate the probabilities of different patient states. The Probability Density Functions of the ISVs may be defined in closed form, for example multidimensional Gaussians 260, or approximated by histogram 280 of particles 270, as illustrated in FIGS. 2B-D. In both cases, the probability density functions of the ISVs can be referred to as: P(ISV1 (t), ISV2(t), . . . , $ISV_n$(t)), where t is the time they refer to. Given the internal state variables the patient state may be defined by a conditional probability density function:

P(S|ISV1, SV2, . . . , ISVn), where $S \in S_1, S_2, \ldots, S_N$ represents all possible patient states $S_i$ Then determining the probability of the patient being in a particular state $S_i$ may be performed by the equation:

$$P(S_i(t))=\int_{-\infty}^{\infty}\ldots\int_{-\infty}^{\infty}P(S|ISV_1,ISV_2,\ldots,ISV_n)P(ISV_1(t),ISV_2(t),\ldots,ISV_n(t))dISV_1\ldots dISV_n$$

In case that P(ISV1(t), ISV2(t), . . . , ISVn(t)) is defined by a closed form function such as multidimensional Gaussian 260, the integration may be performed directly. In case that P(ISV1(t), ISV2(t), . . . , ISVn(t) is approximated by a histogram 280 of particles 270 and P(S|$ISV_1$, $ISV_2$, . . . , ISVn) is defined by a partition of the space spanned by $ISV_1$, $ISV_2$, . . . , ISVn n into regions as shown in FIG. 9, the probability P($S_i$(t)) may be calculated by calculating the fraction of particles 270 in each region.

Once patient state probabilities are estimated, the clinical trajectory interpreter module 123 may assign different hazard levels 802 for each patient state or organize the states into different etiologies 803. The clinical trajectory interpreter module 123, in conjunction with the physiology observer module 122, may perform measurements utility determination 804 to determine the utility of different invasive measurements such as invasive blood pressures or invasive oxygen saturation monitoring. In one embodiment, the Clinical trajectory interpreter Module 123 determines the probabilities that the patient is in a particular state, rather than the exact state that the patient is in.

FIG. 8B illustrates an embodiment of a Clinical Trajectory Interpreter 123 module that may be referred-to as a Risk Calculation module. The Risk Calculation depicted calculates the probability that particular internal state variables that represent key bio-markers, e.g. SvO2 or PaCO2, are abnormal, i.e. above or below particular pre-defined clinically significant values at a particular time (e.g., in keeping with illustrative embodiments, time $t_{k+1}$). Specifically, the Risk calculation takes as an input, the continuous probability densities estimated by the Physiology observer module for a particular time step, and calculates the cumulative probabilities of interest. The four probabilities currently calculated are 1) the probability of inadequate oxygen delivery defined as a mixed venous oxygen saturation (SvO2) below 40%, also referred to as the IDO2 Index, 2) the probability of inadequate ventilation of carbon dioxide, defined as arterial partial pressure greater than 50 mmHg, also referred to as the IVCO2 Index, 3) the probability of acidosis, defined as blood pH below 7.25, also referred to as the AC Index, and 4) the probability of hyperlactatemia, defined as lactate blood levels greater than 4.0 mmol/L, also referred to as the LA Index.

Various patients states (adverse medical conditions), their associate internal state variables, and sensors included in a set of sensors supplying patient measurements to the system 100 are listed below.

| Patient State | Hidden ISV | Sensor(s) |
|---|---|---|
| Inadequate Oxygen Delivery | mixed venous oxygen saturation | a heart rate sensor and an SpO2 sensor, |
| Inadequate ventilation of carbon dioxide (IVCO2 Index) defined as a patient's arterial partial pressure of carbon dioxide blood being greater than a particular value, e.g. 50 mmHg | arterial partial pressure of carbon dioxide blood PaCO2 | a heart rate sensor and an SpO2 sensor, respiratory rate sensor |
| Acidosis (AC Index) defined as a patient's blood pH being less than a particular value, e.g. 7.25 | Arterial blood pH | a heart rate sensor and an SpO2 sensor, respiratory rate sensor |
| Hyperlactatemia (LA Index) defined as a patient's arterial lactate level being greater than a particular value, e.g. 4 mmol/L | arterial lactate level | a heart rate sensor and an SpO2 sensor |

As a non-limiting example, the patient state of inadequate oxygen delivery may be inferred by the invention from a heart rate and an SpO2 sensor in the following ways. The physiology observer module 122 continuously interprets ISV data based on the following understandings:

- If a patient has decreasing pulse oximetry and rising heart rate the physiology model we use will infer that there is a determinable probability of rising lactate.
- The model by the physiology observer in this example will capture explicitly the relationship between the ISVs of arterial saturation (measured by SpO2) and heart rate (measured by the heart rate sensor) and the hidden ISV of mixed venous oxygen saturation.
- As a result, at each time instance the physiology observer will update the PDF ISV of mixed venous oxygen saturation, and because of the inferred increase in heart rate and decrees in arterial saturation, the PDF will imply higher probability for lower values of the ISV SvO2.
- This in turn will be interpreted by the Clinical Interpreter module as a rising risk for inadequate oxygen delivery reflected by the calculation:

$$IDO2Index=P(SvO2<40\%|M(t_k))=\int_{-\infty}^{40}P(SvO2|M(t_k))dSvO2$$

Note that in the foregoing formula, the threshold is 40 percent, but the that illustrative embodiment does not limit all embodiments. The threshold may be determined by the clinician or system developer or operator.

Similarly, another non-limiting example is how the state of Hyperlactatemia can be calculated with the same set of sensors: i.e.:

- The model in the physiology observer can relate the state of inadequate oxygen delivery as reflected by the ISV of SvO2 as the probable onset of anaerobic metabolism.
- The model that will take into account that the more probable is that the patient is experiencing anaerobic metabolism the higher is the likelihood of lactate production, which will mean that with each update the PDF of the ISV of lactate will indicate higher probable values for lactate.

In turn the clinical trajectory interpreter module will compute the risk for the state of hyperlactatemia as:

$$LA\ \text{Index} = P\left(\text{Lactate} < 4\frac{mmol}{L}|M(t_k)\right) = \int_{-\infty}^{4} P(\text{Lactate}|M(t_k))d\ \text{Lactate}$$

Note that in the foregoing formula, the threshold is 4 mmol/L, but the that illustrative embodiment does not limit all embodiments. The threshold may be determined by the clinician or system developer or operator.

Similarly, yet another non-limiting example is using respiratory rate sensor in addition to SpO2 and Heart rate sensors to determine the probability that the patient is in a state of inadequate ventilation of carbon dioxide. In this example a rising respiratory rate and heart rate while arterial saturation stays the same may be interpreted by the model in the physiology observer as a physiologic response the probable elevation of arterial carbon dioxide. This inference will be reflected by higher probable values of the ISV of PaCO2, and the risk for the patient being in inadequate ventilation of carbon dioxide state can then be computed by:

$$\text{IVCO2Index} = P(\text{PaCO2} > 50\ \text{mmHg}|M(t_k)) = \int_{50}^{\infty} P(\text{PaCO2}|M(t_k))d\text{PaCO2}$$

Note that in the foregoing formula, the threshold is 50 mmHg, but the that illustrative embodiment does not limit all embodiments. The threshold may be determined by the clinician or system developer or operator.

Finally another example is the computation of probability that a patient is in the state of acidosis. Acidosis can be caused both by rising PaCO2 or rising lactate. An additional effect in the model of the physiology observe which captures this relationship can then infer the rising probable values of the ISVs of lactate and PaCO2 as decreasing probable values of arterial pH as captured by the PDF of this ISV. As a result the probability of the state of acidosis can be given by:

$$\text{AC Index} = P(\text{pH} < 7.25|M(t_k)) = \int_{-\infty}^{7.25} P(\text{pH}|M(t_k))d\text{pH}$$

Note that in the foregoing formula, the threshold is 7.25, but the that illustrative embodiment does not limit all embodiments. The threshold may be determined by the clinician or system developer or operator.

Figure 8C:
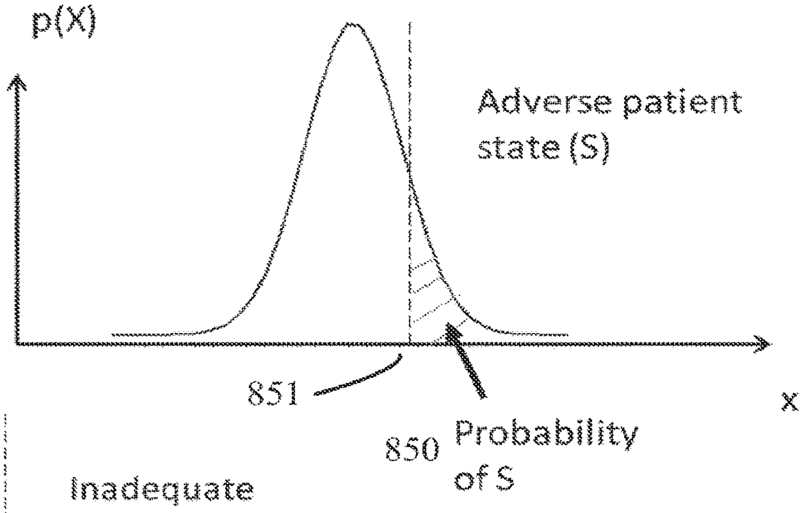
FIG. 8C, FIG. 8D, FIG. 8E, FIG. 8F and FIG. 8G each schematically illustrates, respectively, a method of determining a patient stage using probability density functions of internal state variables.

The variables SvO2, PaCO2, pH, and Lactate are all internal state variables, or related to internal state variables, for which the Physiology observer calculates the probability density of. Note, in FIG. 8B, the dashed call-out box graphically depicts an illustrative example of this calculation. FIG. 8C schematically illustrates a generic embodiment of this calculation, for a PDF of an ISV termed "p(X)." The probability 850 of adverse patient state (S) (e.g., an adverse medical condition) is defined as the area under the curve of p(X) above (or in some embodiments, below) a threshold 851. More specific embodiments are presented in FIG. 8D, FIG. 8E, FIG. 8F and FIG. 8G, discussed below. In general, the threshold in each such embodiments may be specified by the clinician (e.g., doctor, nurse, etc.) using the system 100, based for example on which adverse medical condition is suspected by the clinician.

It should be noted that each of the probabilities can be calculated from densities either conditioned on contemporaneous measurement data (e.g., measurements received for time step $t_{k+1}$) (as shown in the equations) or not conditioned on measurement data, allowing the system to produce these quantities regardless data availability levels. The calculations can be performed via standard numerical integration techniques, or when the functional form of the underlying densities is more complicated, Monte Carlo integration techniques can be used. In the current implementation, the densities are Gaussian and so standard software packages for computing these quantities are available.

Once calculated, these Risk quantities are sent to the Display and notification system module 124 for display on a display device.

Examples

Figure 8D:
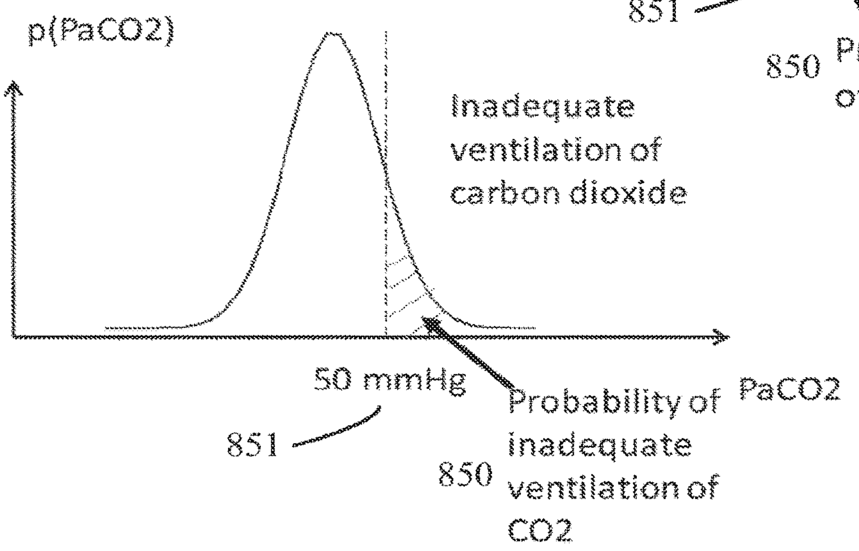

FIG. 8D illustrate the evaluation of the state of Inadequate Ventilation of Carbon Dioxide based on the ISV of partial pressure of arterial blood CO2 (PaCO2). As a non-limiting example the probability 850 of this state is computed as the cumulative distribution of p(PaCO2) greater than the 50 mmHg threshold. The resulting Clinical Risk can be displayed as an index whose instantaneous time value is given by:

$$\text{IVCO2Index} = P(\text{PaCO2} > 50\ \text{mmHg}|M(t_k)) = \int_{50}^{\infty} P(\text{PaCO2 I}M(t_k))d\text{PaCO2}$$

Figure 8E:
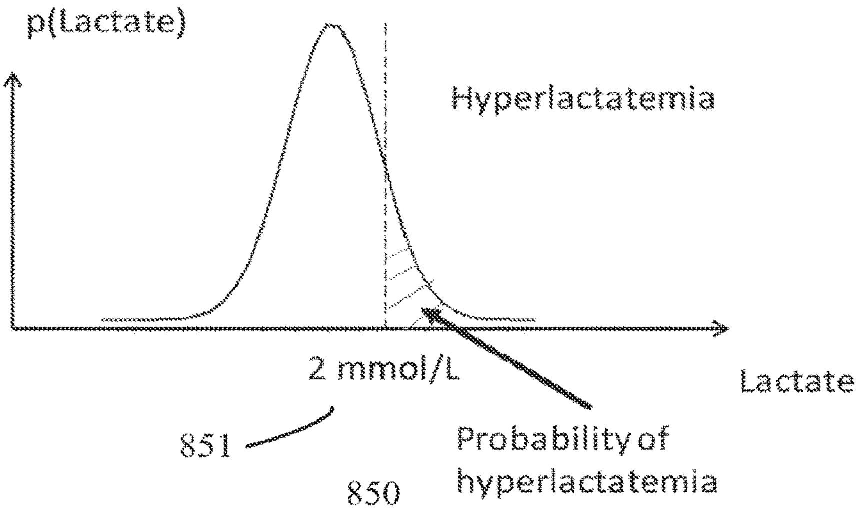

FIG. 8E illustrate the evaluation of the state of Hyperlactatemia based on the ISV of whole blood Lactate. As a non-limiting example the probability 850 of this state is computed as the cumulative distribution of whole blood Lactate [p(Lactate)] being above a 2 mmol/L threshold, or in some embodiments, a 4 mmol/L threshold. The resulting Clinical Risk can be displayed as an index whose instantaneous time value is given by:

$$LA\ \text{Index} = P\left(\text{Lactate} < 4\frac{mmol}{L}|M(t_k)\right) = \int_{-\infty}^{4} P(\text{Lactate}|M(t_k))d\ \text{Lactate}$$

Figure 8F:
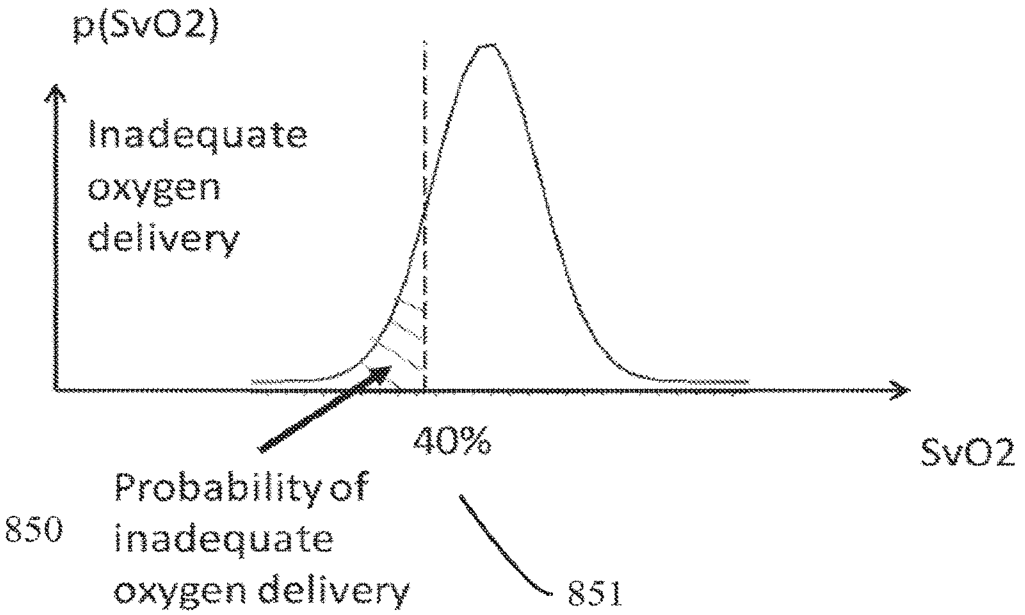

FIG. 8F illustrate the evaluation of the state of Inadequate Oxygen Delivery based on the ISV of mixed venous oxygen saturation (SvO2). As a non-limiting example the probability 850 of this state is computed as the cumulative distribution of p(SvO2) less than a 40% threshold. The resulting Clinical Risk can be displayed as an index whose instantaneous time value is given by:

$$\text{IDO2Index} = P(\text{SvO2} < 40\%|M(t_k)) = \int_{-\infty}^{40} P(\text{SvO2}|M(t_k))d\text{SvO2}$$

Figure 8G:
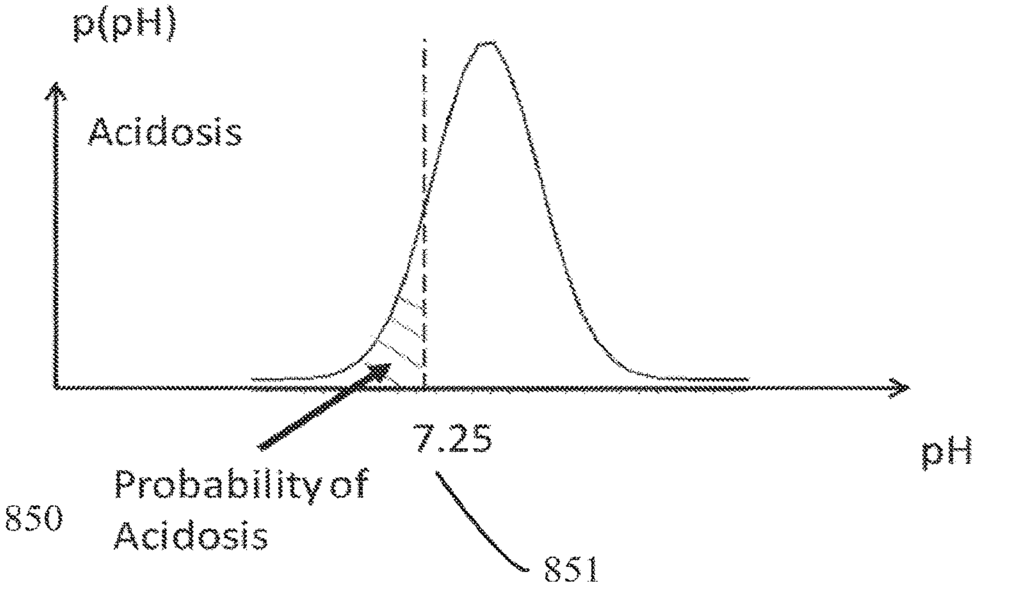

FIG. 8G illustrate the evaluation of the state of Acidosis based on the ISV of pH of arterial blood. As a non-limiting example the probability of this state is computed as the cumulative distribution of arterial pH [p(pH)] less than a 7.25 threshold. The resulting Clinical Risk can be displayed as an index whose instantaneous time value is given by:

$$\text{AC Index} = P(\text{pH} < 7.25|M(t_k)) = \int_{-\infty}^{7.25} P(\text{pH}|M(t_k))d\text{pH}$$

FIG. 9 illustrates a non-limiting example of a definition of a patient state that may be employed by the clinical trajectory interpreter module 123. Specifically, it assumes that the function $P(S|ISV_1, ISV_2, \ldots, ISV_n)$ may be defined by partitioning the domain spanned by the internal state variables $ISV_1$, $ISV_2$, . . . , $ISV_n$. The particular example assumes that the patient physiology is described by two internal state variables: Pulmonary Vascular Resistance (PVR) and Cardiac Output (CO). The particular risks and respective etiologies that may be captured by these two ISVs emanate from the effects of increased pulmonary vascular resistance on the circulation. Specifically, high PVR may cause right-heart failure and consequently reduced cardiac output. Therefore, PVR can be used to define the attributes of Normal PVR and High PVR, and CO to define the attributes of Normal CO and Low CO, by assigning thresholds with the two variables. By combining these attributed, four separate states can be defined: State 1: Low CO, Normal PVR; State 2: Low CO, High PVR; State 3: Normal CO, High PVR; State 4: Normal CO Normal PVR.

FIG. 10 illustrates a non-limiting example of how the clinical trajectory interpreter module 123 may employ the definition of patient states to assign probabilities that the patient may be classified under each of the four possible patient states at a particular point of time. In the example, the clinical trajectory interpreter module 123 takes the joint probability density function of P(Cardiac Output (Tk), Pulmonary Vascular Resistance (Tk)) and integrates it over the regions corresponding to each particular state, which produces P(S1(Tk)), P(S2(Tk)), P(S3(Tk)), and P(S4(Tk)). In this way, the clinical trajectory interpreter module 123 assigns a probability that a particular patient state is ongoing, given the information provided by the physiology observer module 122. Note that if the output of the physiology observer module 122 is not a closed form function 260 but a histogram 280 of particles 270, the clinical interpreter will not perform integration but just calculate the relative fraction of particles 270 within each region.

FIG. 11 illustrates an alternative approach of estimating the probabilities for different patient states. In this alternative approach, to calculate the probabilities P(S1), P(S2), P(S3) and P(S4), the clinical trajectory interpreter module 123 employs the joint probability functions of the ISVs for two consecutive time windows $T_k$ and $T_{k+1}$ to calculate a moving window average. Note in the example that the size of the window is doubled for two time instances, which indicates that the window may be of an arbitrary, suitable size. As a result of this moving window averaging, the clinical trajectory interpreter module 123 performs a dynamic analysis of the trajectory of the ISVs. That is, it gives a metric of the probability that the physiology trajectory, as described by the ISVs, may be found in a particular region in a particular time frame. In other words, this probability calculation gives an estimate of the probability that a particular patient state may be ongoing in the chosen time-frame, as opposed to just at a chosen time instance.

Figure 12:
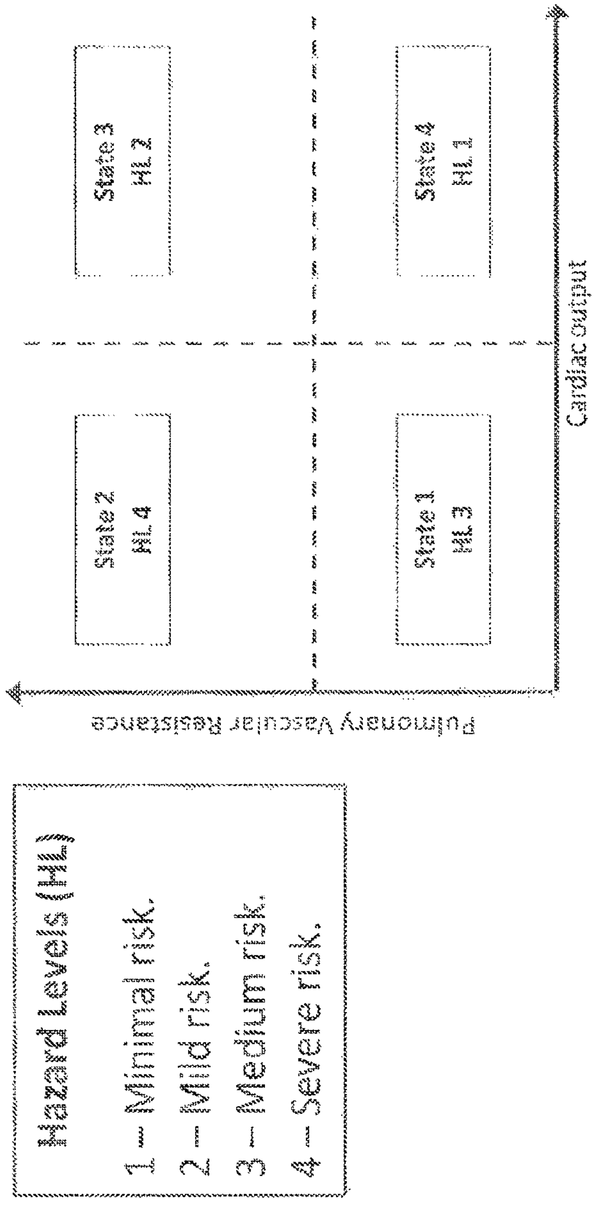
FIG. 12 illustrates conceptually a non-limiting example of a definition of patient states assigned with hazard levels by the clinical trajectory interpreter module in accordance with the disclosure.

Clinical trajectory interpreter module 123 may also assign hazard levels to each particular state. FIG. 12 illustrates a non-limiting example of a definition of patient states assigned with hazard levels by the clinical trajectory interpreter module 123. The hazard levels may be informed from clinician surveys, reference literature or any other clinical sources. In the particular example, the clinical trajectory interpreter module 123 distinguishes between four different hazard levels: 1—Minimal risk, 2—Mild risk, 3—Medium risk, and 4—Severe risk. The combination of the probability of a patient state and its hazard level will be referred from hereon as a "Patient risk."

Figure 13:
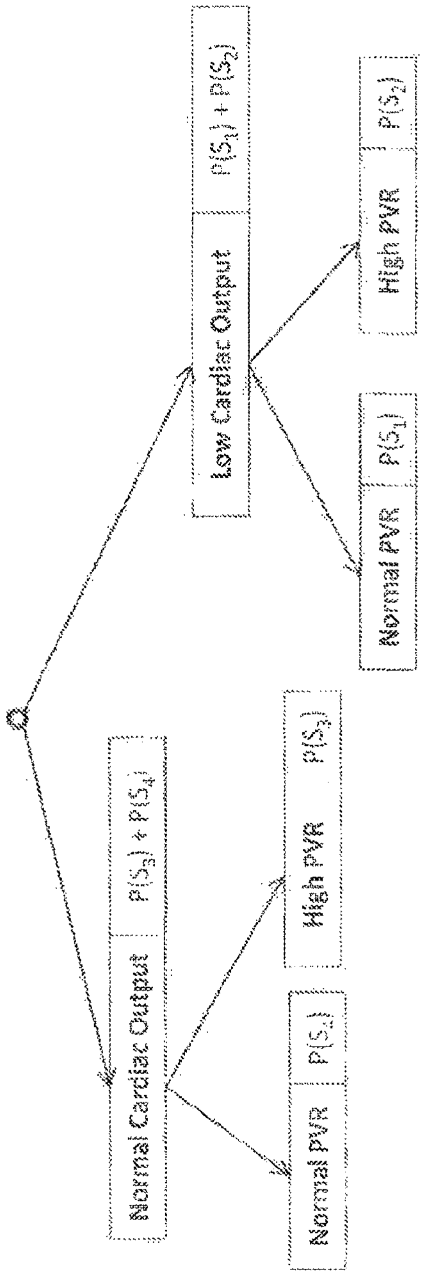
FIG. 13 illustrates conceptually patient states and their respective probabilities organized into tree graphs called etiologies in accordance with the disclosure.

FIG. 13 illustrates how the patient states and their respective probabilities may be organized into tree graphs called etiologies. In particular, the attributes normal and low associated with the cardiac output ISV are the base nodes of the graph. Each of these vertexes has two children associated with the attributes of the pulmonary vascular resistance. This organization leads to each patient state being a leaf (end vertex) on the tree. This particular tree will be referred to as an etiology tree. The etiology tree may be further employed by the visualization and user interaction module 124 to provide a layered view of the various patient risks as further described herein.

Figure 14:
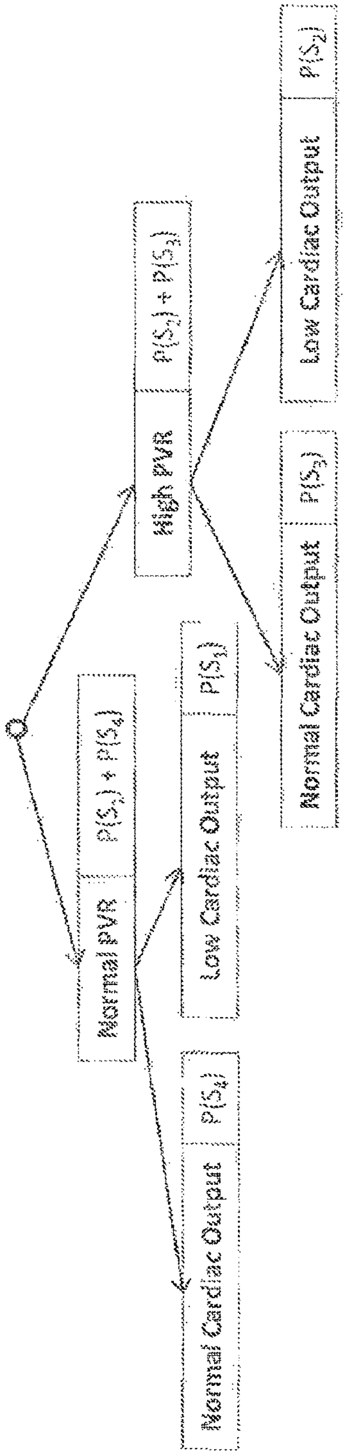
FIG. 14 illustrates conceptually an exemplary etiology tree for a given set of patient states and physiologic variables in accordance with the disclosure.

FIG. 14 illustrates that the etiology tree may not be unique for a given set of patient states and physiologic variables. Specifically, FIG. 14 provides an alternative etiology tree for the example from FIG. 13. The root of the alternative etiology tree starts from the attributes associated with the pulmonary vascular resistance, instead of the attributes associated with cardiac output. It can be appreciated that different rules may be employed for generating the trees depending on various factors and the context of use. For example, one etiology tree may be preferred against another realization in different clinical situations or depending on the preference of the users. Moreover, the tree may dynamically change as the risks change and the clinical situation evolves.

Utility of Different Measurements

Figure 15:
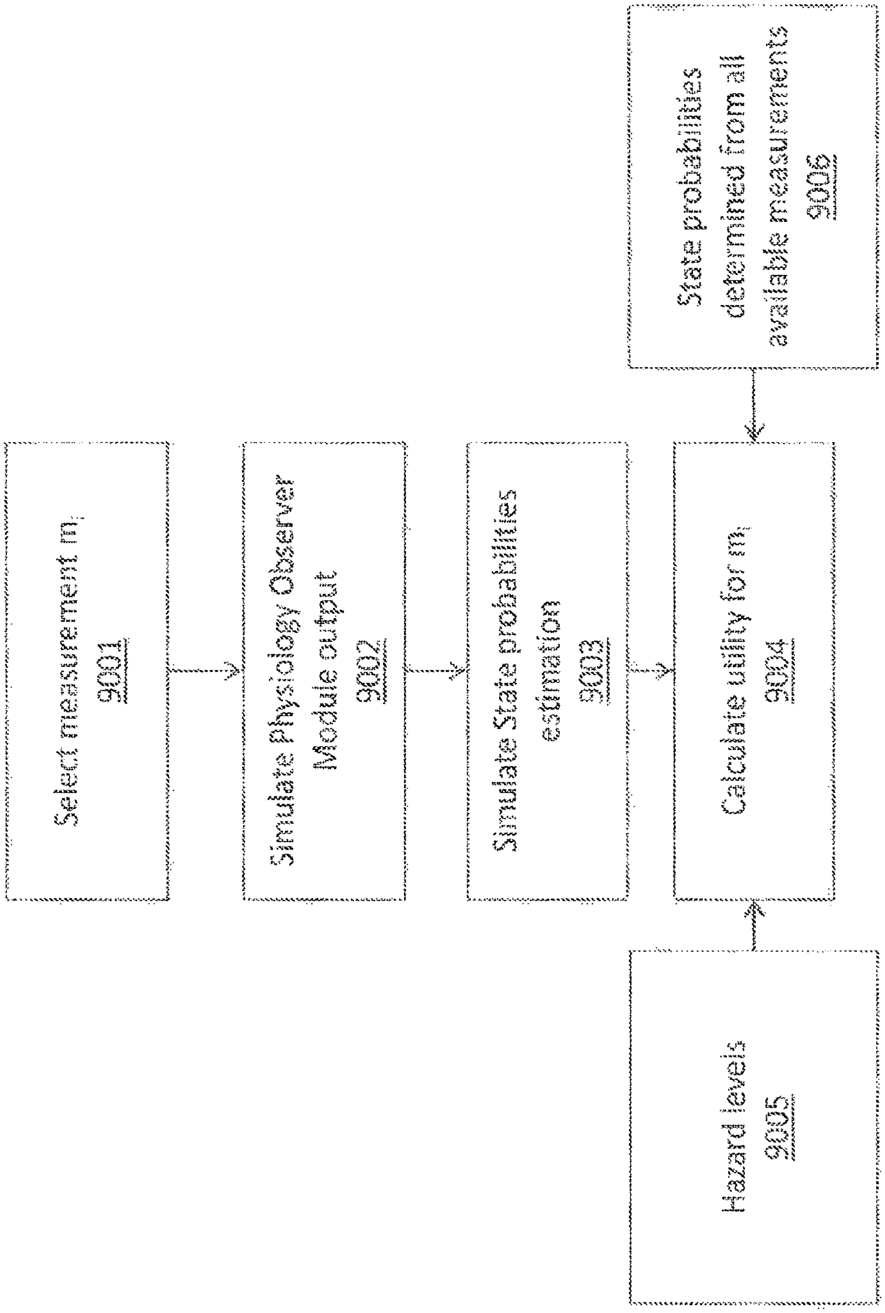
FIG. 15 illustrates conceptually a method for calculating the utility of different measurements in accordance with the disclosure.

During hospital care, there exist measurements that may harm the patient or slow down their recovery. Examples of such harmful measurements are all measurements coming from catheters such as invasive blood pressures and blood oximetry, which have been shown to significantly increase the risk of infection. Therefore, it may be useful if, during the care process, the clinician is provided with an assessment of the utility of each of the potentially harmful measurements. FIG. 15 illustrates a method for calculating the utility of different measurements.

Referring to FIG. 15, the risk-based system 100 and the clinical trajectory interpreter module 123 may calculate the utility of a particular measurement with the illustrated procedure. Particularly, in step 9001, a measurement $m_i$ may be selected. Given measurement $m_i$ and a current time ($t_{current}$), in step 9002, the clinical trajectory interpreter module 123 may submit an instruction to the physiology observer module 122 to simulate the physiology observer module output (the probability density functions of the internal state variables) from a given arbitrary point back from the current time ($t_{current}-T$) to the current time $t_{current}$ with removal of measurement $m_i$ from the algorithm output. Then, in step 9003, the clinical trajectory interpreter module 123 may simulate the state probabilities estimation given the simulated output of the physiology observer and arrive with a set of patient state probabilities, i.e., $P_{sim}(S_1(t_{current}))$, $P_{sim}(S_2(t_{current}))$, . . . , $P_{sim}(S_n(t_{current}))$. Then, in step 9004, using the state probabilities determined from all available measurements, i.e., $P(S_1(t_{current}))$, $P(S_2(t_{current}))$, . . . , $P(S_n(t_{current}))$, the clinical trajectory interpreter module 123 may calculate the utility of the measurement $m_i$ using the formula:

$$U(m_i) = D(P_{sim}|P) = \sum_{i=1}^{n} P(S_i(t_{current}))\log\left(\frac{P(S_i(t_{current}))}{P_{sim}(S_i(t_{current}))}\right),$$

which is also the Kullback-Leibler divergence between the patient state distribution given all available measurements and the patient state distribution given the measurement $m_i$ has been removed for a time interval T.

Alternatively, in step 9005, the clinical trajectory interpreter module 123 may calculate utility for $m_i$ by employing the hazard levels, $r_i$, assigned to each state $S_i$ by the formula:

$$U(m_i) = D_{weighted}(P_{sim}|P) = \sum_{i=1}^{n} r_i P(S_i(t_{current}))\log\left(\frac{P(S_i(t_{current}))}{P_{sim}(S_i(t_{current}))}\right).$$

In a similar manner, the clinical trajectory interpreter module 123 can perform the utility calculation not only for a particular measurement, but also for any group of measurements. The utility calculation can also include a component that captures the potential harm associated with a particular measurement. For example, the invasive catheter measurement described above would have a large level of harm associated with it. In this way, the calculation trades the harm associated with the measurement against the value of information it provides. An example of this modified utility calculation is given by the following formula:

$$U(m_i)=D_{weighted}(P_{sim}|P)-H(m_i),$$

where $H(m_i)$ defines a function that describes the harm of each available measure.

Figure 16:
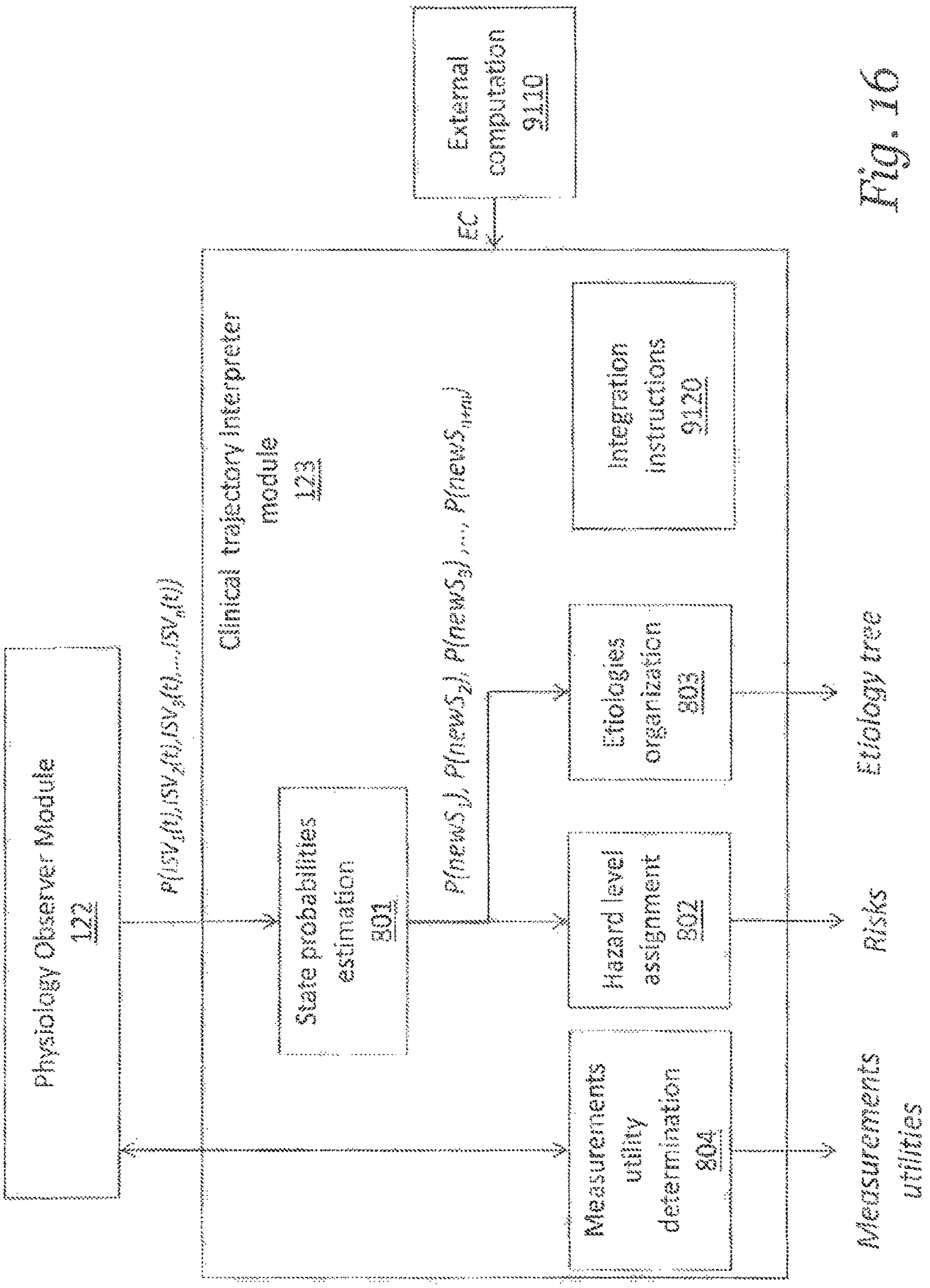
FIG. 16 illustrates conceptually one possible realization of integration of external computation generated from third party algorithms in accordance with the disclosure.

The risk-based monitoring system 100 can also integrate external computation generated from third party algorithms implemented either on the same computation medium as the patient-based monitoring system or as a part of an external device. FIG. 16 illustrates one possible realization of integration of an external computation generated from third party algorithms. Particularly, the output from the external computation 9110 is provided to the clinical trajectory interpreter module 123 which implements integration instructions 9120. As a result the state probability estimation 801 produces new states $P(newS_1)$, $P(newS_2)$, $P(newS_3)$, . . . , $P(newS_{n+m})$, which may result in an increased number of states n+m from the original number of n states. Similarly, integration instructions 9120 may be provided to the hazard level assignment 802 and the etiology organization 803.

Figure 17:
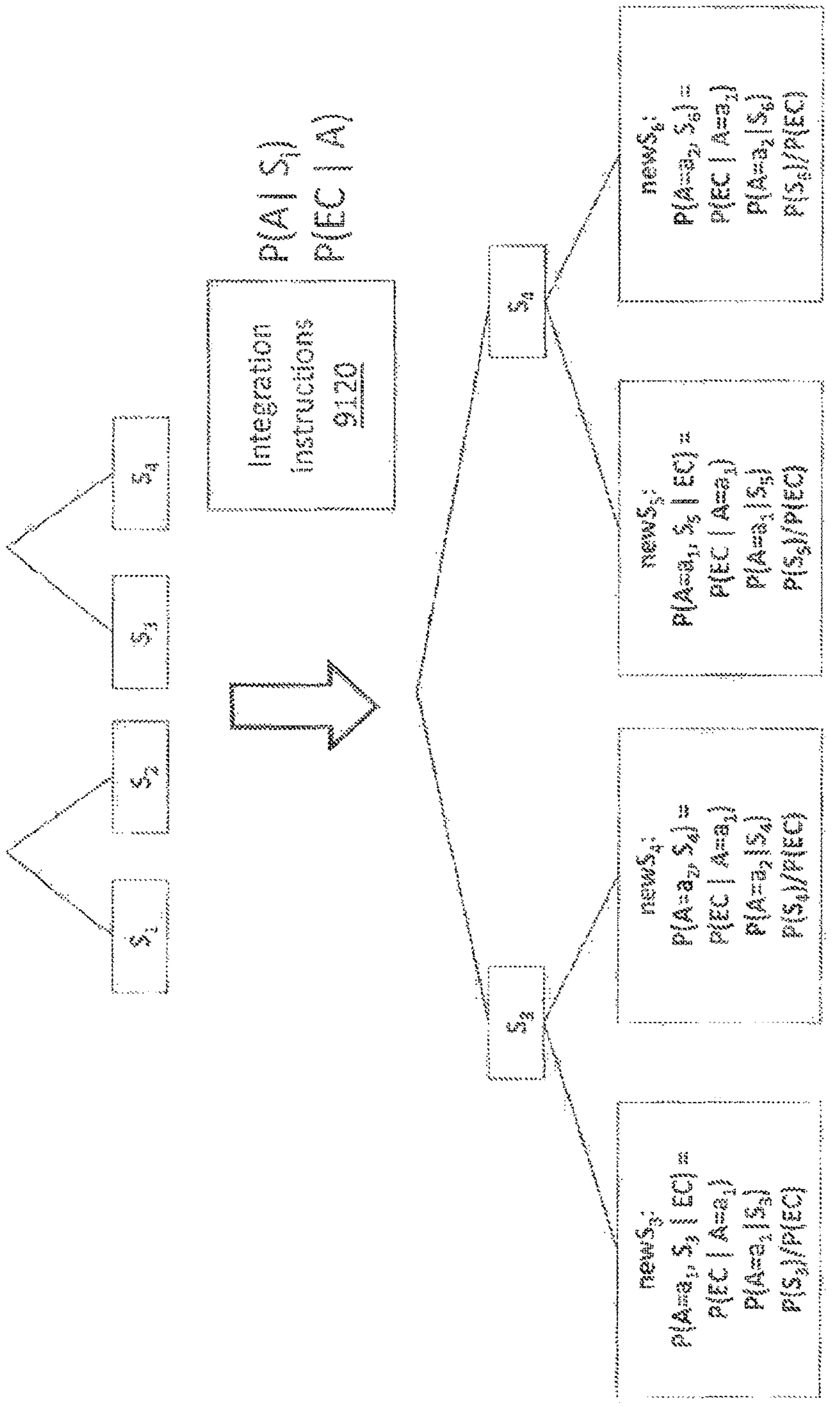
FIG. 17 illustrates conceptually an example of integration instructions of an external computation in accordance with the disclosure.

FIG. 17 illustrates an example of integration instructions. In the example, it is assumed that the external computation, EC, provides information about particular binary attributes $A=a_1$ or $A=a_2$, and the specific of how the provided information is captured in the integration instructions by the conditional probability P(EC|A). Also, given four original states $S_1$, $S_2$, $S_3$, and $S_4$, the integration instruction may specify how the states $S_3$ and $S_4$ may be updated with two additional attributes $A=a_1$ and $A=a_2$, and turn into four new states $newS_3$, $newS_4$, $newS_5$, and $newS_6$. To perform this update, the integration instruction may also employ prior probabilities $P(A|S_3)$ and $P(A|S_4)$. These prior probabilities may be derived from retrospective studies by analyzing what fractions of patients exhibiting $S_3$ or $S_4$ have concomitantly exhibited $A=a_1$ or $A=a_2$.

Another way to derive the prior probabilities is by soliciting the opinion of clinicians.

By utilizing the integration instructions, the state probabilities estimation 801 of the new states may then be derived from the formula:

$$P(A=a_j,S_i|\mathrm{EC})=P(\mathrm{EC}|A=a_j)P(A=a_j|S_i)P(S_j)/P(\mathrm{EC}),$$

where i in {3,4} and j in {1,2}, and where $P(S_j)$ are the original patient state probabilities derived from the output of the physiology observer module 122.

Figure 18:
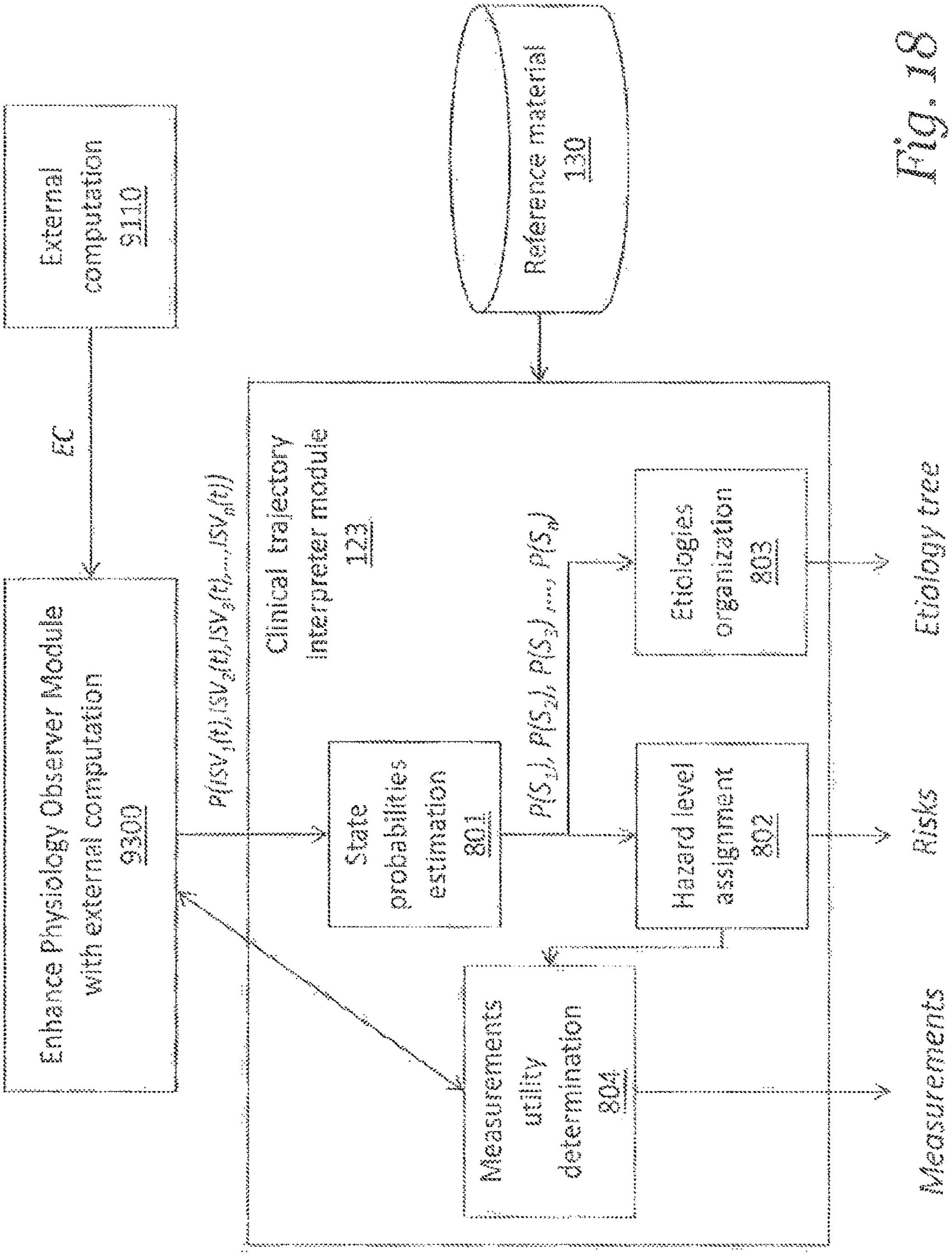
FIG. 18 illustrates conceptually an additional example of integration instructions of an external computation in accordance with the disclosure.

FIG. 18 illustrates an additional example of integration instructions of an external computation. Again, the risk-based monitoring system 100 can perform the integration, as shown in FIG. 18, both in the case that the external computation 9110 is generated on the same computational medium as the patient-based monitoring system, or as a part of an external device. In this case, it is assumed that the external computation 9110 provides direct information about a particular internal state variable estimated by the physiology observer module 122 (or enhanced physiology observer module 9300). Therefore, to integrate the external computation, the physiology observer module 122 can treat the external computation 9110 as an additional measurement and integrate it directly into the observation model 221.

Visualization and User Interaction

Figure 19:
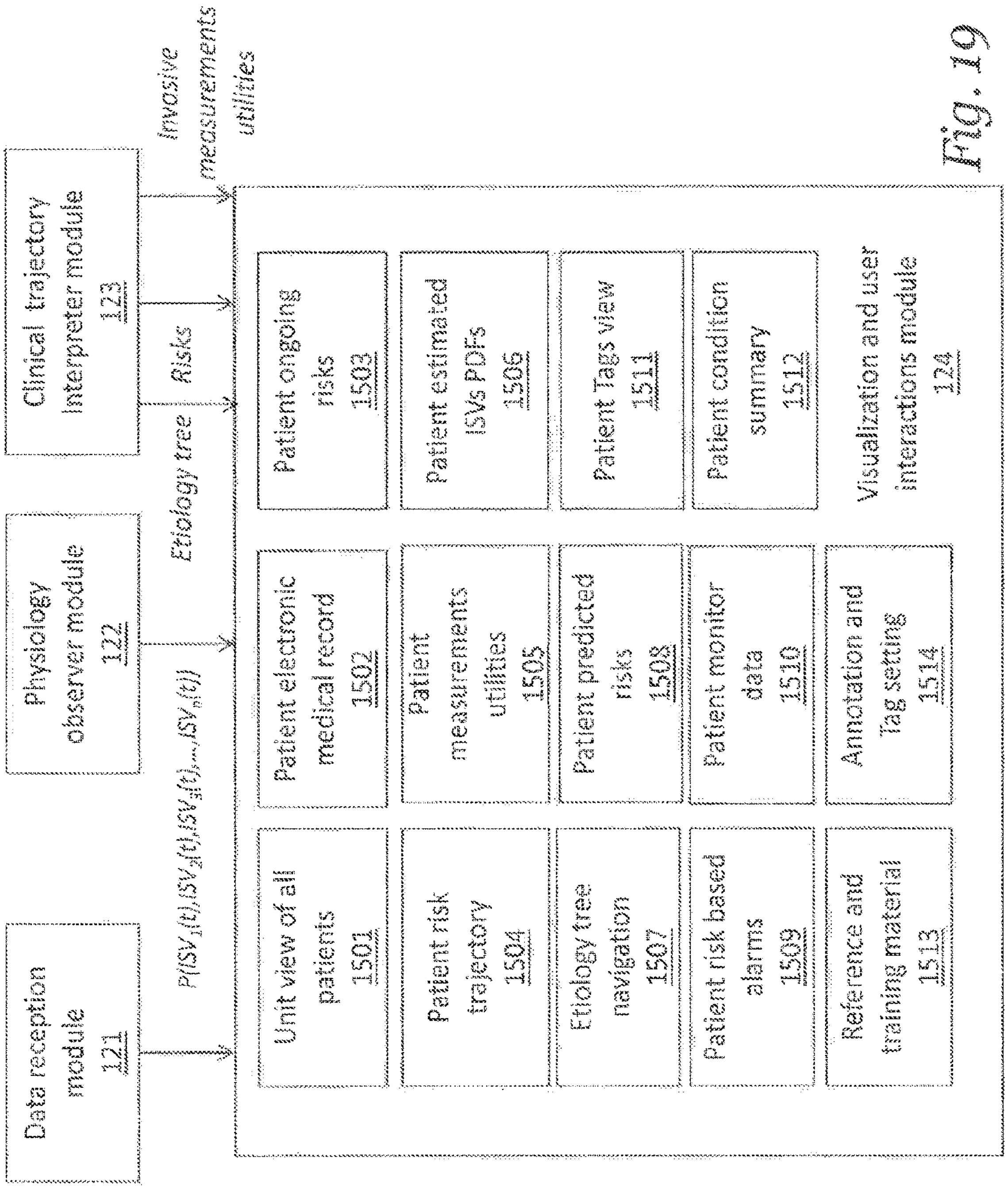
FIG. 19 illustrates conceptually example functionalities of the visualization and user interactions module in accordance with the disclosure.

FIG. 19 illustrates example functionalities of the visualization and user interactions module 124. Specifically, module 124 may receive all available patient information and data including, the data from the data reception module 121, the joint probability density function produced by the physiology observer module 122, and the etiology tree, the risks, and the invasive measurements utilities estimated by the clinical trajectory interpreter module 123. By utilizing this information, the visualization and user interactions module 124 may produce: 1) a unit view 1501 of patients describing their risks, diagnoses, etc.; 2) a view 1502 of a patient's electronic medical record including laboratory results, prescribed medication, diagnoses, etc.; 3) a view 1503 of a patient's ongoing risks; 4) a view 1504 of a patient's risk trajectory, i.e., how the probabilities for particular patient states have evolved in a particular time frame; 5) a view 1505 of a patient's measurements utilities in the estimation of the particular patient risks; 6) a plot of a patient estimated ISVs' PDFs 1506 describing the time evolution of the ISVs' PDFs; 7) a view 1507 enabling to navigate through the etiology tree of the patient and thus visualize different levels of the tree; 8) a view 1508 showing a patient's predicted risks; 9) a view 1509 enabling clinicians to view and set patient risk based alarms; 10) a view 1510 of a patient's physiology monitoring data and its evolution against time; and 11) any combination of the above described. In addition, the visualization and user interactions module 124 may also produce a patient tags view 1511, a patient condition summary 1512, reference and training material 1513, and annotation and tag setting 1514.

Figure 20:
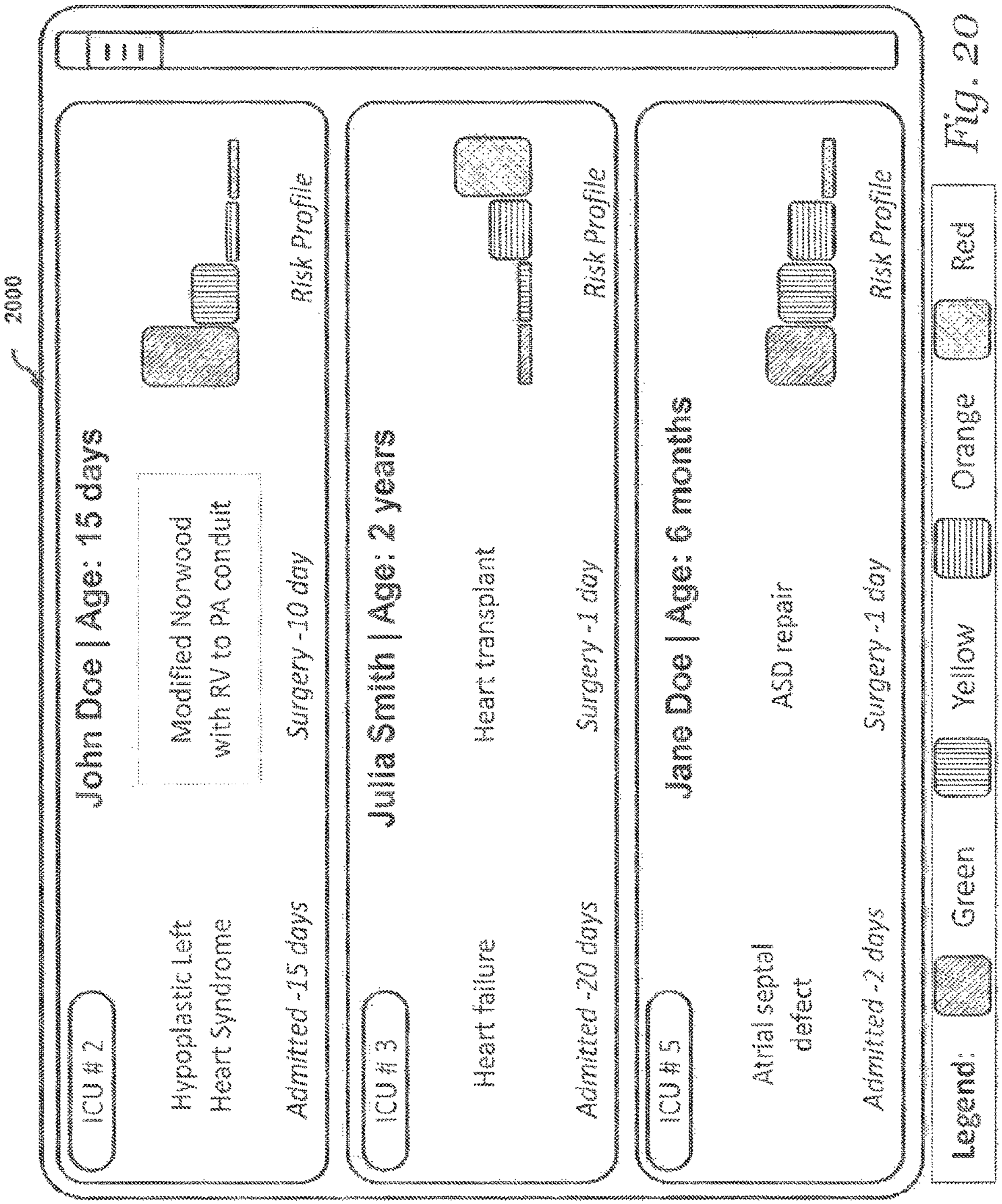
FIG. 20 illustrates conceptually an example of a summary view that may convey on a single screen a risk profile for each patient in a particular hospital unit in accordance with the disclosure.

FIG. 20 illustrates an example of a summary view 2000 that may convey in a single screen a risk profile for each patient in a particular hospital unit. The risk profile represents what is the cumulative probability of the patient being in a particular hazard level. It is calculated by summing the current probabilities of all states at particular hazard level. In the example, the summed probabilities, hazard levels are represented by the height of four bars, each bar corresponding to a particular hazard level. In this specific example, these hazard levels may be Green (slanted hatching)—Minimal risk, Yellow (vertical hatching)—Mild risk, Orange (horizontal hatching)—Medium risk, and Red (dotted hatching)—Severe risk.

Figure 21:
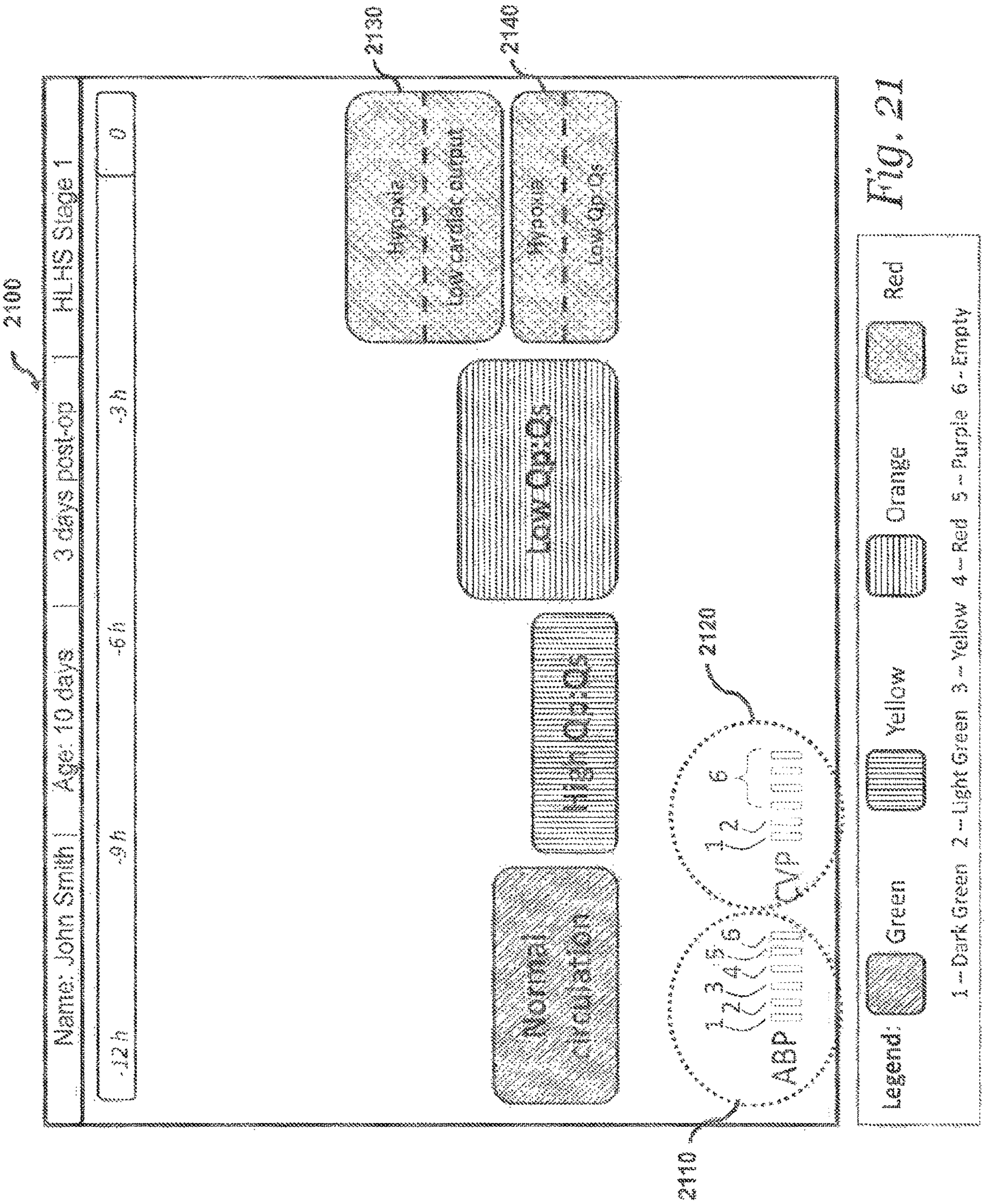
FIG. 21 illustrates conceptually one possible realization of a view describing the ongoing risks of the patient in accordance with the disclosure.

FIG. 21 illustrates one possible realization of a view 2100 describing the ongoing risks of the patient. Each round-cornered box corresponds to a particular risk: the color corresponds to the hazard level with Green (slanted hatching)—Minimal risk, Yellow (vertical hatching)—Mild risk, Orange (horizontal hatching)—Medium risk, and Red (dotted hatching)—Severe risk; the height of the box corresponds to the probability of the particular patient state. Risks are grouped in columns based on their hazard levels. The screen and the respective risks are updated in real-time as new data becomes available.

Still referring to FIG. 21, in addition to the visualization of the ongoing patient risks, the system 100 may provide information about the utility of the various invasive measurements in determining these risks. Specifically, the illustrated example gives the utilities of invasive arterial blood pressure (ABP) and invasive central venous pressure (CVP) measurements. The utility may be represented by filled bars 2110 and 2120, and the maximum utility may correspond to six filled bars. The six filled bars may be displayed in color gradient from 1-dark green, 2-light green, 3-yellow, 4-red, 5-purple, to 6-white or empty. In this particular embodiment, the filled bars 2110 for ABP show all six colors, while two of the filled bars 2120 for CVP respectfully show 1-dark green and 2-light green and the remaining filled bars 2110 show 6-white or empty.

Figure 22:
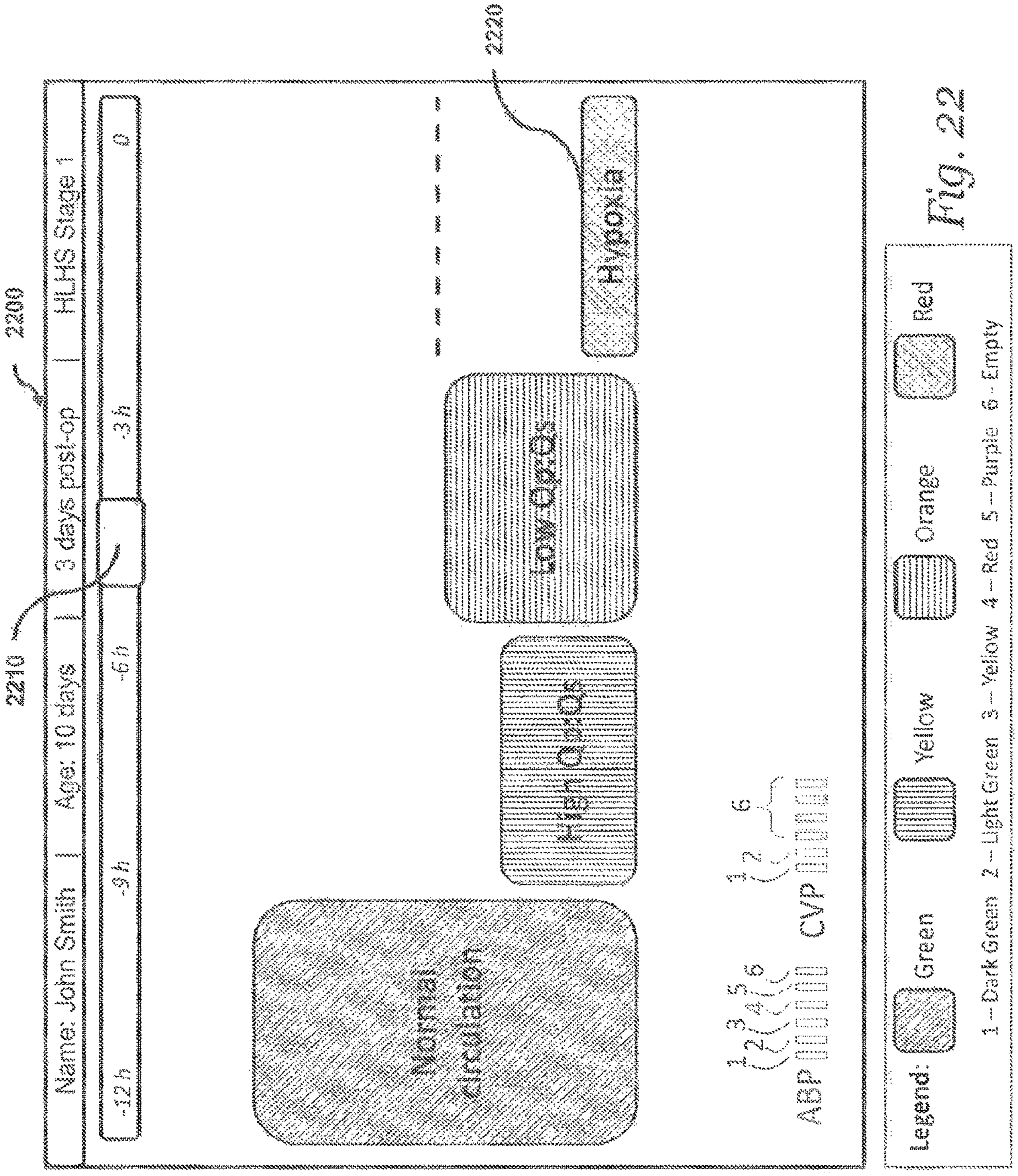
FIG. 22 illustrates conceptually how the slider on top of the patient view may be utilized in reviewing the history of the patient risks in accordance with the disclosure.

FIG. 22 illustrates a view 2200 and how a slider 2210 or other graphic element on top of the patient view may be utilized in reviewing the history of the patient risks. Specifically, in the example, the slider 2210 is moved to show the patient risks at approximately four hours back from current time. This enables clinicians to review the continuous evolution of the patient risks and compare them with the applied treatment or any other external factors. In various embodiments, slider 2210 may be moved on the user interface with a pointing device, a command, or, if utilized in conjunction with touch sensitive displays, through touching and dragging the slider or other graphic element to designate the desired time period.

Figure 23:
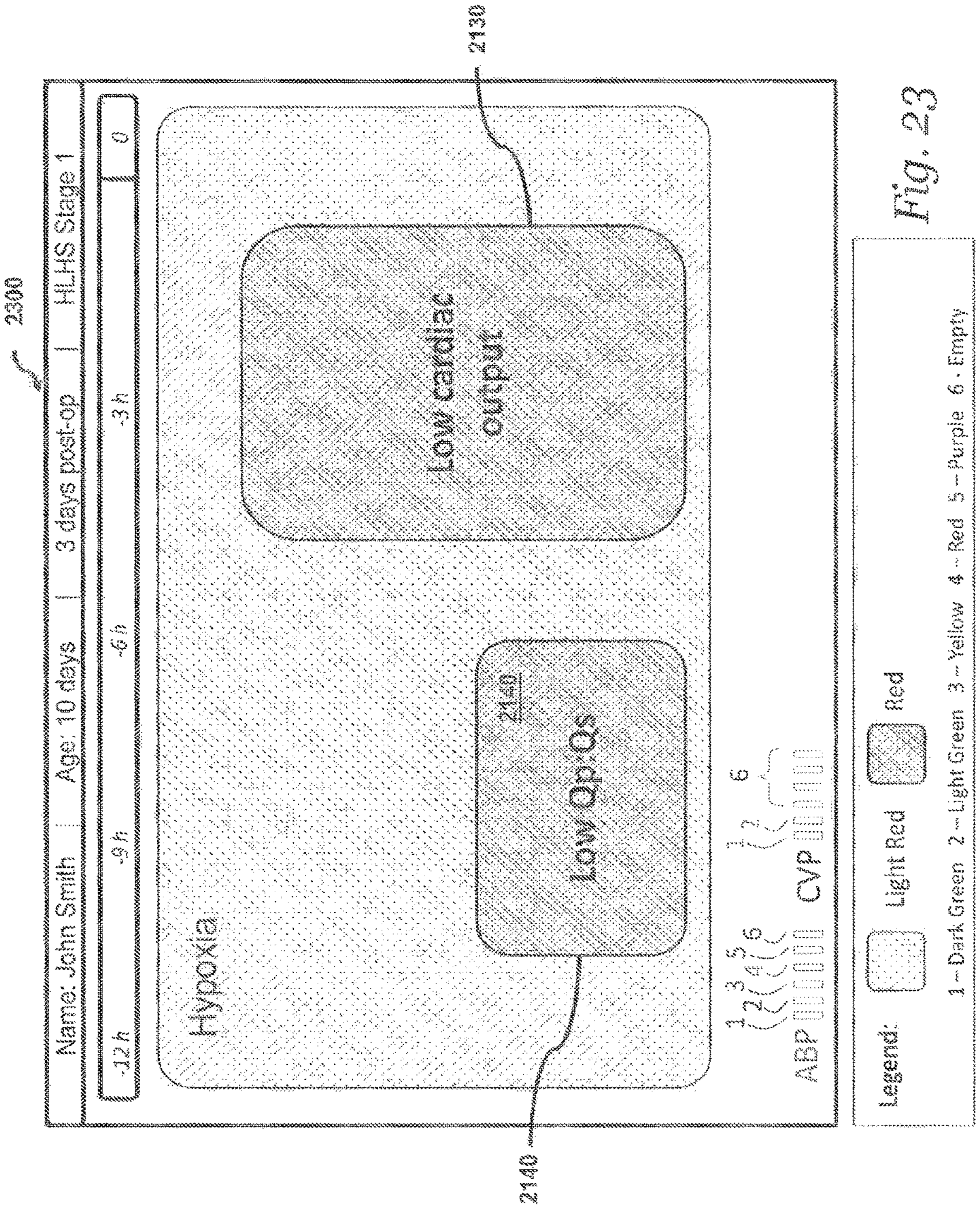
FIG. 23 illustrates how the user can navigate the etiology tree by clicking on the composite patient state and viewing the constituent patient states in accordance with the disclosure.

Referring now to both FIGS. 21 and 22, the etiology tree is used to combine the two states State A 2130: Hypoxia with low cardiac output and State B 2140: hypoxia with low Qp:Qs from FIG. 21 to represent them by a single patient state (Hypoxia) 2220. In the particular example, this is used to fit the text into the smaller box of FIG. 22 relative to FIG. 21. The user can navigate the etiology tree in view 2300 by clicking on the composite patient state 2220 and viewing its constituent patient states 2130 and 2140, as illustrated in FIG. 23.

Figure 24:
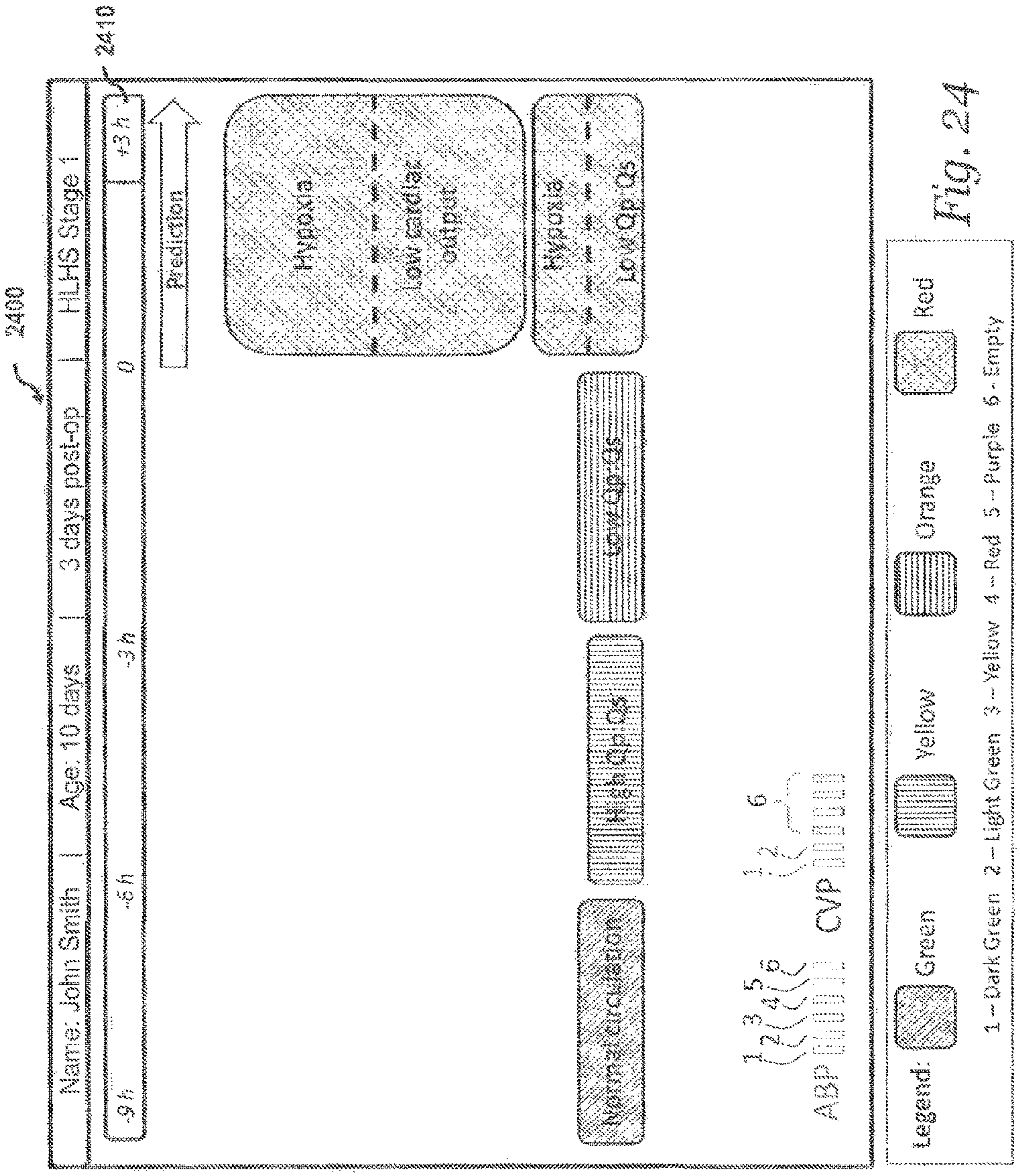
FIG. 24 illustrates conceptually how in the same framework the user may view the predicted risks for the patient by sliding the slider ahead of current time in accordance with the disclosure.

FIG. 24 illustrates in view 2400 how in the same framework the user may view the predicted risks for the patient by moving the slider 2410 ahead of current time. |[DB3]

Figure 25:
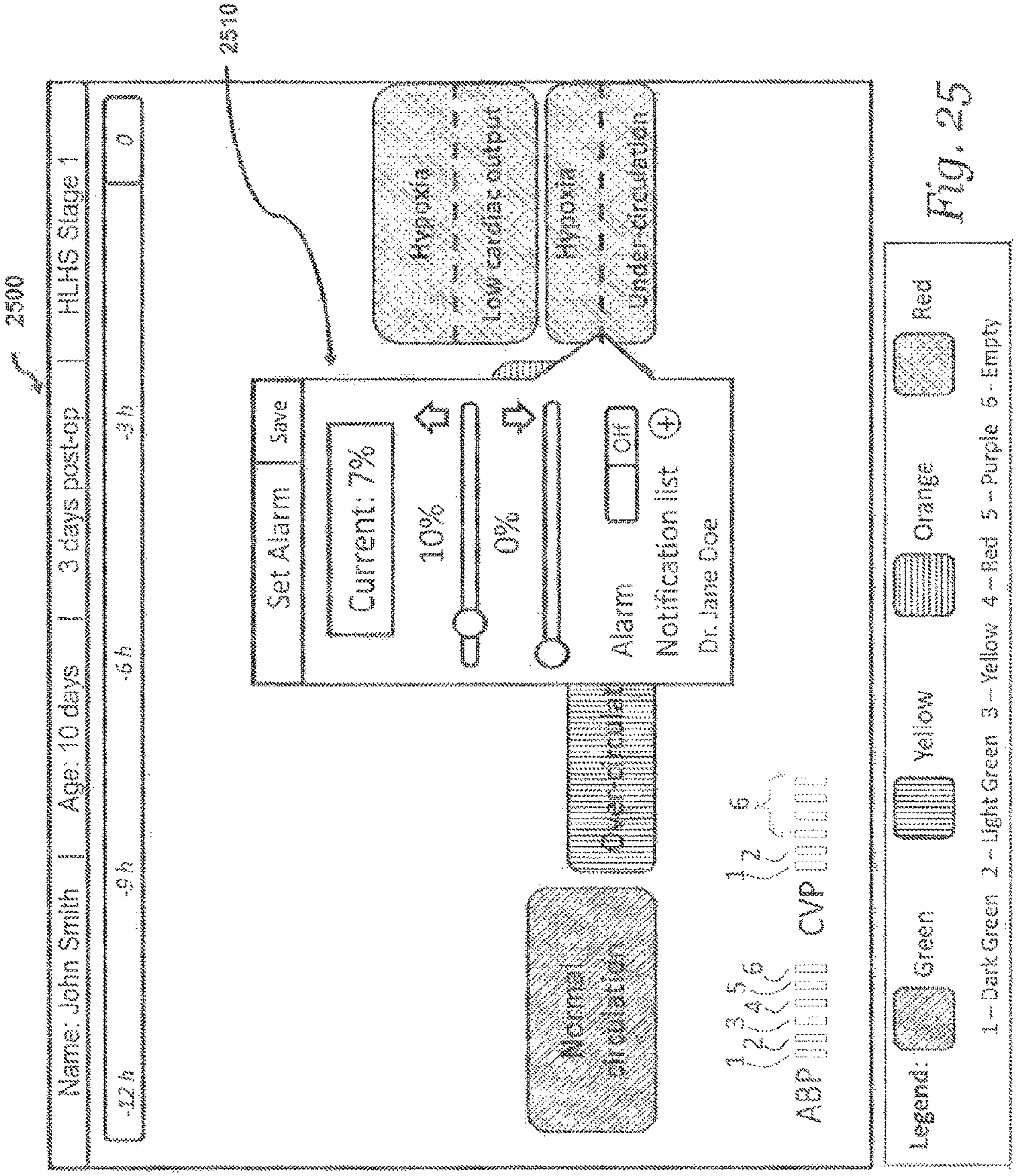
FIG. 25 illustrates conceptually how the user may choose to set an alarm for a particular risk in accordance with the disclosure.

FIG. 25 illustrates in view 2500 an interactive dialog box 2510 through which the user may define the conditions to set an alarm for a particular risk. The user achieves this by selecting the particular risk and then setting upper and lower thresholds for the patient state probability associated with this risk. No alarm is activated as long as the patient state probability is between the upper and the lower threshold. The alarm is activated when the patient state probability crosses the threshold. Once the alarm is activated the system 100 may notify a list of chosen people, or send the notification to another clinical system. Any of module 122-124 may actually store their respective threshold data ranges and initiate the trigger depending on the specific parameter.

Figure 26:
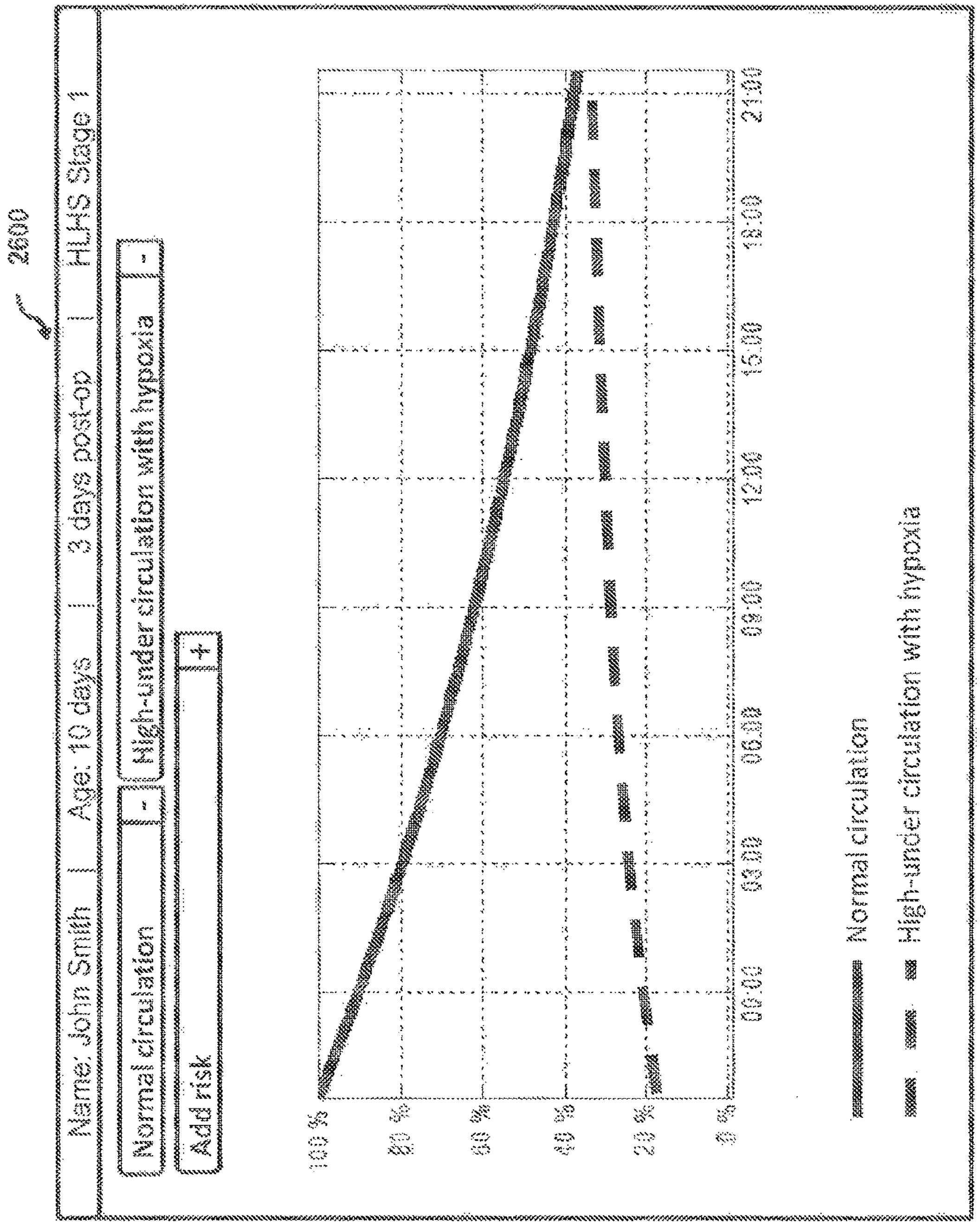
FIG. 26 illustrates conceptually yet another possible visualization of the patient risk trajectory, i.e., the evolution of the patient states' probabilities associated with particular risks in accordance with the disclosure.

FIG. 26 illustrates in view 2600 yet another possible visualization of the patient risk trajectory, i.e. the evolution of the patient states' probabilities associated with particular risks. The user may choose what time series of patient state probabilities he/she wants to display, and the system plots these probabilities against time.

Figure 27:
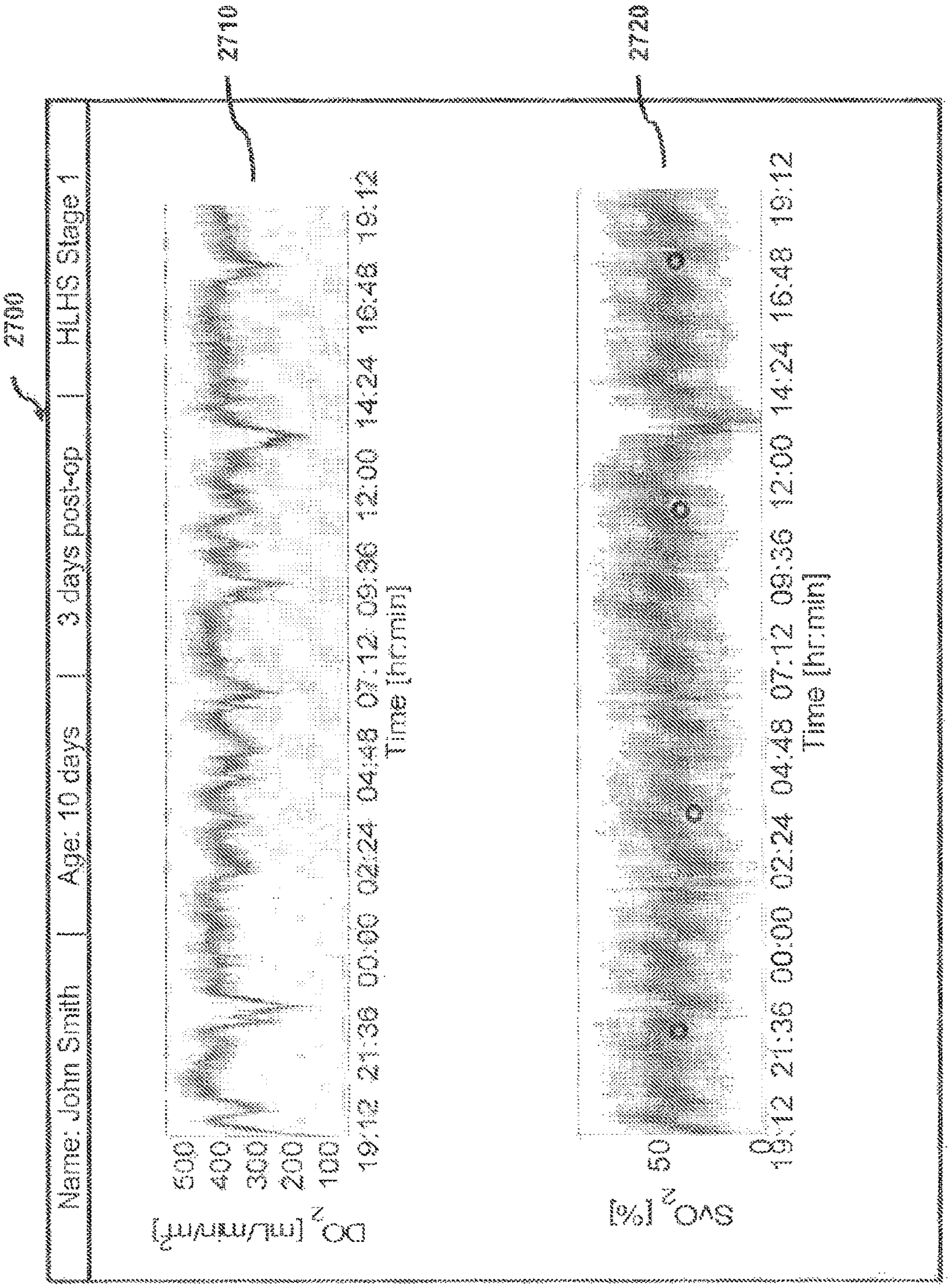
FIG. 27 illustrates conceptually how the system may directly visualize the probability density functions of various internal state variables in accordance with the disclosure.

FIG. 27 illustrates in view 2700 how the system 100 may directly present the probability density functions of various internal state variables. Specifically, in the example, the estimated PDF of oxygen delivery is plotted in graph 2710 as a function of time, with darker colors corresponding to higher likelihood. Similarly, the estimated PDF of mixed venous oxygenation saturation (SvO2) is plotted in graph 2720 and compared with actual measurements (dark circles).

Information Sharing Among Users

Figure 28:
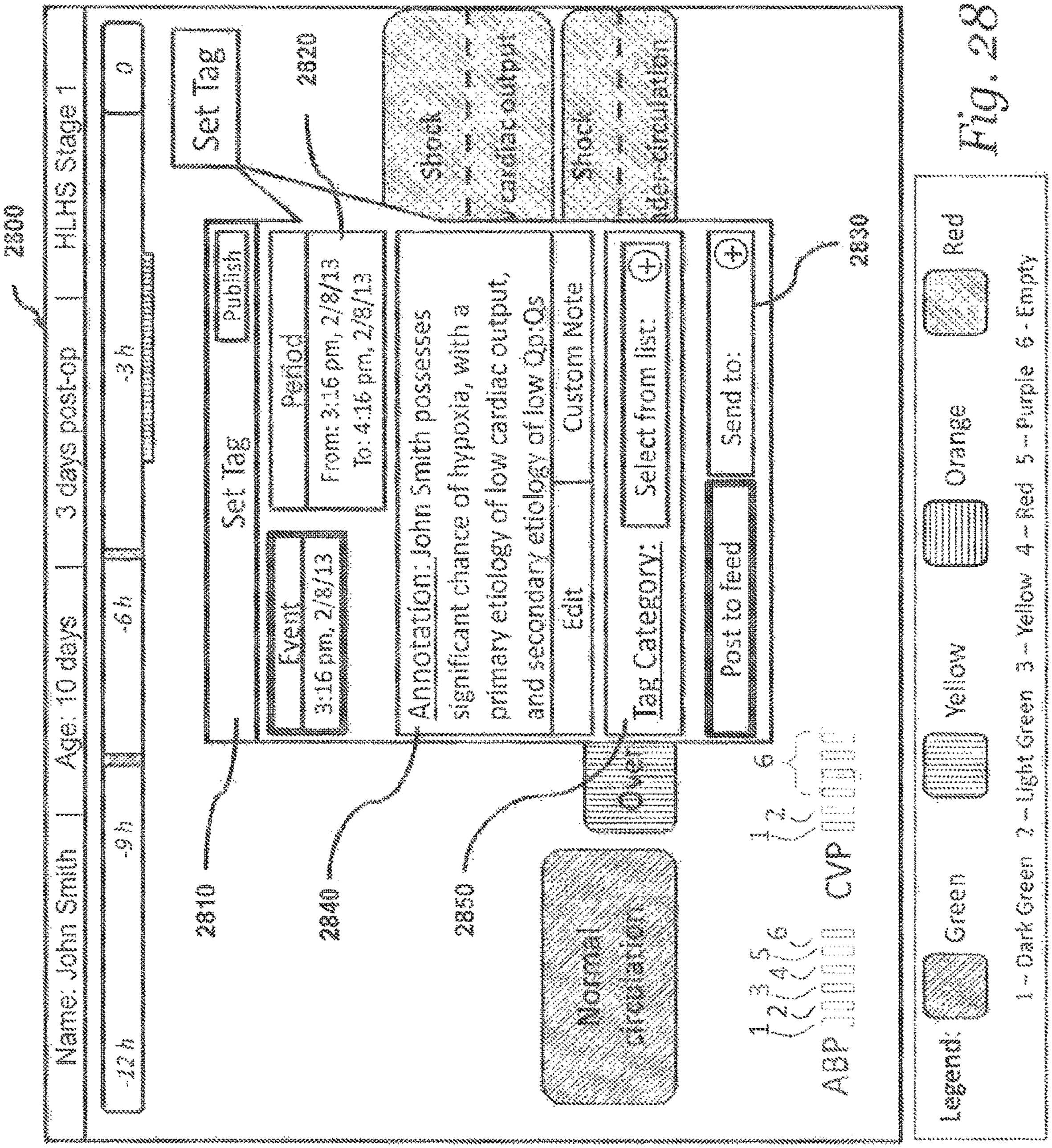
FIG. 28 illustrates conceptually an example of a tagging feature that a user interface may implement in accordance with the disclosure.

FIG. 28 in view 2800 illustrates an example of a tagging definition interface 2810 that enables clinicians to mark specific instances of time or specific periods of time 2820 that are of interest or represent important points in the clinical course, i.e. a tag. Tags may be shared or sent via dialog box 2830 to specified recipients, or may be included in notes or any other part of the user interface. Users may be able to annotate a tag with particular comments or observations via dialog box 2840, and tags may be classified into categories from menu list 2850, for example, a tag may represent a change in medication dosing, an intervention, a note regarding monitors or measuring equipment, etc. Tags and their respective time-series markings may be color coded to indicate various properties, such as their category. For example, green tag-marks on a time series may represent changes in medication, red tag-marks may represent interventions, and yellow tag marks may represent periods of heightened concern. When setting a tag, the user may be prompted to define time instance or the time period, the category of the tag, the annotation for the tag, and how the tag should be handled by the system. Furthermore, annotations may be suggested by using natural language processing to convert the etiologies of the condition into note form.

Figure 29:
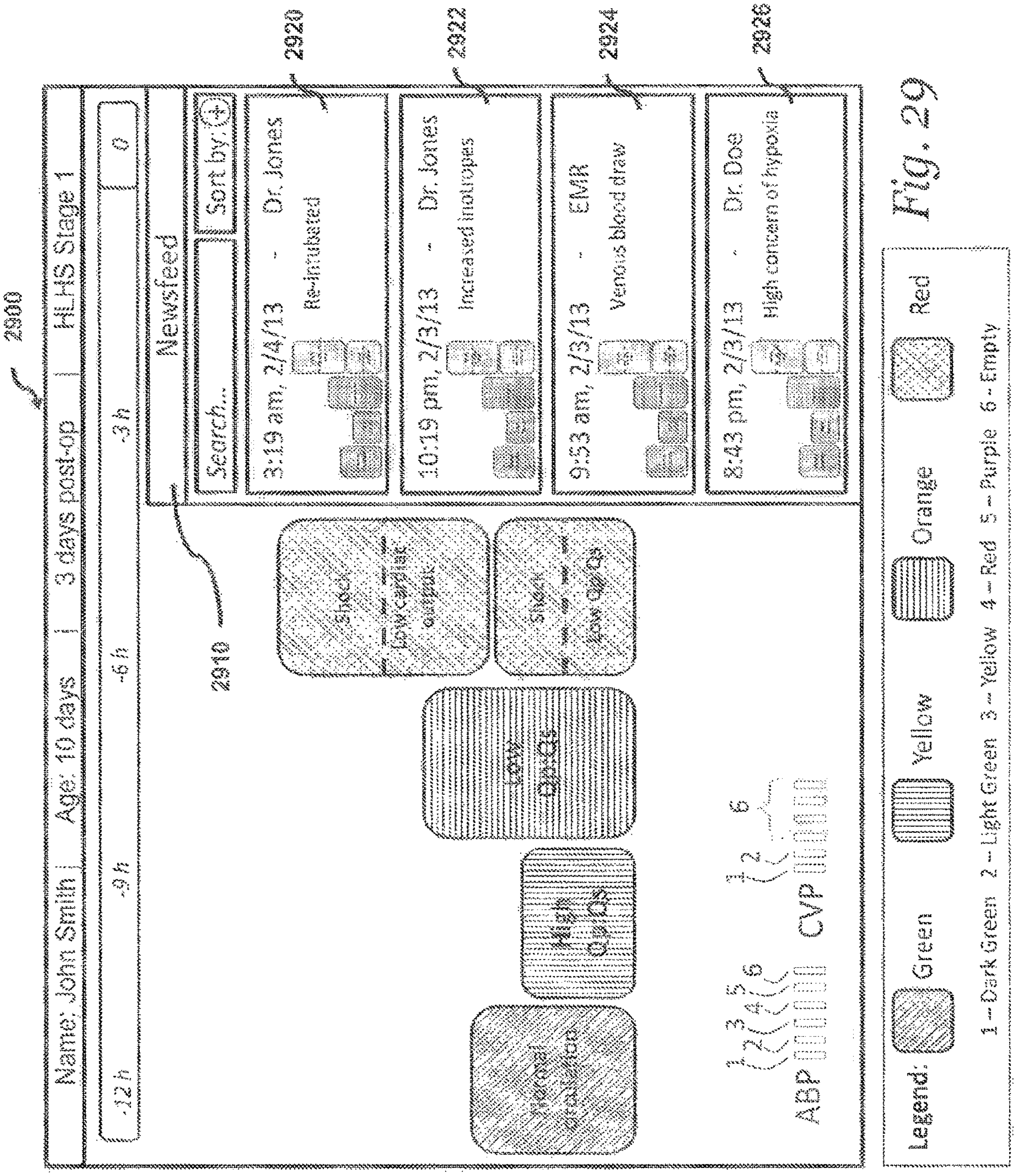
FIG. 29 illustrates conceptually a Newsfeed view of the user interface in accordance with the disclosure.

FIG. 29 illustrates in view 2900 a Newsfeed view 2910 comprising tags, notes, or information taken from external sources, such as the time of a blood draw as taken from an electronic medical record (EMR). The Newsfeed 2910 may allow clinicians to view and post events, periods of interest, interventions, notes, tags, etc., which are posted by other clinicians. Clinicians may view the entire Newsfeed, or sort it based on Tag category, hazard level, etc. Further, clinicians may search for tags based on keywords, intervention type, time of stay, source of information, etc. Entries 2920-2926 on Newsfeed 2010 may indicate any of the category, source of tag, and patient overview, either in words, or as a picture, such as the risk profile.

Figure 30:
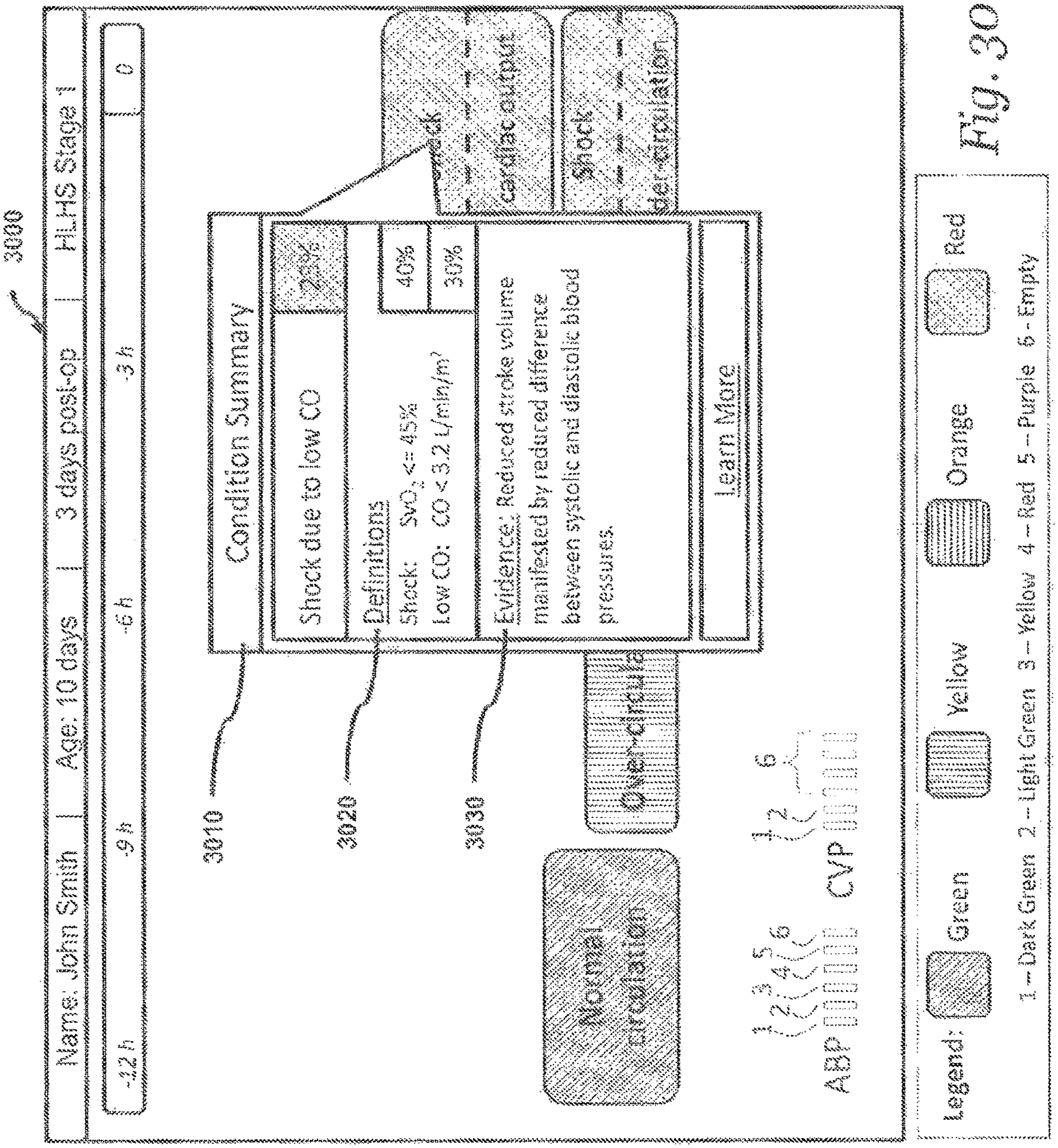
FIG. 30 illustrates conceptually a Condition Summary View of the user interface in accordance with the disclosure.

FIG. 30 illustrates in view 3000 a Condition Summary View 3010 through which the clinician may request a condition summary by selecting or clicking a particular patient state. The Condition Summary View 3010 then may present clinicians with a description of a particular state, including both definitions in window 3020 of the state, and information regarding how the system arrived at the conclusion about this patient state probability. This view 3010 may provide the likelihood and hazard level of the patient state, the definition of the patient state in terms of ISV thresholds, and the likelihood of each attribute defining the state, as illustrated and can also provide a natural language description and evidence window 3030 of evidence contributing to the patient state, by translating the ISVs PDFs into a qualitative textual description, or by directly presenting numerical information regarding the evidence. As an example, FIG. 30 illustrates the Condition Summary View 3010 for the patient state shock due to low cardiac output. Here, the Condition Summary View 3010 presents the probability of the "shock due to low cardiac output" state, and the hazard level of the state shown in color or dotted hatching. Further, the definitions of shock (mixed venous saturation below or equal to 45%), and low cardiac output (cardiac output below 3.2 liters per minute per meter squared), along with the probabilities that each of these are satisfied (e.g., 40% for shock and 30% for low CO) is presented. The evidence window 3030 conveys the information which leads to the assessment of "Shock due to low CO". In this example, the system has converted the information regarding the probabilities of the etiologies into a textual form, specifically that the estimated probability is mainly driven by the fact that there is sub nominal pulse pressure (systolic blood pressure minus diastolic blood pressure) indicating reduced stroke volume.

Figure 31:
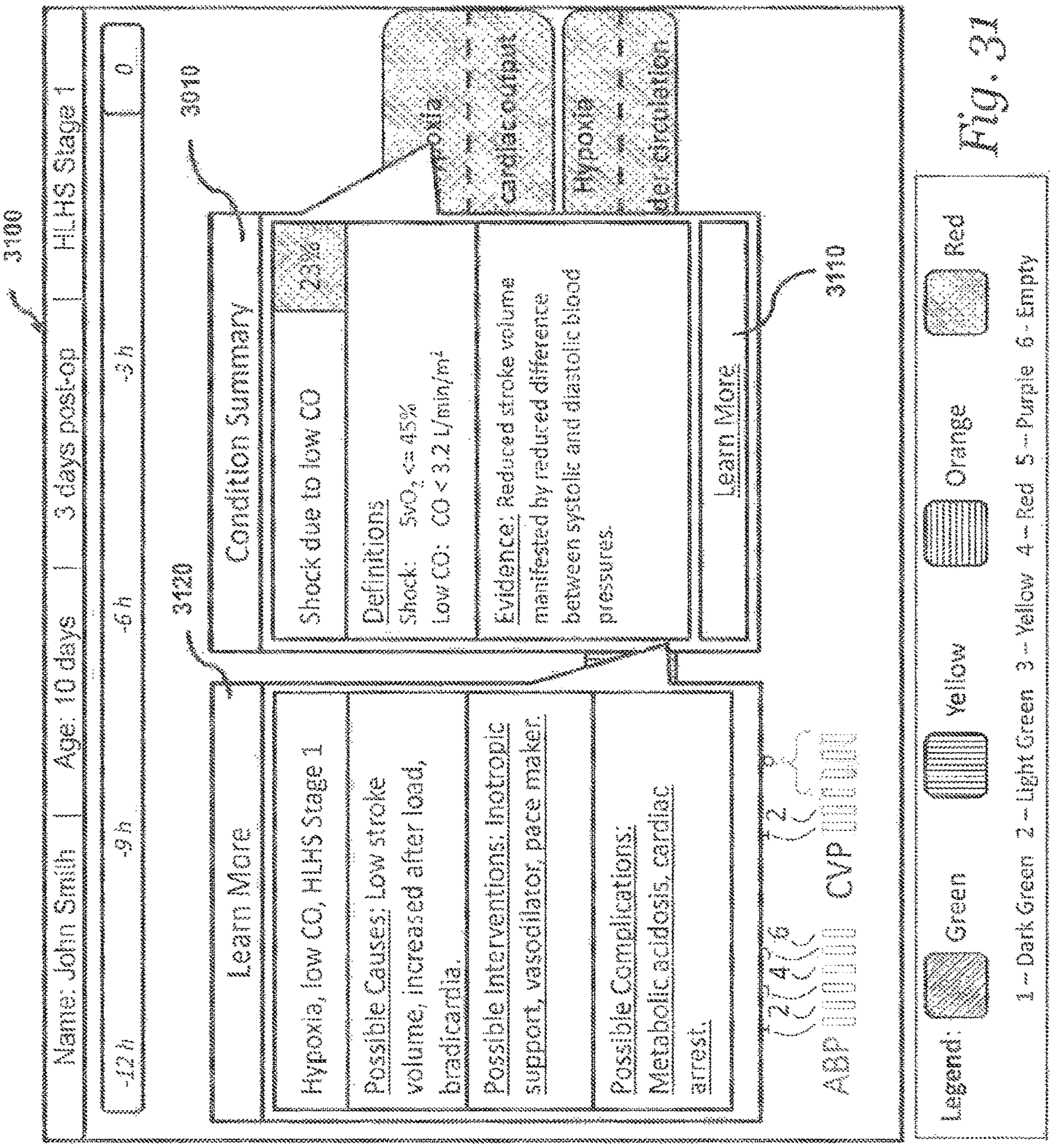
FIG. 31 illustrates conceptually the ability for the user interface to include and display reference material, which may be accessed through the Internet; or stored within the system in accordance with the disclosure.

FIG. 31 further illustrates in view 3100 the ability for the user interface to include and display reference material, which may be accessed through the Internet, or stored within the system 100 or remotely accessible thereby. Selecting the Learn More button 3110 in the Condition Summary View 3010 may bring up a Learn More View 3120, which shows reference information associated with the Condition Summary View 3010. Reference information may include causes, interventions, common comorbidities, anatomy, relevant publications, etc. Furthermore, this feature may serve as a training tool to familiarize clinicians with managing the particular patient population, or treatment strategies.

HLHS Stage 1 Example

The following description explains how the disclosed system 100 and techniques can be applied to the modeling of the clinical course of a specific patient population under intensive care—post-operatively recovering Hypoplastic Left Heart Syndrome patients after stage one palliation.

Hypoplastic Left Heart Syndrome is a congenital heart defect, which is manifested by an underdeveloped left ventricle and left atrium. As a result, patients suffering from this condition do not have separated systemic and pulmonary blood flows, but instead the right ventricle is responsible for pumping blood to both the body and the lungs. Therefore, the hemodynamic optimization during intensive care involves managing the fractions of the blood flow that pass through the lungs (pulmonary flow $Q_p$) and the body (systemic flow $Q_s$). The optimal hemodynamic state is reached when, adequate tissue oxygen delivery, $DO_2$, is achieved for a pulmonary to systemic blood flow ratio, denoted $Q_p/Q_s$, of 1. Often, to reach this optimal state, the patient physiology passes through other less beneficial states, and the correct identification of these states and the application of a proper treatment strategy for each one of them define the quality of the post-operative care.

skilled in the relevant arts will recognize that though these variables encompass circulation, hemodynamic, and the oxygen exchange components of HLHS physiology, the models can be altered or enhanced with any additional physiologic components such as ventilation, metabolism, etc. without altering the premise of the disclosed invention.

Figure 32:
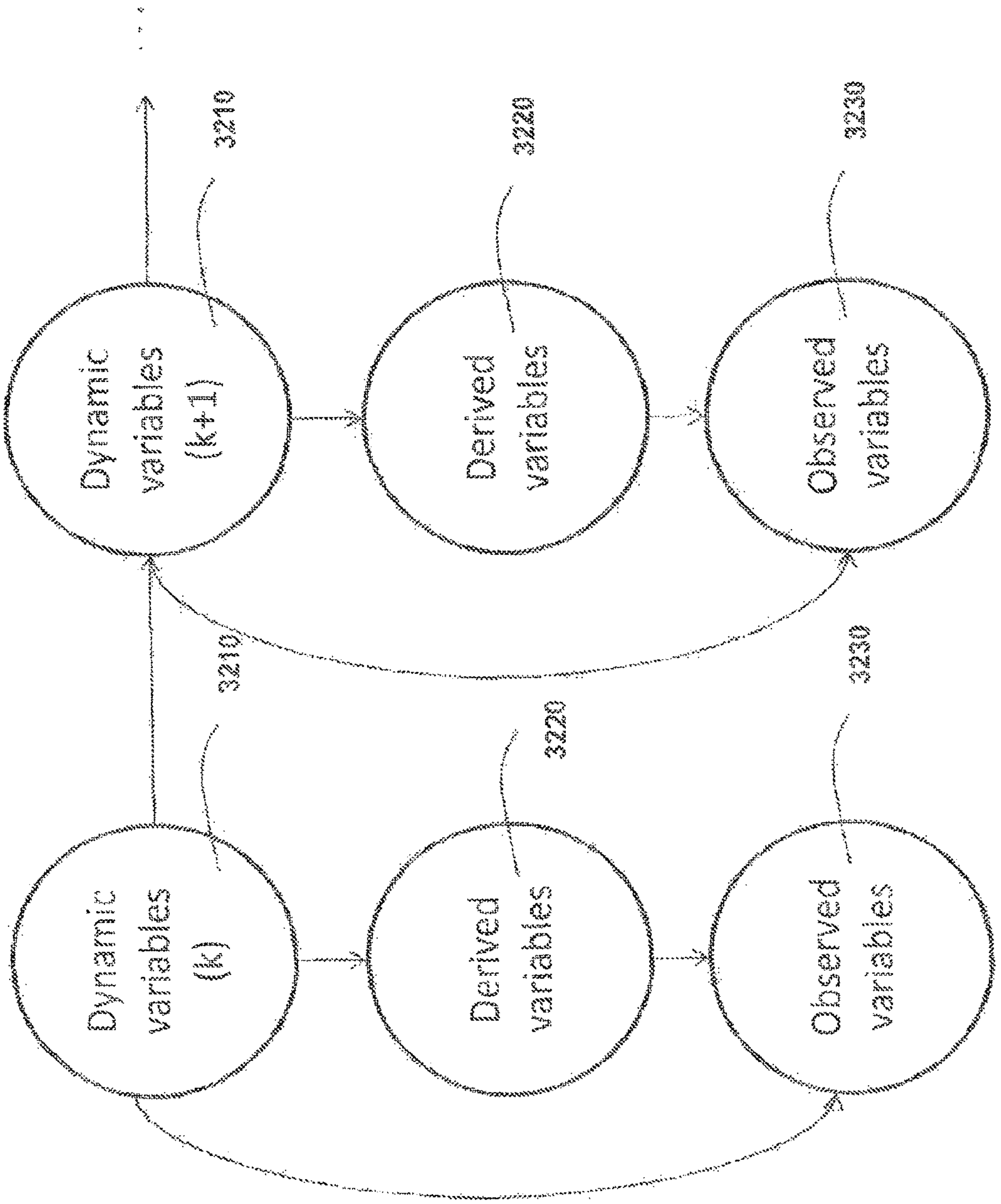
FIG. 32 illustrates conceptually a general Dynamic Bayesian Network (DBN) that may be employed to capture the physiology model of the HLHS stage 1 palliation patients in accordance with the disclosure.

FIG. 32 depicts a general Dynamic Bayesian Network (DBN) that may be employed to capture the physiology model of the HLHS stage 1 palliation patients. The graphical model illustrated conceptually in FIG. 32 captures the causal and probabilistic relationship between the variables of the model. In the DBN, the state variables are organized into three groups: dynamic variables 3210, derived variables 3220, and observed variables 3230. Dynamic variables 3210 are variables whose values change over time based on a dynamic probabilistic model to be described below. Derived variables 3230 are quantities that depend on the dynamic variables with some functional relationship. These variables are computed or derived when required from the latest dynamic variables and are therefore also dynamic in nature. Observed variables 3230 are those variables that are measured directly by one of the sensors connected to the system and the patient. Observed variables 3230 represent instances of the true dynamic or derived states variables that have been observed under noise.

FIG. 33 lists several equations that may be used to model the dynamics of the HLHS stage 1 physiology. The model

TABLE 1

| Variable | Description | Units | Type |
|---|---|---|---|
| $DO_2$ | Indexed Oxygen Delivery | mL $O_2$/min/$m^2$ | Dynamic |
| $VO_2$ | Indexed Oxygen Consumption | mL $O_2$/min/$m^2$ | Dynamic |
| PVR | Pulmonary Vascular Resistance | mm Hg/L/min/$m^2$ | Dynamic |
| SVR | System Vascular Resistance | mm Hg/L/min/$m^2$ | Dynamic |
| ΔPVR | Change in PVR per time step | mm Hg/L/min/$m^2$ | Dynamic |
| ΔSVR | Change in SVR per time step | mm Hg/L/min/$m^2$ | Dynamic |
| Hb | Hemoglobin | g/dL | Dynamic/Observed |
| HR | Heart Rate | Beats per min | Dynamic/Observed |
| $SpvO_2$ | Pulmonary Venous Oxygen Saturation | % | Dynamic |
| $SaO_2$ | Arterial Oxygen Saturation | % | Derived/Observed |
| $SvO_2$ | Systemic Venous Oxygen Saturation | % | Derived/Observed |
| $SpO_2$ | Pulmonary Venous Oxygen Saturation | % | Observed |
| η | Aortic Compliance | | Dynamic |
| ABPm | Mean Arterial Blood Pressure | mm Hg | Derived/Observed |
| CVP | Central Venous Pressure | mm Hg | Dynamic/Observed |
| LAP | Left Atrial Pressure | mm Hg | Dynamic/Observed |
| RAP | Right Atrial Pressure | mm Hg | Dynamic/Observed |
| ΔP | Pulse Pressure | mm Hg | Derived/Observed |
| CO | Total Cardiac Output | L/min/$m^2$ | Derived |
| $Q_p$ | Pulmonary rate of blood flow | L/min/$m^2$ | Derived |
| $Q_s$ | Systemic rate of blood flow | L/min/$m^2$ | Derived |
| $Q_p$:$Q_s$ | Ratio of $Q_p$ to $Q_s$ | | Derived |
| $\Delta Q_p$:$Q_s$ | Change in Ratio of Qp to Qs per time step | | Derived |
| $c_{DO2}$ | Oxygen Delivery feedback constant | | — |
| $c_{VO2}$ | Oxygen Consumption feedback constant | | — |
| $c_{Hb}$ | Hemoglobin feedback constant | | — |
| $c_3$ | Aortic compliance scaling constant | | — |
| $c_4$ | Aortic compliance offset | | — |
| $c_5$ | Hemoglobin oxygen carrying capacity | | — |

Table 1 lists state variables that may be used in the model of HLHS physiology after stage 1 palliation, the variable description, units, and type of variable. A person reasonably consists of four main types of stochastic models. The first type of model is a stochastic feedback control model (eqs. 1, 2, and 7). These variables have a nominal value that the body maintains, but are disturbed by some random process off of this nominal value. The strength at which the body attempts to maintain these values is decided by the feedback constant. The second type of model is a drift diffusion process (eqs, 3 and 4). These variables are driven over time by a random white noise process and a drift rate process. The third type of model is a simple random walk process (eqs. 5, 6, and 8). The last type of dynamic model is a memory-less process model in which the variable has no relationship to the variable at the previous time period, but is simply a random variable which value changes at each time instance according to some predefined distribution over the proper support of the variable, i.e. a gamma distribution over the entire positive real line with parameters A and B. (eqs. 9, 10, and 11). With the exception of equations 9, 10, and 11, the driving noise for each dynamic model is independent white Gaussian noise.

FIG. 34 depicts example equations that may be used to abstract the relationships between the dynamic variables in the model and the derived variables. Some of these functional relationships are true for general human physiology, but many are the result of the parallel circulation physiology that is specific to the HLHS population. Equations 12-15 describe relationships for variables that are measured directly. Equations 16-18 describe functional relationships for variables that are of highest interest when managing care of HLHS patients post-surgery, specifically Cardiac Output (CO) and Pulmonary to Systemic Flow ratio (Qp:Qs). These variables cannot be measured directly without complex procedures.

Given these functional relationships and the definition of the dynamic states, FIG. 35 now provides a possible observation model that may be used to relate the derived variables with the available sensor data. Each observation model is a conditional Gaussian relationship. Under this model, the measurement received from the sensor represents a direct observation of the underlying state variable corrupted by additional independent Gaussian White noise with some variance. The figure depicts the observed quantity as the underlying state variable with a tilde over the variable name. In this implementation, different sensors can map to the same underlying state variable, but with potentially different noise levels. For example, SpO2 as reported by a pulse oximeter measures the underlying physiology state, SaO2 or arterial oxygen saturation non-invasively. An intravenous catheter inserted directly into the arterial blood stream also measures this quantity but in an invasive way. The catheter measurement should be a more accurate measurement than the pulse oximetry. In this model, this is handled with a smaller measurement variance, R.

In the HLHS physiology observer, inference over the DBN is performed using a particle filter. As described earlier, a particle filter is an example of an approximate inference scheme that uses Monte Carlo samples of the internal state variables to approximate the probability density function of each state variables with an empirical distribution based on the number of particles. The filter uses a process known as Sequential Importance Sampling (SIS) to continuously resample particles from the most recent approximate probability distribution. In the filter, each particle is assigned a weight. When a new observation or measurement arrives, the weights of each particle are updated based on the likelihood of the particular particle given the observation. The particles are then resampled based on their relative updated weights, the particles with the highest weights being more likely to be resampled than those with lower weights.

Figure 36:
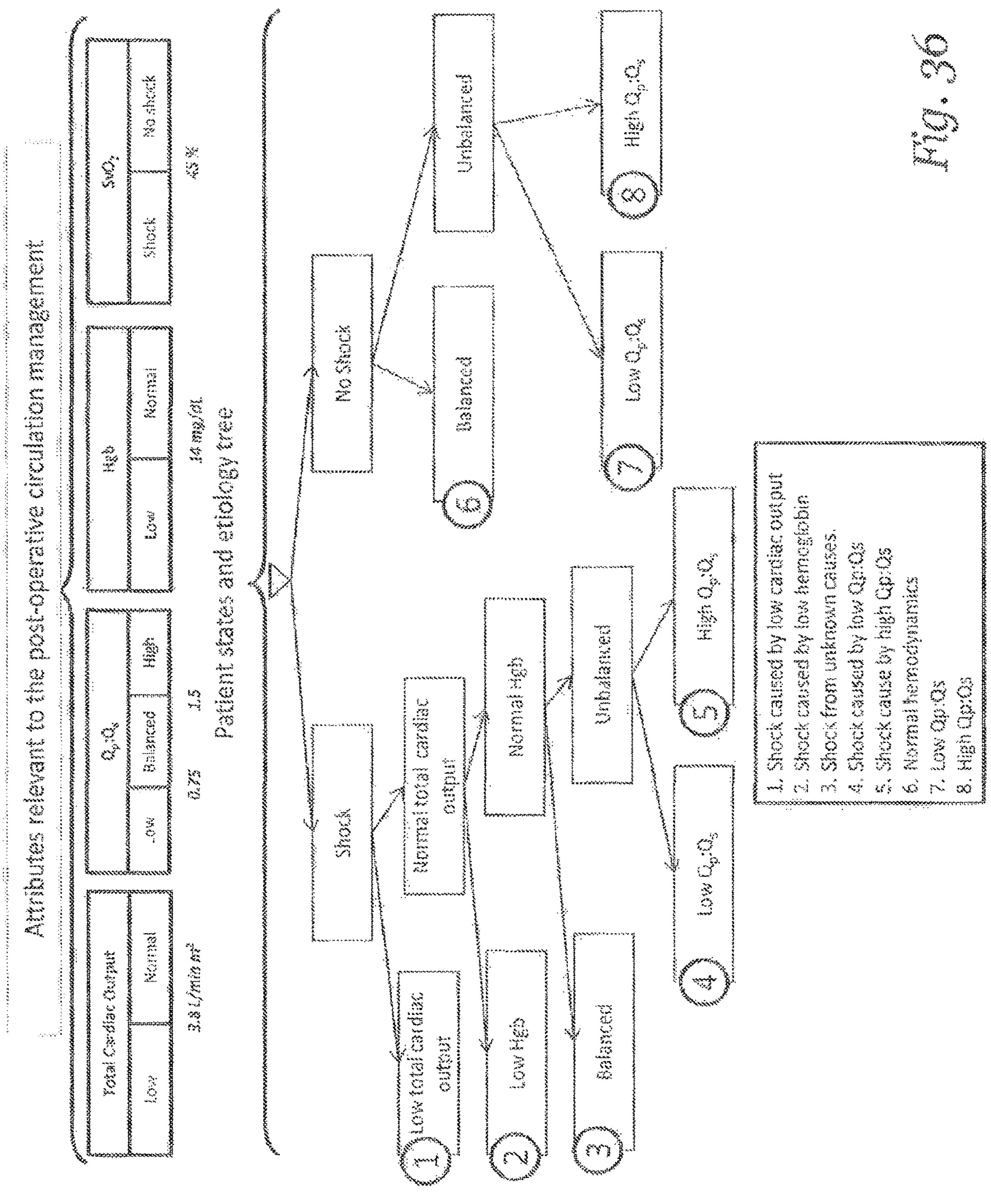
FIG. 36 illustrates conceptually possible attributes, patient states, and etiology tree that may be used by the clinical trajectory interpreter module in the case of the HLHS Stage 1 population in accordance with the disclosure.

FIG. 36 illustrates possible attributes, patient states, and an etiology tree that may be used by the clinical trajectory interpreter module 123 in the case of the HLHS Stage 1 population. The variable total cardiac output defined as the sum of the systemic and the pulmonary blood flows is used to define low and normal total cardiac output, the Qp:Qs ratio is used to derive low, balanced, and high Qp:Qs ratio, the value of hemoglobin concentration Hgb is used to derive low and normal hemoglobin, and the value of the mixed venous oxygen saturation, SvO2, is used to derive the attributes hemodynamic shock and no hemodynamic shock. This results in eight possible states defined as follows: 1) Shock caused by low total cardiac output, as the presence of both of the attributes Shock and low total cardiac output; 2) Shock caused by low hemoglobin as the state with attributes shock, normal total cardiac output, and low hemoglobin; 3) shock from unknown causes as the state with the attributes shock, normal total cardiac output, normal hemoglobin, and balanced circulation; 4) shock cause by low Qp:Qs as the state with the attributes shock, normal total cardiac output, normal hemoglobin, and low Qp:Qs; 5) shock cause by high Qp:Qs as the state with the attributes shock, normal total cardiac output, normal hemoglobin, and high Qp:Qs; 6) normal circulation as a state with the attributes of no shock and normal circulation; 7) low Qp:Qs as the state defined by the attributes of no shock and low Qp:Qs; and 8) high Qp:Qs as the state defined by the attributes of no shock and high Qp:Qs. FIG. 35 also illustrates a possible realization of an etiology tree describing the relationships between the attributes and the patient states. Using the particles approximation of internal state variables the probability of the eight states can be calculated by calculating the relative fraction of particles within each state.

Example of Applying the Risk-Based Monitoring System in Conjunction with Evaluating Consequences of a Possible Treatment Another possible application of the risk based monitoring system is to assist clinicians when deciding whether to apply a particular treatment, one example being blood transfusion. Transfusion of blood and blood products is a common in-hospital procedure. Despite that blood transfusion indications and policies are neither well established nor consistently applied within or between medical centers. Multiple studies have demonstrated variation in transfusion practices among different hospitals, practitioners, and procedures. This variation persists even when applied to a single procedure (e.g. coronary artery bypass graft surgery).

Moreover, blood transfusion has been increasingly recognized as an independent risk factor for morbidity and mortality. Specific events and outcomes associated with transfusion include sepsis, organ ischemia, increased time on ventilation support, increased hospital length of stay, and short- and long-term morbidity. This relationship is proportional to the transfusion volume, and evidence suggests that high hematocrit values may be detrimental. Understandably, researchers conventionally recommend transfusion policies aimed at achieving an informed tradeoff between the risks and benefits.

Setting robust and effective transfusion policies has been proven to be a difficult task. The consensus in the medical community is that simple policies—such as hemoglobin threshold policies—do not provide adequate guidance. This is due to the compensatory nature of hemodynamic physiology; patients have a variable capacity to tolerate low hemoglobin. Consequently, effective transfusion decision-making must integrate factors such as compensatory reserve, intravascular volume, hemodynamic stability, procedure type, and other patient data. Thus, there is an essential need for blood management policies that will utilize the full spectrum of relevant clinical variables and determine the risk/benefit ratio of transfusion. This is exactly afforded by applying the risk based monitoring system.

Figure 37:
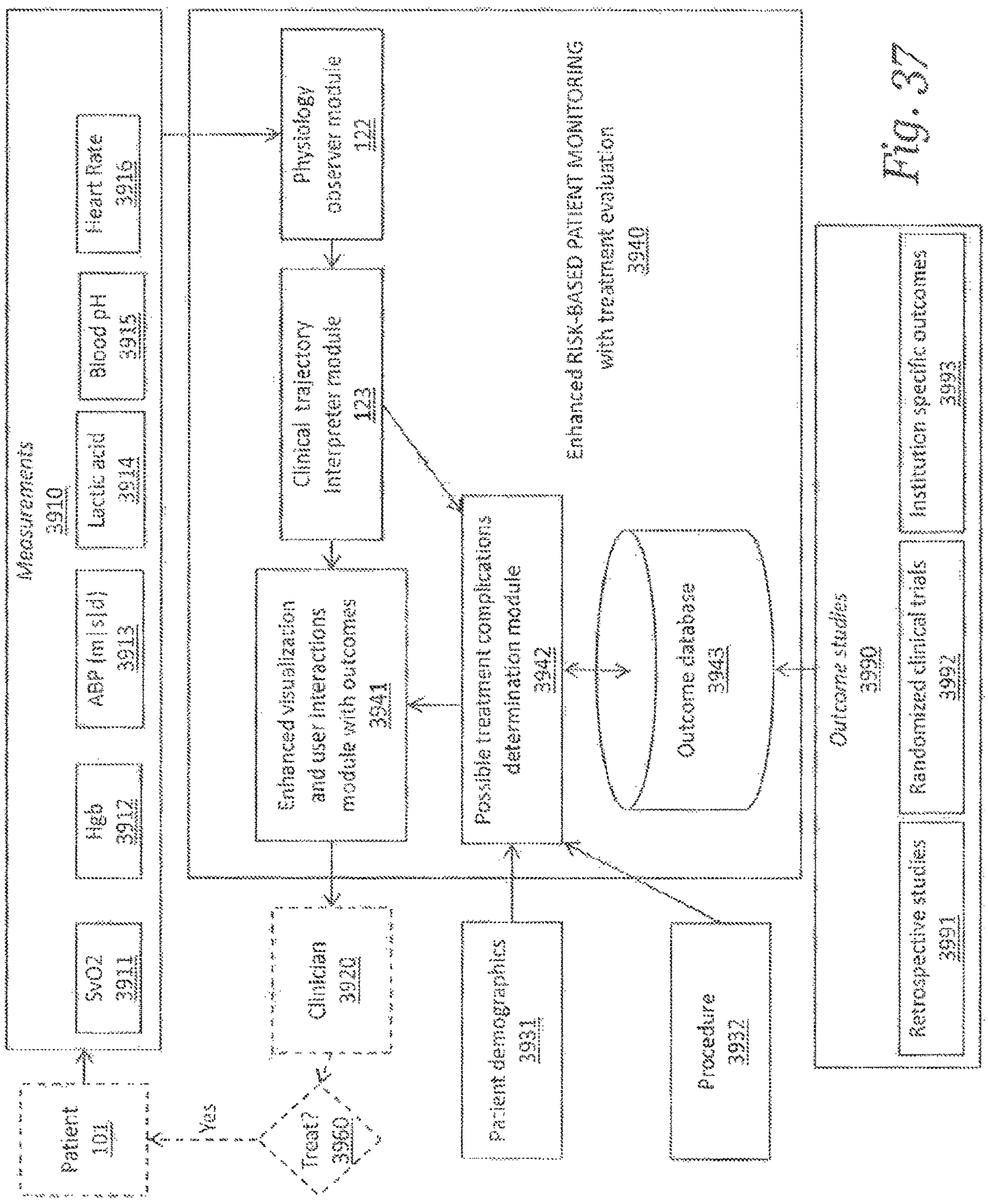
FIG. 37 illustrates conceptually one possible environment in which the risk-based monitoring system can be applied to assist clinicians in deciding whether to apply a particular treatment in accordance with the disclosure.

FIG. 37 illustrates one possible environment in which the risk based monitoring system can be applied to assist clinicians in deciding whether to apply a particular treatment. Consistent with the disclosure, a patient 101 is being monitored with multiple measurements 3910, both intermittently and persistently. The persistent measurements may include mixed venous oxygen saturation (SvO2) 3911, systolic, diastolic and mean arterial blood pressures (ABP s|d|m) 3913, heart rate 3916, monitored via a bedside monitor. The intermittent measurements may include blood pH 3915, hemoglobin concentration (Hgb) 3912, and lactic acid concentration 3914 monitored through periodic blood works. These measurements 3910 are fed into an enhanced risk based monitoring system 3940 with treatment evaluation, which, in addition to the previously disclosed physiology observer module 122 and clinical trajectory interpreter module 123, consists of several other modules. A possible treatment complications determination module 3924 receives information from the clinical trajectory interpreter module 123, together with information about the patient demographics 3931 and type of procedure 3932. With the information, this module 3924 queries an outcome database 3943 and receives back information of what the probability of different complications can be given that a) the patient is in particular patient states with particular probabilities; b) the patient is of certain demographics (age, sex, etc); c) the patient has had a particular type of procedure; d) and any combinations thereof of a) b) and c). On the other hand, the outcome database 3943 can be populated by using outcome studies 3990 derived from retrospective studies 3991, randomized clinical trials 3992, institution specific outcomes 3993 determined from previously collected patient data for a particular institution, and any combination thereof of the proceeding elements.

When the possible treatment complications determination module 3942 determines the possible complications, it feeds this information back to an enhanced visualization and user interactions module 3941. The enhanced visualization and user interactions module 3941 combines the patient-specific risk based monitoring performed by the physiology observer module 122 and the clinical trajectory interpreter module 122, with the evaluation of probable complication. This affords the system to provide a superior vantage point from which the clinician 3920 can better recognize risks and benefits of treatments such as blood transfusion, and respectively more efficiently and effectively decide whether to administer this treatment 3960 or not.

Figure 38:
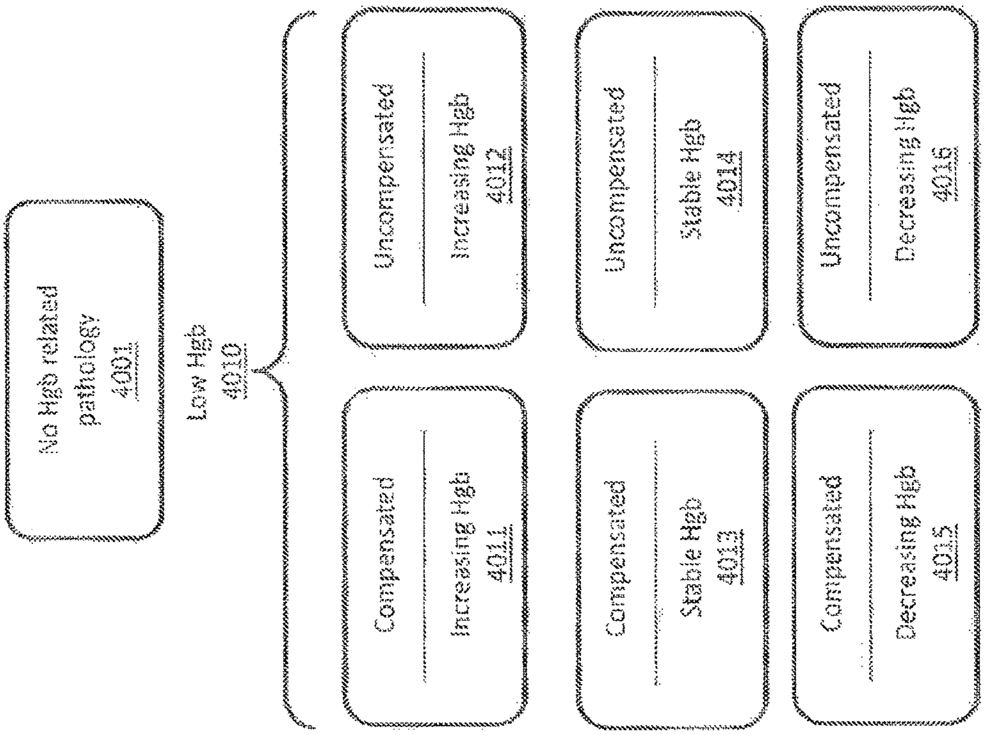
FIG. 38 illustrates conceptually a non-limiting example set of patient states relevant to blood transfusion that may be used to inform the blood transfusion decision in accordance with the disclosure.

FIG. 38 shows a non-limiting example set of patient states relevant to blood transfusion that may be used to inform the blood transfusion decision. The states contain information about the dynamics of the hemoglobin (decreasing/stable/increasing) and the hemodynamic compensation for reduced blood oxygen carrying capacity. In uncompensated patients, the hemodynamic auto-regulation mechanisms become incapable of overcoming the depleted blood oxygen carrying capacity, marking the onset of anaerobic metabolism. These seven states can be determined through three internal state variables: oxygen delivery, hemoglobin, and rate of hemoglobin production/loss. Specifically, when hemoglobin is above 13 mg/dL, it is assumed that there is no Hgb related pathology 4001. When Hgb is lower than 13 mg/dL, there are six other states, determined through five different attributes. From the oxygen delivery ISV, the system can determine whether the patient is compensated or uncompensated, e.g., it may be assumed that DO2 above 400 ml/min/$m^2$, for ventilated and paralyzed patient, indicates compensation, and below this value uncompensated patient. The other three attributes are determined from the Hgb rate ISV and are stable 4013 and 4014 (the rate is close to zero), increasing 4011 and 4012 (the rate is positive), and decreasing 4015 and 4016 (the rate is negative).

Using the Risk Based Monitoring System with Standardized Clinical Plan

Figure 39:
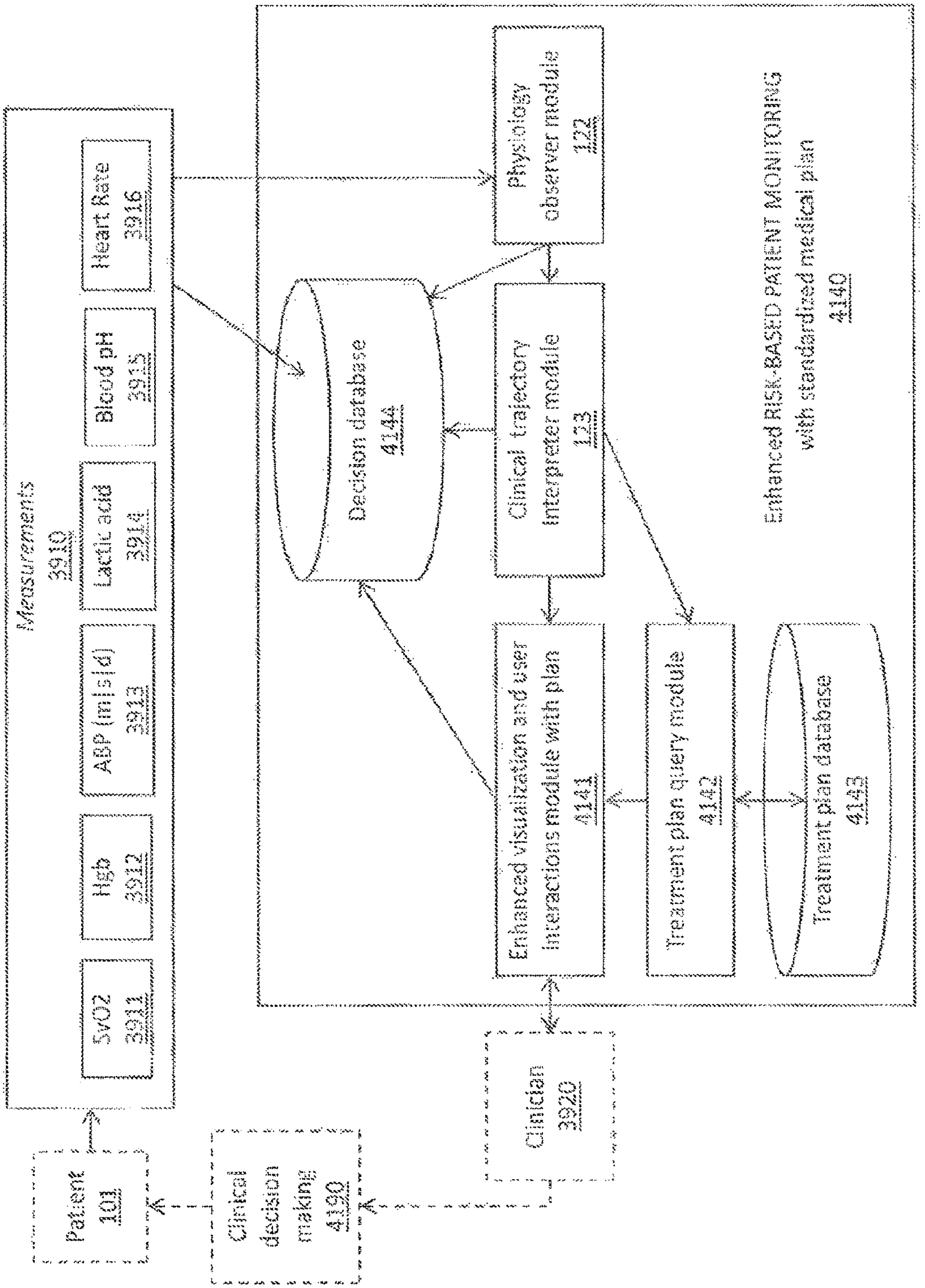
FIG. 39 illustrates conceptually another application of the risk-based monitoring system, applying standardized medical plans in accordance with the disclosure.

Yet another application of the risk based monitoring system is in applying standardized medical plans. FIG. 39 illustrates one possible embodiment of this application. Specifically, the data from the clinical trajectory interpreter module 123 is fed to a treatment query module 4142. The treatment query module 4142 queries a treatment plan database 4143 based on the determined patient risks. The treatment plan database 4143 specifies a map between patient risks and treatments. When the database 4143 returns a treatment plan, it is represented to the clinician 3920 by an enhanced visualization and user interactions module 4141 with plan. The clinician 3920 can then make clinical decision 4190 with respect to patient 101. The user decision, the context under which it was taken, (the calculated patient risks, the estimated ISVs, and other possible patient data at the time of the decision) are then recorded to a decision data base 4144. The decision database 4144 then can be compared to patient outcomes and utilized in the improvement of the treatment plan.

Figure 40:
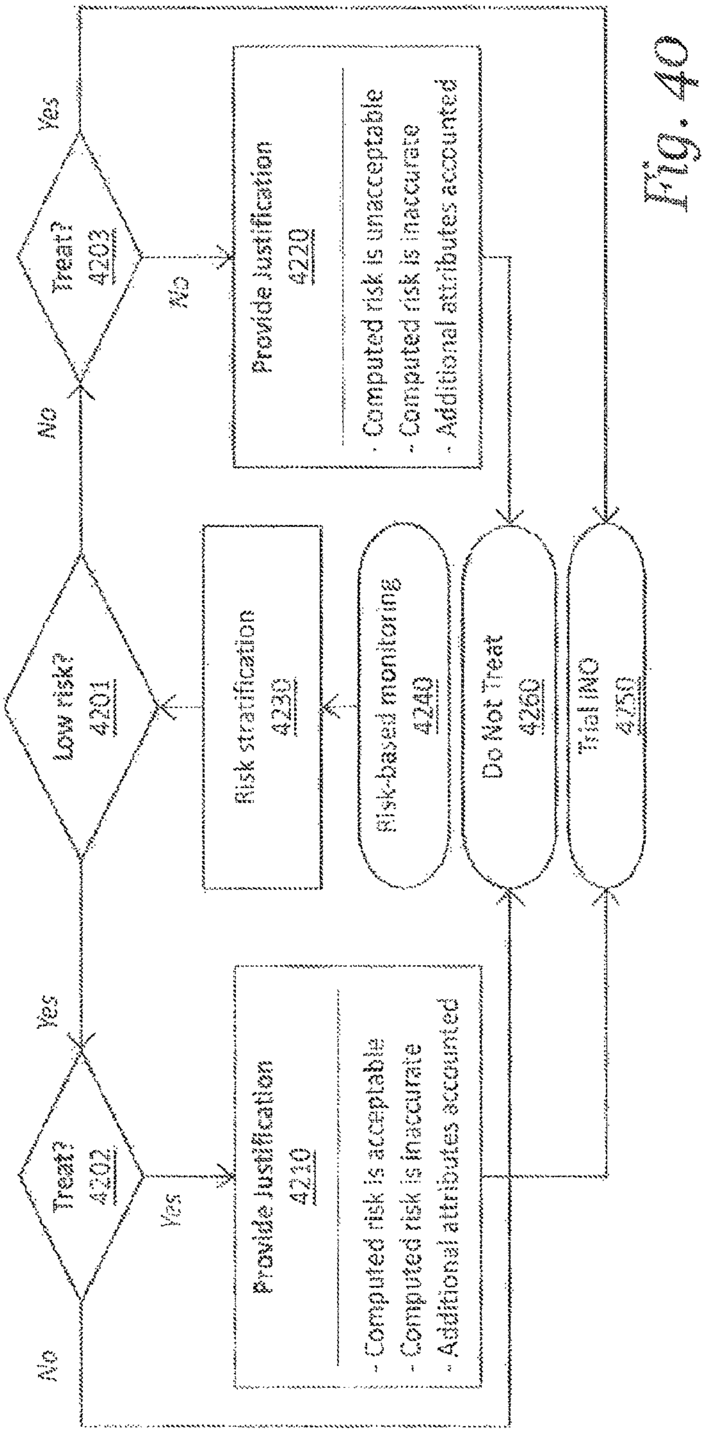
FIG. 40 illustrates conceptually an example application of the risk-based monitoring system combined with a specific type of standardized clinical plan in accordance with the disclosure.

FIG. 40 illustrates an example application of the risk based monitoring system 4240 combined with a specific type of standardized clinical plan. The particular example considers the medical decision whether to treat the patient with nitric oxide. Nitric oxide is a pulmonary vasodilator and is used to treat high pulmonary vascular resistance and ensuing pulmonary hypertension, which can cause reduced cardiac output. In the example, the medical plan uses the risks calculated by the clinical trajectory interpreter module 123 and stratifies 4230 them into two categories: low risk and high risk. If the risks are low 4201 the recommended decision is not to treat 4202, respectively, if the patient is classified as being in high risk the recommended decision is to treat 4203. The provider can then make a decision to either follow the recommendations 4250 or disregard them 4260. If the provider chooses to disregard the treatment recommendation for a high risk patient, he needs to provide justification 4220. Likewise, if the provider chooses to treat a low risk patient, he also needs to provide justification 4210. Justifications 4210 and 4220 in conjunction with patient outcomes may be utilized to refine the risk stratification 4230 and risk-based monitoring system 100.

Figure 41:
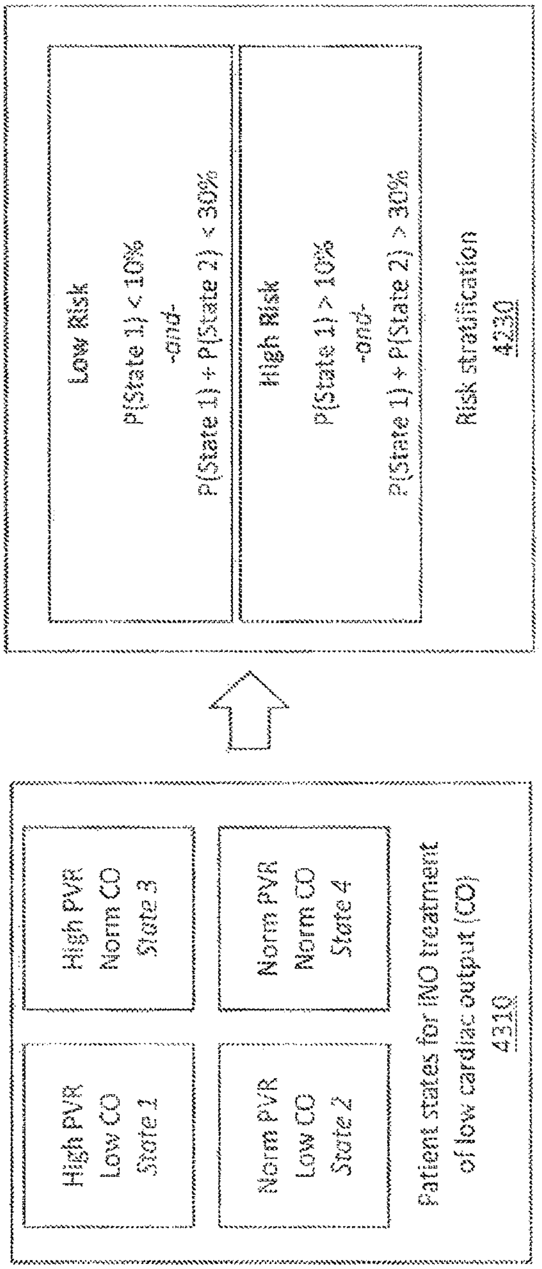
FIG. 41 illustrates conceptually an example risk stratification that may be employed by the system in the context of Nitric Oxide treatment in accordance with the disclosure.

FIG. 41 illustrates the example risk stratification that may be employed by the system in the context of Nitric Oxide treatment. Specifically, it assumes that the patient can be in four different states: State 1: Low CO, Normal PVR; State 2: Low CO, High PVR; State 3: Normal CO, High PVR; State 4: Normal CO Normal PVR. A patient being in low risk may be defined as $P(\text{State } 1)<10\%$ and $P(\text{State } 1)+P(\text{State } 2)<30\%$. Similarly high risk may be defined as: $P(\text{State } 1)>10\%$ and $P(\text{State } 1)+P(\text{State } 2)>30\%$.

Using the Clinical Risk Assessment System in Outpatient Care of Chronic Conditions Yet another embodiment of the present disclosure allows the clinical trajectory tracking in outpatient care. Outpatient care of chronic conditions involves sporadic patient assessment from intermittent visits, patient self-evaluations, and observations from caregivers. This leads to uncertainties in determining the patient clinical course and the efficiency of the prescribed treatment strategy. To achieve effective patient care management, clinicians must understand and reduce these uncertainties. They have two main decisions at their disposal: 1) schedule visits, prescribe tests, or solicit self-evaluation (or caregiver evaluations) to improve their understanding of the clinical trajectory; and/or 2) prescribe changes of medication or medication dosing to achieve a better trade-off between the likelihood of improvement and possible side-effects. To inform this decision making process, there is a need for processing the available patient information in a way that conveys the clinical trajectory, the uncertainty in its estimation, and the expected effect that different treatment strategies may have on the future evolution of the clinical trajectory.

As a non-limiting example embodiment of the risk based monitoring system to outpatient clinical trajectory tracking, we consider its application to the outpatient care of Attention Deficit and Hyperactivity Disorder (ADHD) of pediatric patients. FIG. 42 illustrates possible patient states that may describe the clinical trajectory of an ADHD patient. They are the same as the ones used by the Clinical global impression-improvement scale: 1) very much worse; 2) much worse; 3) worse; 4) No change; 5) Minimally Improved; 6) Much improved; 7) Very much improved. The Patient State Distribution (PSD) is the set of probabilities that the patient is in any of the seven states, given all available information and observations.

To evaluate the patient state, a clinician may either schedule an office visit for direct examination, or may request a Vanderbilt diagnostic test from family members or teachers (the test is modified depending on the respondent, teacher or parent). FIG. 43 lists the available patient evaluation modalities as M1. M2 and M3. Models may be used to map the test questions and answers into the states of the patient. Both the clinical evaluation and the test-based evaluation are associated with uncertainty that prohibits the exact determination in which of the seven states the patient currently resides.

The dynamic model or the patient evolution from state to state may be abstracted by a Dynamic Bayesian Network (DBN) as the one shown in FIG. 44. In FIG. 44, the arcs' directions signify statistical dependence, i.e., the connection from "Patient state @ t1" 4601 to "M1", signifies the probability density function (PDF): P(M1|Patient state @ t1). Similarly, the depicted DBN illustrates that "Patient state @ t2" 4602 (the patient state at a particular time t2), is conditioned on the "Patient state @ t1" (the patient state at the previous time increment t1). In the spirit of the present disclosure, this model enables the estimation of the patient state distribution even in the absence of some or all possible measurements, e.g., as illustrated in the figure at time instance t2 when M1 is missing, and at time instance t3 ("Patient state @ t3" 4603), when all measurements are missing.

FIG. 45 illustrates an alternative embodiment for two predictions of how the patient state can transition in a single month given medication change or a dosage change. This prediction is performed based on a statistical model derived in the following fashion: Step 1: Isolate a group of patients from retrospective data which at some point of their treatment have passed through State A and received a change of treatment (Med1 Dose1->Med 2 Dose 2); Step 2: For each patient, set the time instance that this particular event occurred to t0; 3) step 3: for each patient identify what is the patient state at time t0+1 Month (1 M) (or any desired time step unit). 4) calculate the fraction of patients that transition State A->State i where i stands for all seven possible patient states; 5) set the fraction as the probabilities for transition under the particular treatment change.

Figure 46:
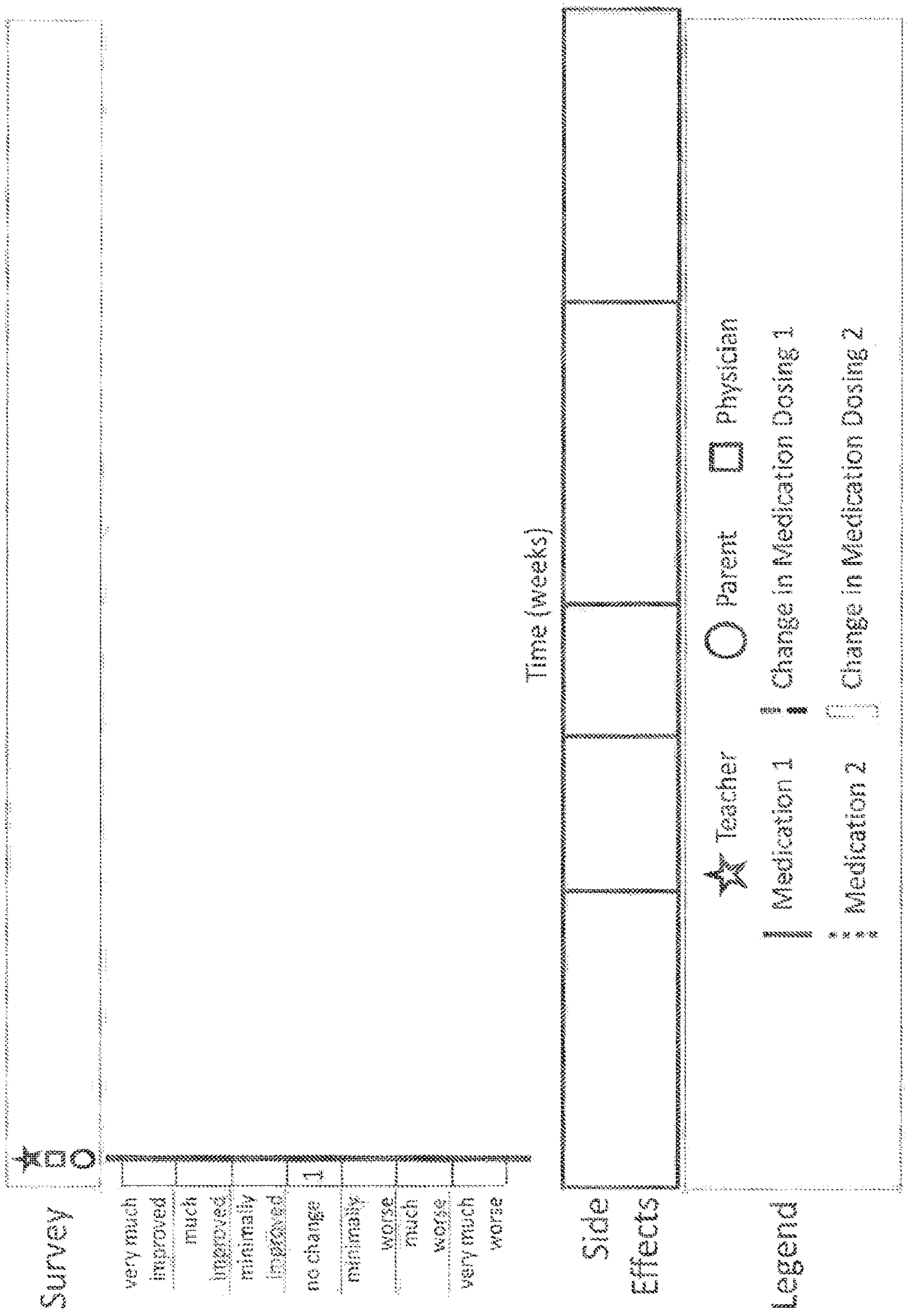
FIG. 46 illustrates conceptually one possible embodiment and scenario of visualization displaying the patient clinical trajectory and risks in accordance with the disclosure.

FIG. 46 shows one possible embodiment and scenario of visualization displaying the patient clinical trajectory and risks. The user interface denotes that the patient is at "no change" state, and that this has been established by three separate measurements: office visit, teacher based Vanderbilt diagnosis, and parent based Vanderbilt diagnosis. The solid line on the screen signifies that a medication has been prescribed to the patient (Medication 1) at week 1 of the treatment.

Figure 47:
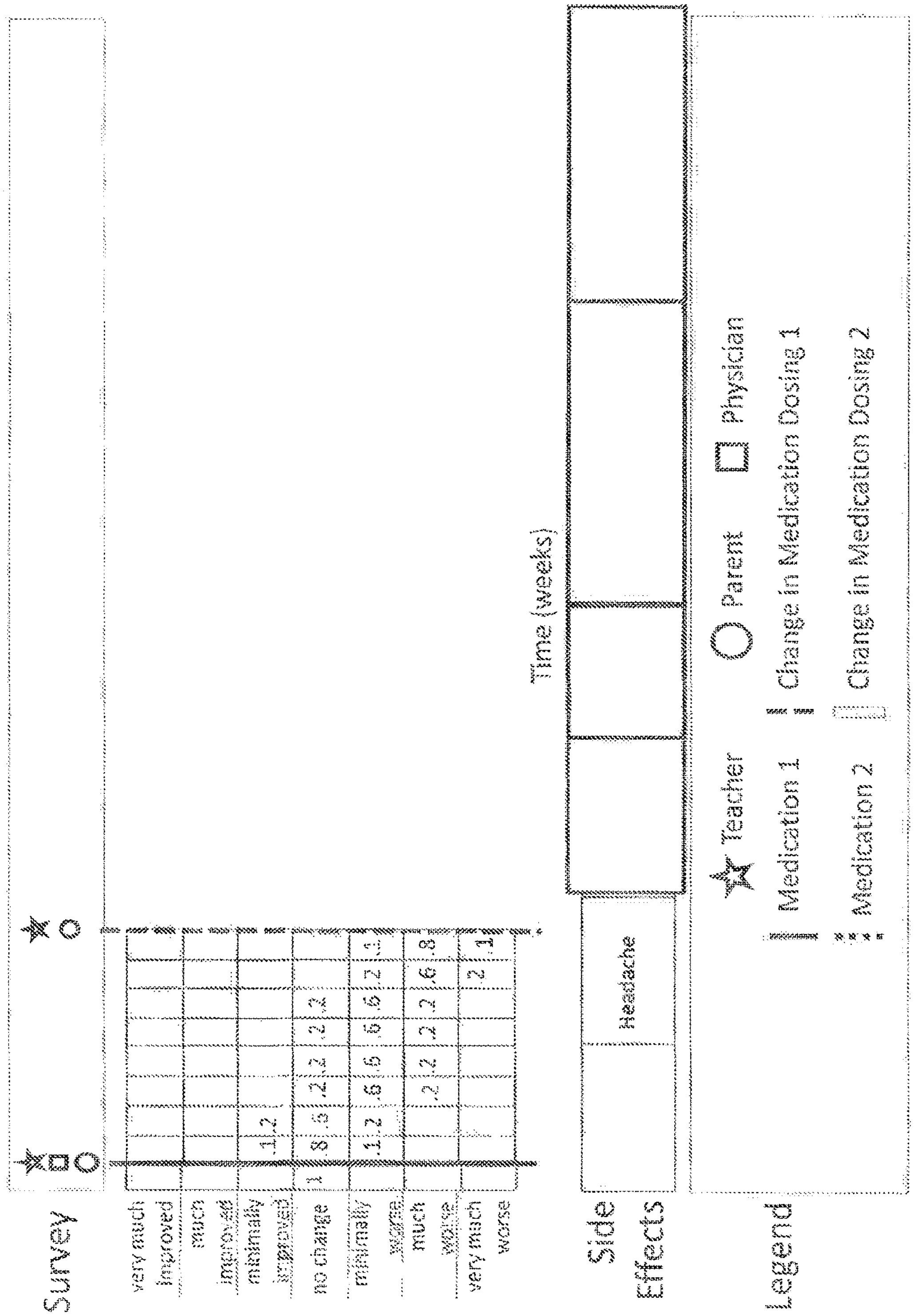
FIG. 47 illustrates conceptually an evaluation of the patient and the patient trajectory at week 9 at which point risk-based patient monitoring system determines a probability distribution function for the state of the patient for each of the past nine weeks in accordance with the disclosure.

FIG. 47 shows an evaluation of the patient and the patient trajectory at week 9 at which point the clinical risk assessment system determines a probability density function for the state of the patient for each of the past six weeks. The available measurements at this point are teacher and parent Vanderbilt diagnosis. In the illustrated example, due to a high probability of a deteriorating patient state, the clinician prescribes a change of medication dosing, which is depicted by a dashed red line. Additionally, the user interface shows the side effect reported by the patient—headache.

Figure 48:
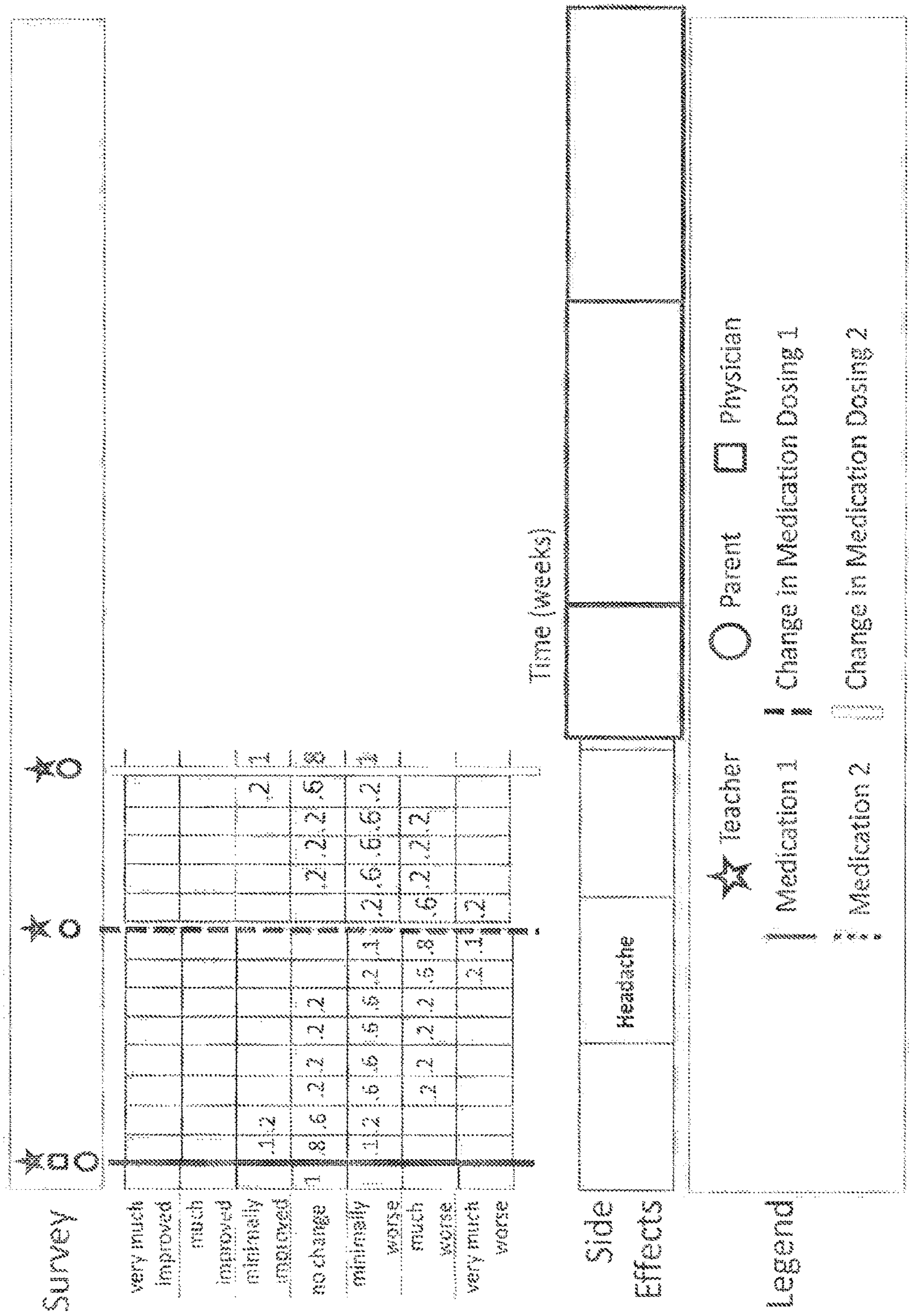
FIG. 48 shows a follow-up evaluation based on teacher and parent Vanderbilt diagnosis in accordance with the disclosure.

FIG. 48 shows a follow-up evaluation based on teacher and parent Vanderbilt diagnosis. In the example, the clinician decides a medication change depicted by a hollow line.

Figure 49:
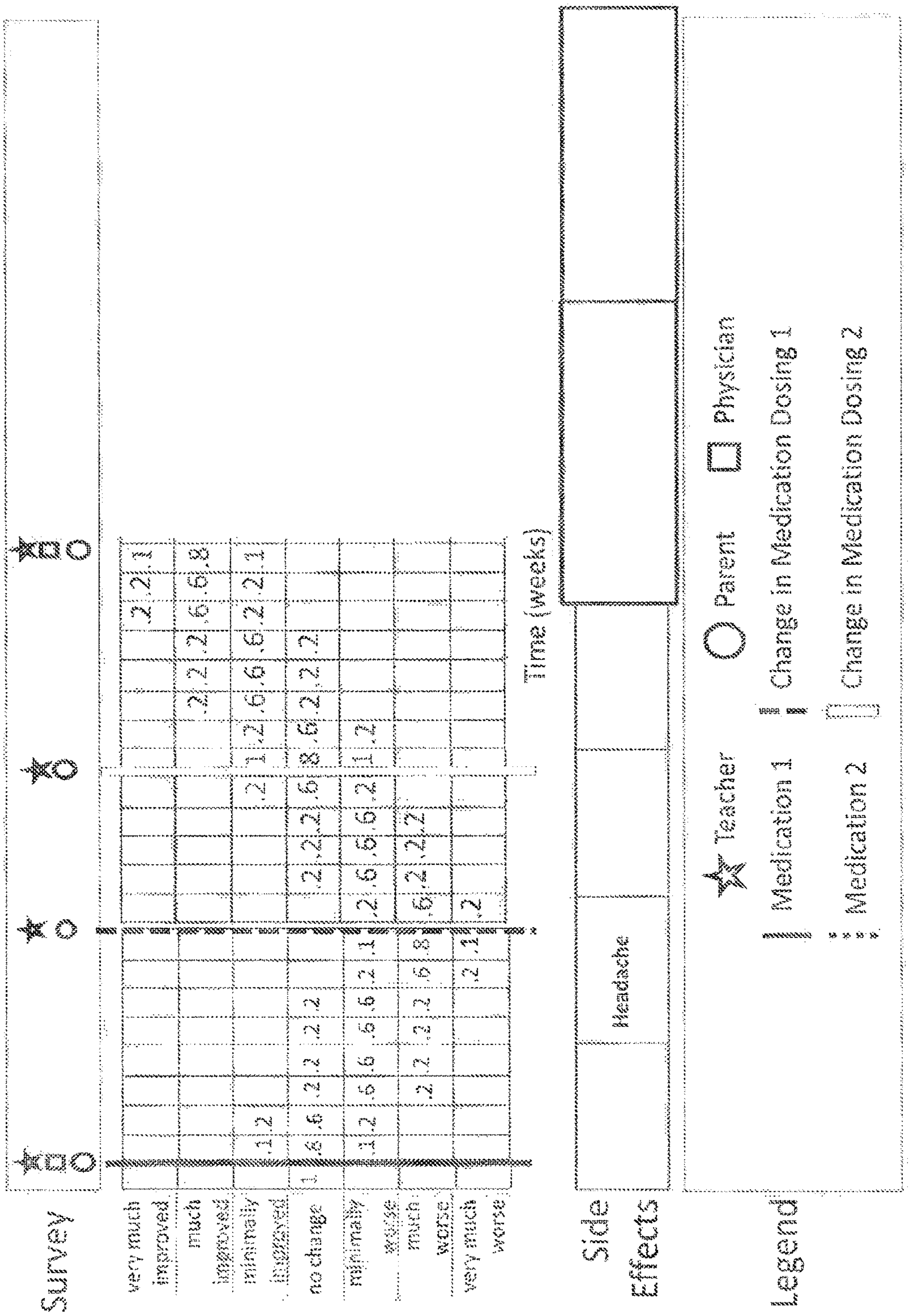
FIG. 49 shows consequent evaluation based on all available measurements—office visit, parent and teacher evaluation, which establishes high probability for significant improvement in accordance with the disclosure.

FIG. 49 shows consequent evaluation based on all available measurements—office visit, parent and teacher evaluation, which establishes high probability for significant improvement.

Figure 50:
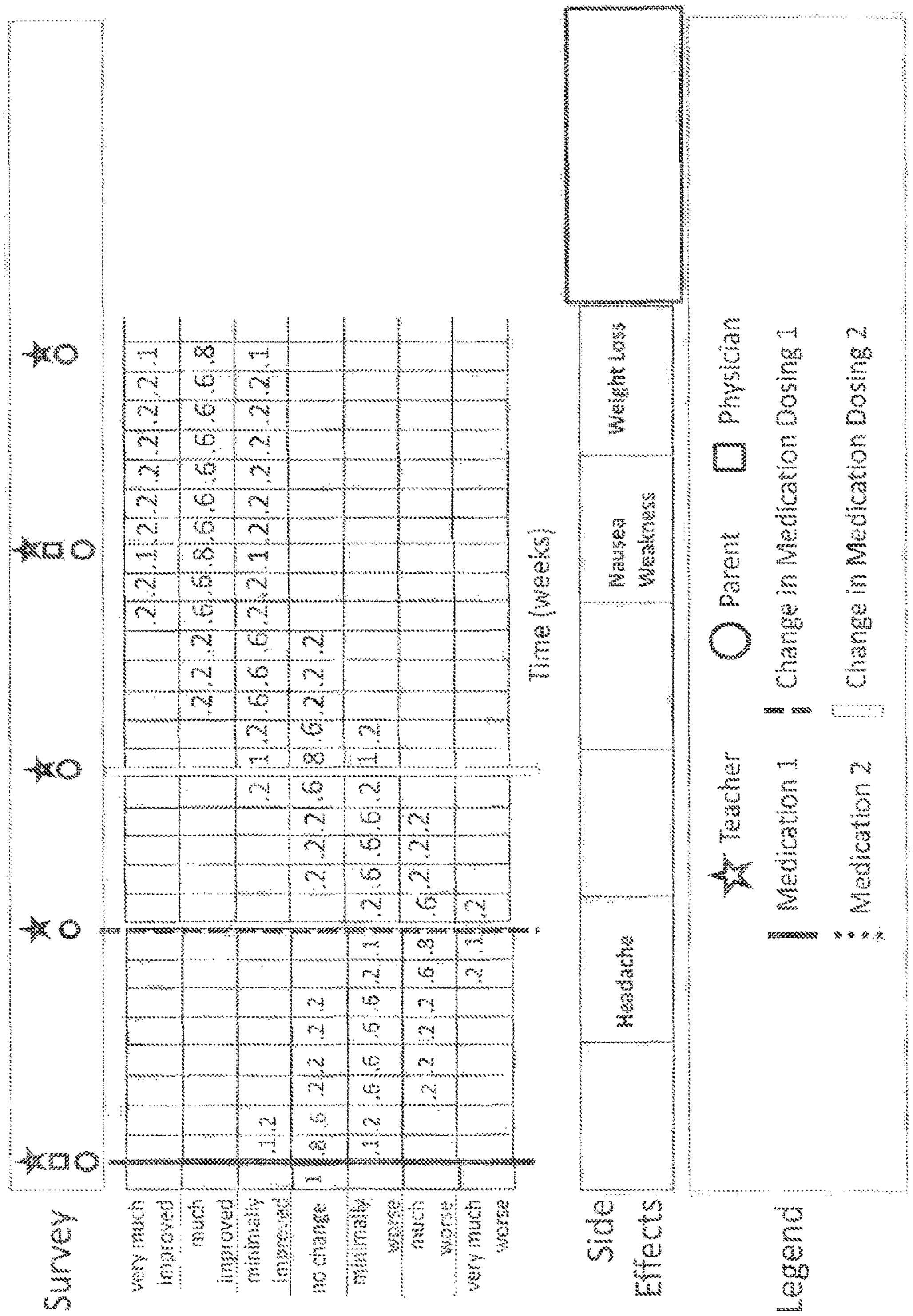
FIG. 50 shows yet another follow-up at which point it is established that the patient is most probably stably improved, and has been stably improved between the two evaluations in accordance with the disclosure.

FIG. 50 shows yet another follow-up at which point it is established that the patient is most probably stably improved, and has been stably improved between the two evaluations. Note that due to the applied inference, the PDF for the patient trajectory is continuously estimated. However, the precision (the concentration of the PDF) is higher in the presence of a measurement.

Figure 51:
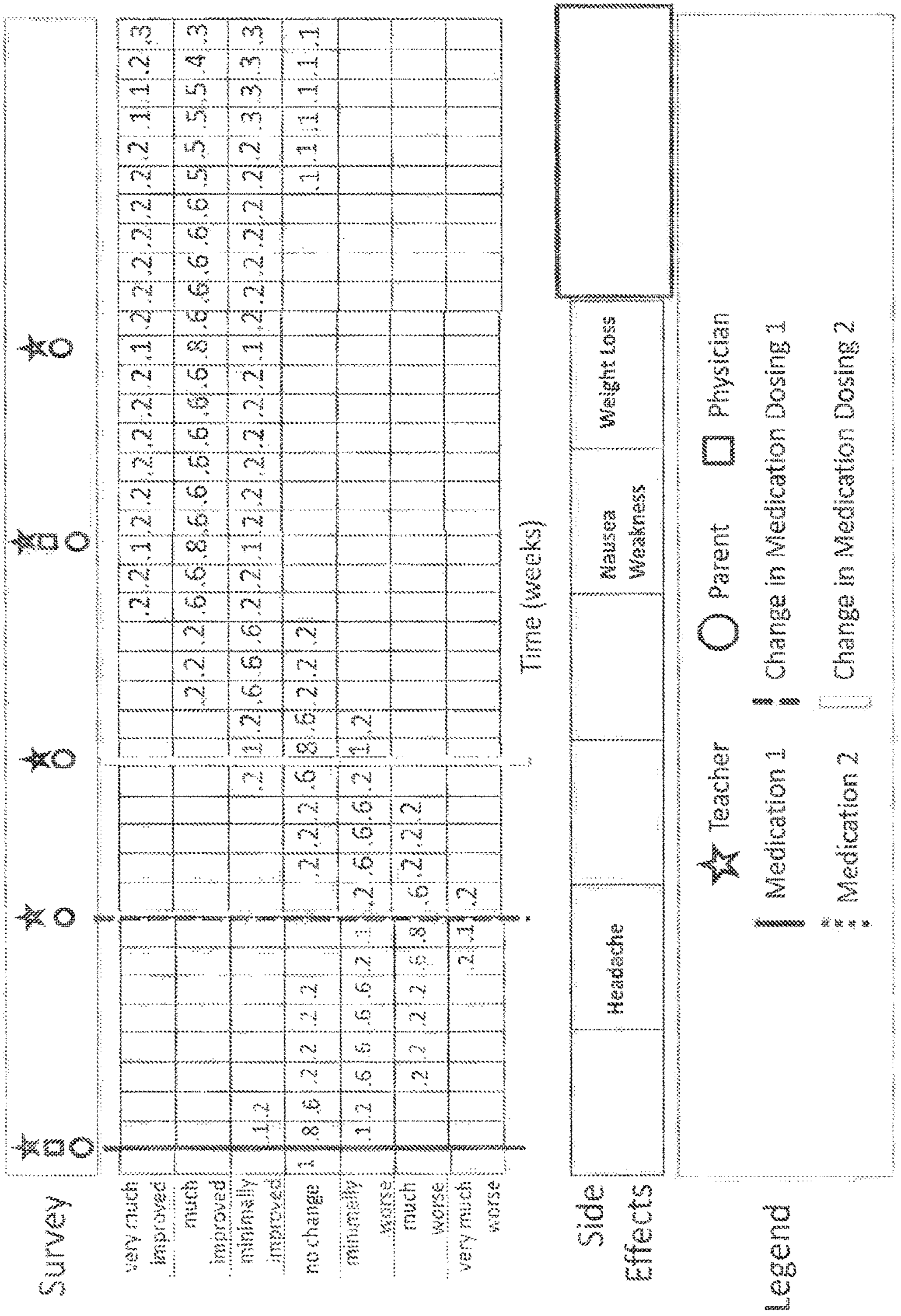
FIG. 51 shows a follow-up evaluation of the patient and the patient trajectory in the absence of measurements, wherein due to the lack of recent observation, the uncertainty is increasing in accordance with the disclosure.

FIG. 51 shows a follow-up evaluation of the patient and the patient trajectory in the absence of measurements. Due to the lack of recent observations, the uncertainty is increasing.

Figure 52:
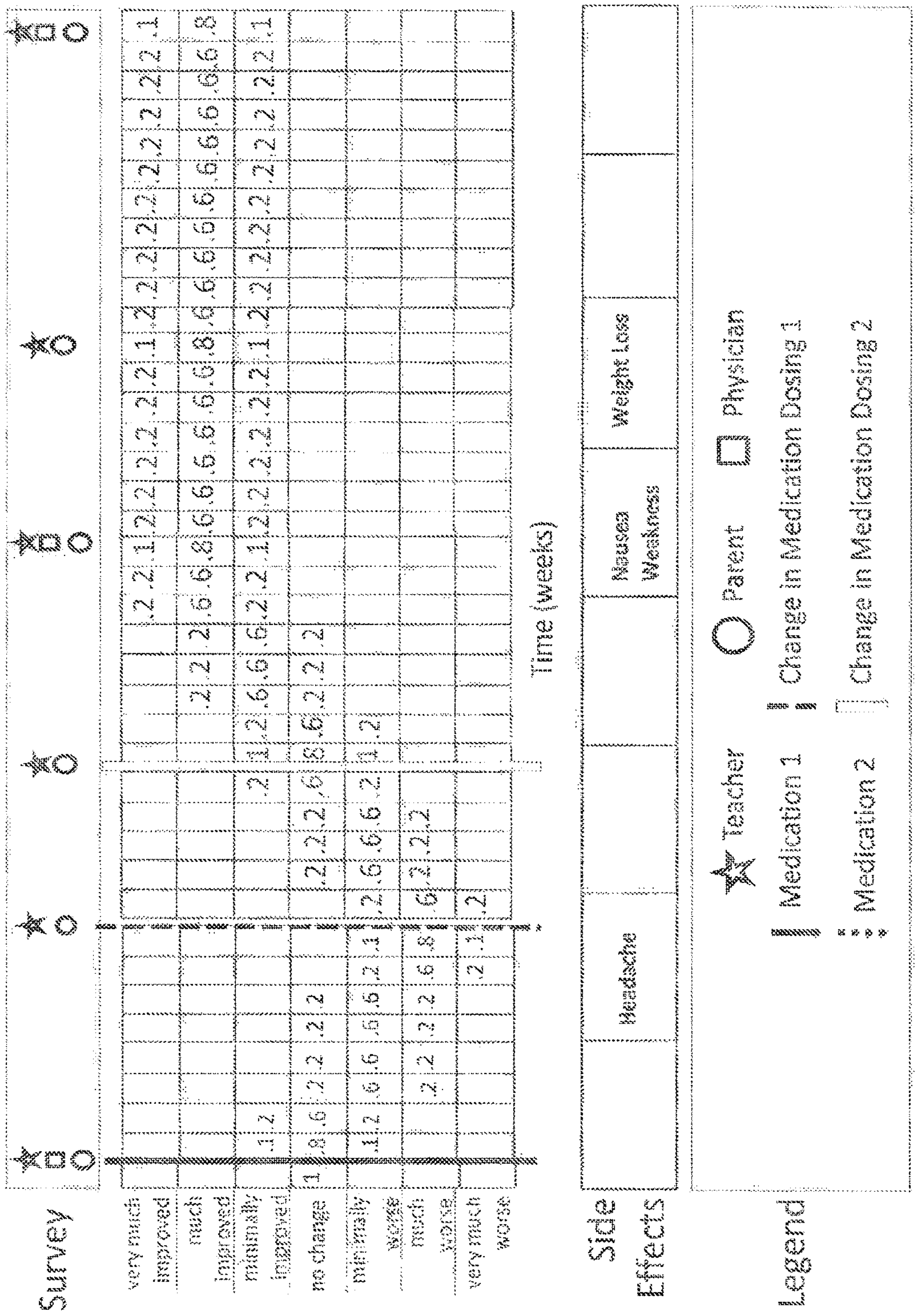
FIG. 52 shows the state of this uncertainty given a full patient evaluation (all measurement modalities) in accordance with the disclosure.

FIG. 52 shows the state of this uncertainty given a full patient evaluation (all measurement modalities). The inference engine propagates this uncertainty back in time to produce a more precise estimation of the patient trajectory, which helps the clinician to deduct that the patient is stable.

Figure 53:
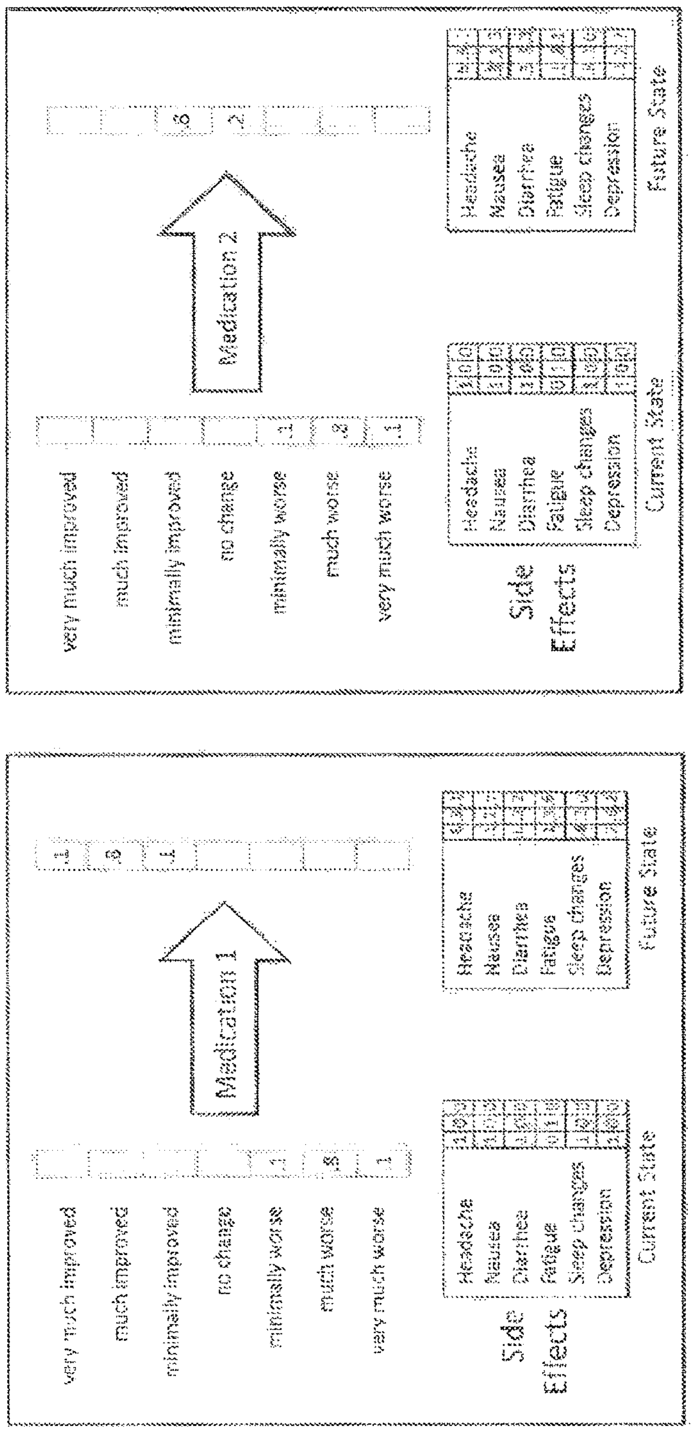
FIG. 53 illustrates yet another possible visualization from the described system output. It shows possible patient state transitions under changes of treatment plan, e.g., change of medication in accordance with the disclosure.

FIG. 53 illustrates yet another possible visualization from the described system output. It shows possible patient state transitions under changes of treatment plan, e.g., change of medication. It also conveys what possible side-effects can be expected. For every side effect, there are three stages of manifestation—mild, moderate, and severe represented with the three boxes next to each side effect in the figure. The coloring corresponds to the probability of a particular severity manifestation for each particular side-effect, with darker colors indicating higher probability.

A listing of certain reference numbers is presented below.

100: Patient-monitoring system;

101: Patient;

102: Bedside monitors;

103: Electronic medical record;

104: Treatment device(s);

105: Laboratory Information System;

111: Computer processor;

112: Computer memory (e.g., non-transient);

113: Network interface;
121: Data reception module;
122: Physiology observer module;
123: Clinical trajectory interpreter module;
130: Reference material;
140: Display and notifications;
210: Predict model (or predict module)
211: Predicted probability density functions of internal state variables;
212: Dynamic model;
213: Estimates of probability density functions of internal state variables;
220: Update model (or update module);
221: Observation model;
230: Conditional Likelihood Kernel;
240: Initial estimates of probability density functions of internal state variables.

Various embodiments may be characterized by the potential claims listed in the paragraphs following this paragraph (and before the actual claims provided at the end of this application). These potential claims form a part of the written description of this application. Accordingly, subject matter of the following potential claims may be presented as actual claims in later proceedings involving this application or any application claiming priority based on this application. Inclusion of such potential claims should not be construed to mean that the actual claims do not cover the subject matter of the potential claims. Thus, a decision to not present these potential claims in later proceedings should not be construed as a donation of the subject matter to the public.

Without limitation, potential subject matter that may be claimed (prefaced with the letter "P" so as to avoid confusion with the actual claims presented below) includes:

P1. A computer-based method of risk-based monitoring of a patient, the method comprising: providing a set of sensors, each such sensor configured to be operably coupled with the patient to produce measurements of a corresponding internal state variable of the patient, the set of sensors including at least one of: (i) a heart rate sensor, and (ii) a pulse oximetry sensor; generating, by the computer, predicted probability density functions of internal state variables for a subsequent time step ($t_{k+1}$), wherein the predicted probability density functions are calculated using posterior estimated probability density functions from a preceding time step ($t_k$); acquiring, by a computer at subsequent time step ($t_{k+1}$), physiological data from the set of sensors connected with the patient; generating a conditional likelihood kernel for the subsequent time step ($t_{k+1}$), the conditional likelihood kernel comprising conditional probability density functions of the physiological data acquired at subsequent time step ($t_{k+1}$) given the predicted probability density functions of internal state variables for subsequent time step ($t_{k+1}$); substantially continuously estimating a risk that the patient is suffering a specific adverse medical condition, by: generating, using Bayes theorem operating on (a) the conditional likelihood kernel and (b) predicted probability density functions of internal state variables for subsequent time step ($t_{k+1}$), posterior probability density functions for the plurality of the internal state variables for the subsequent time step ($t_{k+1}$); and generating, for a particular internal state variable and based on the posterior probability density functions for the subsequent time step ($t_{k+1}$), a probability that the particular internal state variable exceeds a corresponding pre-defined threshold for that particular internal state variable; and substantially continuously displaying, on a display device, the risk that the patient is suffering the medical specific condition.

P2. The method of P1, further comprising ascertaining that each sensor of the set of sensors is operably coupled to the patient.

P3. The method of P2, wherein ascertaining that each sensor of the set of sensors is operably coupled to the patient comprises attaching to the patient at least one sensor of the set of sensors.

P4. The method of any of P1-P3 wherein:
- the specific adverse medical condition comprises inadequate oxygen delivery; and the corresponding threshold is mixed venous oxygen saturation at or below a given threshold.

P5. The method of any of P1-P4 wherein: the specific adverse medical condition comprises inadequate ventilation of carbon dioxide; and the corresponding threshold is arterial partial pressure of carbon dioxide ($PaCO_2$) at or above a given threshold.

P6. The method of any of P1-P5 wherein: the specific adverse medical condition comprises acidosis; and the corresponding threshold is a blood pH below a given threshold.

P7. The method of any of P1-P6 wherein the specific adverse medical condition comprises hyperlactatemia; and the corresponding threshold is a lactate blood level greater than given threshold.

In any of P1-P7, the set of sensors may comprise a plurality of sensors, including without limitation the heart rate sensor, and the pulse oximetry sensor.

P8. A system for risk-based monitoring of a patient, the system comprising: a data reception module configured to receive measurements of internal state variables from sensors operably coupled to the patient; an observation model configured to produce a conditional likelihood kernel comprising conditional probability density functions of the physiological data acquired at subsequent time step ($t_{k+1}$) given the predicted probability density functions of internal state variables for subsequent time step ($t_{k+1}$); an inference engine configured to generate, using Bayes theorem operating on (a) the conditional likelihood kernel and (b) predicted probability density functions of internal state variables for subsequent time step ($t_{k+1}$), posterior probability density functions for the plurality of the internal state variables for the subsequent time step ($t_{k+1}$); a clinical trajectory interpreter module configured to generate, for a particular internal state variable and based on the posterior probability density functions for the subsequent time step ($t_{k+1}$), a probability that the particular internal state variable exceeds a corresponding pre-defined threshold for that particular internal state variable; and a user interaction module configured to display, on a display device, the risk that the patient is suffering the medical specific condition.

P9. The system of P8 wherein: the specific adverse medical condition comprises inadequate oxygen delivery; and the corresponding threshold is mixed venous oxygen saturation at or below a given threshold.

P10. The system of any of P8-P9 wherein: the specific adverse medical condition comprises inadequate ventilation of carbon dioxide; and the corresponding threshold is arterial partial pressure of carbon dioxide ($PaCO_2$) at or above a given threshold.

P11. The system of any of P8-P10, wherein the set of sensors further includes a respiratory rate sensor, and the measurements of internal state variables includes respiratory rate from the respiratory rate sensor.

P12. The method of any of P8-P11 wherein:
- the specific adverse medical condition comprises acidosis; and the corresponding threshold is a blood pH below a given threshold.

P13. The system of any of P8-P12, wherein the set of sensors further includes a respiratory rate sensor, and the measurements of internal state variables includes respiratory rate from the respiratory rate sensor.

P14. The method of any of P8-P13 wherein: the specific adverse medical condition comprises hyperlactatemia; and the corresponding threshold is a lactate blood level greater than given threshold.

In any of P8-P14, the set of sensors may comprise a plurality of sensors, including without limitation the heart rate sensor, and the pulse oximetry sensor.

P15. A non-transient computer program product comprising executable code, which executable code, when executed by a computer processor, causes the computer processor to implement a method of risk-based monitoring of a patient, the method comprising: receiving, from a set of sensors each operably coupled to the patient, measurements of a corresponding internal state variables of the patient, the set of sensors including at least one of: (i) a heart rate sensor, and (ii) a pulse oximetry sensor; generating predicted probability density functions of internal state variables for a subsequent time step ($t_{k+1}$), wherein the predicted probability density functions are calculated using posterior estimated probability density functions from a preceding time step ($t_k$); generating a conditional likelihood kernel for the subsequent time step ($t_{k+1}$), the conditional likelihood kernel comprising conditional probability density functions of the internal state variables, based on the measurements of the corresponding internal state variables of the patient acquired at subsequent time step ($t_{k+1}$) and the predicted probability density functions of internal state variables for subsequent time step ($t_{k+1}$); substantially continuously estimating a risk that the patient is suffering a specific adverse medical condition, by: generating, using Bayes theorem operating on (a) the conditional likelihood kernel and (b) predicted probability density functions of internal state variables for subsequent time step ($t_{k+1}$), posterior probability density functions for the plurality of the internal state variables for the subsequent time step ($t_{k+1}$); and generating, for a hidden internal state variable and based on the posterior probability density functions for the subsequent time step ($t_{k+1}$), a probability that the hidden internal state variable exceeds a corresponding pre-defined threshold for that particular hidden internal state variable, the probability defining a risk that the patient is suffering the adverse medical specific condition; and substantially continuously displaying, on a display device, the risk that the patient is suffering the adverse medical specific condition.

P16. The computer program product of P15, wherein: the specific adverse medical condition comprises inadequate oxygen delivery; and the corresponding threshold is mixed venous oxygen saturation at or below a given threshold.

P17. The computer program product of any of P15-P16, wherein: the specific adverse medical condition comprises inadequate ventilation of carbon dioxide; and the corresponding threshold is arterial partial pressure of carbon dioxide (PaCO2) at or above a given threshold.

P18. The system of any of P15-P17, wherein the set of sensors further includes a respiratory rate sensor, and the measurements of internal state variables includes respiratory rate from the respiratory rate sensor.

P19. The computer program product of any of P15-P18, wherein: the specific adverse medical condition comprises acidosis; and the corresponding threshold is a blood pH below a given threshold.

P20. The computer program product of any of P15-P19, wherein: the specific adverse medical condition comprises hyperlactatemia; and the corresponding threshold is a lactate blood level greater than given threshold.

In any of P15-P20, the set of sensors may comprise a plurality of sensors, including without limitation the heart rate sensor, and the pulse oximetry sensor.

In any of P1-P20, a particular internal state variable, and a hidden internal state variable, may include without limitation any of the following: inadequate oxygen delivery; inadequate ventilation of carbon dioxide; acidosis; and/or hyperlactatemia.

Various embodiments of this disclosure may be implemented at least in part in any conventional computer programming language. For example, some embodiments may be implemented in a procedural programming language (e.g., "C"), or in an object-oriented programming language (e.g., "C++"), or in Python, R, Java, LISP or Prolog. Other embodiments of this disclosure may be implemented as preprogrammed hardware elements (e.g., application specific integrated circuits, FPGAs, and digital signal processors), or other related components.

In an alternative embodiment, the disclosed apparatus and methods may be implemented as a computer program product for use with a computer system. Such implementation may include a series of computer instructions fixed either on a tangible medium, such as a non-transient computer readable medium (e.g., a diskette, CD-ROM, ROM, FLASH memory, or fixed disk). The series of computer instructions can embody all or part of the functionality previously described herein with respect to the system.

Those skilled in the art should appreciate that such computer instructions can be written in a number of programming languages for use with many computer architectures or operating systems. Furthermore, such instructions may be stored in any memory device, such as semiconductor, magnetic, optical or other memory devices, and may be transmitted using any communications technology, such as optical, infrared, microwave, or other transmission technologies.

Among other ways, such a computer program product may be distributed as a removable medium with accompanying printed or electronic documentation (e.g., shrink wrapped software), preloaded with a computer system (e.g., on system ROM or fixed disk), or distributed from a server or electronic bulletin board over the network (e.g., the Internet or World Wide Web). Of course, some embodiments of this disclosure may be implemented as a combination of both software (e.g., a computer program product) and hardware. Still other embodiments of this disclosure are implemented as entirely hardware, or entirely software.

Computer program logic implementing all or part of the functionality previously described herein may be executed at different times on a single processor (e.g., concurrently) or may be executed at the same or different times on multiple processors and may run under a single operating system process/thread or under different operating system processes/threads. Thus, the term "computer process" refers generally to the execution of a set of computer program instructions regardless of whether different computer processes are executed on the same or different processors and regardless of whether different computer processes run under the same operating system process/thread or different operating system processes/threads.

The embodiments described above are intended to be merely exemplary; numerous variations and modifications will be apparent to those skilled in the art. All such variations and modifications are intended to be within the scope of the present disclosure as defined in any appended claims.

Various examples and embodiments consistent with the present disclosure have be described in detailed above. It is to be understood that these examples and embodiments of the present disclosure are provided for exemplary and illustrative purposes only. Various modifications and changes may be made to the disclosed embodiments by persons skilled in the art without departing from the scope of the present disclosure as defined in the appended claims.

What is claimed is:

1. A computer-based method of risk-based monitoring of a patient, the method comprising:

generating, by the computer, predicted probability density functions of internal state variables for a subsequent time step ($t_{k+1}$), wherein the predicted probability density functions are calculated using posterior estimated probability density functions from a preceding time step ($t_k$);

acquiring, by the computer at subsequent time step ($t_{k+1}$), physiological data from a set of sensors connected with the patient;

generating a conditional likelihood kernel for the subsequent time step ($t_{k+1}$), the conditional likelihood kernel comprising conditional probability density functions of the physiological data acquired at subsequent time step ($t_{k+1}$) given the predicted probability density functions of internal state variables for subsequent time step ($t_{k+1}$);

continuously estimating a risk that a particular bio-marker of the patient is abnormal, wherein the particular bio-marker comprises a hidden internal state variable, because it exceeds, by being either above or below, a corresponding pre-defined clinically significant value for that bio-marker, by:

generating, using Bayes theorem operating on (a) the conditional likelihood kernel and (b) predicted probability density functions of internal state variables for subsequent time step ($t_{k+1}$), posterior probability density functions for the plurality of the internal state variables for the subsequent time step ($t_{k+1}$); and generating, for the particular bio-marker and based on the posterior probability density functions for the subsequent time step ($t_{k+1}$), a probability that the particular bio-marker exceeds the corresponding pre-defined threshold for that particular bio-marker; and generating, for display on a display device, a graphical depiction of the risk that the bio-marker is abnormal.

2. The method of claim 1, wherein the hidden internal state variable is not measured directly.

3. The method of claim 1 wherein:

the set of sensors includes (i) a heart rate sensor, and (ii) a pulse oximetry sensor;

the physiological data comprises heart rate from the heart rate sensor, and oxygen level from the pulse oximetry sensor;

the particular bio-marker comprises mixed venous oxygen saturation; and the corresponding threshold is mixed venous oxygen saturation at or below a level indicating a patient state of inadequate oxygen delivery.

4. The method of claim 1 wherein:

the set of sensors includes (i) a heart rate sensor, and (ii) a pulse oximetry sensor, and (iii) a respiratory rate sensor;

the physiological data comprises heart rate from the heart rate sensor, oxygen level from the pulse oximetry sensor, and respiratory rate from the respiratory rate sensor;

the particular bio-marker comprises arterial partial pressure of carbon dioxide blood; and the corresponding threshold is arterial partial pressure of carbon dioxide at or above a level indicating a patient state of inadequate ventilation of carbon dioxide.

5. The method of claim 1 wherein:

the set of sensors includes (i) a heart rate sensor, and (ii) a pulse oximetry sensor, and (iii) a respiratory rate sensor;

the physiological data comprises heart rate from the heart rate sensor, oxygen level from the pulse oximetry sensor, and respiratory rate from the respiratory rate sensor;

the particular bio-marker comprises blood pH; and the corresponding threshold is a blood pH below a level indicating a patient state of acidosis.

6. The method of claim 1 wherein:

the set of sensors includes (i) a heart rate sensor, and (ii) a pulse oximetry sensor;

the physiological data comprises heart rate from the heart rate sensor, and oxygen level from the pulse oximetry sensor;

the particular bio-marker comprises arterial lactate level; and the corresponding threshold is an arterial lactate blood level greater than a level indicating a patient state of hyperlactatemia.

7. A system for risk-based monitoring of a patient, the system comprising:

a data reception module configured to receive measurements of internal state variables from a set of sensors operably coupled to the patient;

an observation model configured to produce a conditional likelihood kernel comprising conditional probability density functions of the physiological data acquired at subsequent time step ($t_{k+1}$) given the predicted probability density functions of internal state variables for subsequent time step ($t_{k+1}$), the predicted probability density functions calculated using posterior estimated probability density functions from a preceding time step ($t_k$);

an inference engine configured to generate, using Bayes theorem operating on (a) the conditional likelihood kernel and (b) predicted probability density functions of internal state variables for subsequent time step ($t_{k+1}$), posterior probability density functions for the plurality of the internal state variables for the subsequent time step ($t_{k+1}$);

a clinical trajectory interpreter module configured to generate, for a particular bio-marker that is a hidden internal state variable, and based on the posterior probability density functions for the subsequent time step ($t_{k+1}$), a probability that the particular bio-marker is abnormal by exceeding a corresponding pre-defined threshold comprising a clinically significant value for that bio-marker, wherein said probability may exceed said threshold being either above or below said corresponding pre-defined clinically significant value for that bio-marker; and a user interaction module configured to generate, for display on a display device, the risk that the bio-marker is abnormal.

8. The system of claim 7 wherein:

the sensors include (i) a heart rate sensor, and (ii) a pulse oximetry sensor;

the physiological data comprises heart rate from the heart rate sensor, and oxygen level from the pulse oximetry sensor;

the particular bio-marker comprises mixed venous oxygen saturation, which is the hidden internal state variable; and the corresponding threshold is mixed venous oxygen saturation at or below a given threshold, indicating a patient state of inadequate oxygen delivery.

9. The system of claim 7 wherein:

the set of sensors includes (i) a heart rate sensor, and (ii) a pulse oximetry sensor, and (iii) a respiratory rate sensor;

the physiological data comprises heart rate from the heart rate sensor, oxygen level from the pulse oximetry sensor, and respiratory rate from the respiratory rate sensor;

the particular bio-marker comprises arterial partial pressure of carbon dioxide, which is the hidden internal state variable; and the particular bio-marker comprises arterial partial pressure of carbon dioxide (PaCO2) at or above a level indicating a patient state of inadequate ventilation of carbon dioxide.

10. The system of claim 7 wherein:

the set of sensors includes (i) a heart rate sensor, and (ii) a pulse oximetry sensor, and (iii) a respiratory rate sensor;

the physiological data comprises heart rate from the heart rate sensor, oxygen level from the pulse oximetry sensor, and respiratory rate from the respiratory rate sensor;

the particular bio-marker comprises blood pH, which is the hidden internal state variable; and the corresponding threshold is a blood pH below a level indicating a patient state of acidosis.

11. The system of claim 7 wherein:

the sensors include (i) a heart rate sensor, and (ii) a pulse oximetry sensor;

the physiological data comprises heart rate from the heart rate sensor, and oxygen level from the pulse oximetry sensor;

the particular bio-marker comprises arterial lactate level, which is the hidden internal state variable; and the corresponding threshold is an arterial lactate blood level greater than a level indicating a patient state of hyperlactatemia.

12. The system of claim 7, wherein the hidden internal state variable is not measured directly.

13. A non-transient computer program product comprising executable code, which executable code, when executed by a computer processor, causes the computer processor to implement a method of risk-based monitoring of a patient, the method comprising:

generating, by the computer, predicted probability density functions of internal state variables for a subsequent time step ($t_{k+1}$), wherein the predicted probability density functions are calculated using posterior estimated probability density functions from a preceding time step ($t_k$);

receiving, at the computer at subsequent time step ($t_{k+1}$), physiological data from the set of sensors connected with the patient;

generating a conditional likelihood kernel for the subsequent time step ($t_{k+1}$), the conditional likelihood kernel comprising conditional probability density functions of the physiological data acquired at subsequent time step ($t_{k+1}$) given the predicted probability density functions of internal state variables for subsequent time step ($t_{k+1}$);

continuously estimating a risk that a particular bio-marker of the patient is abnormal by being either above or below a corresponding pre-defined clinically significant value for that bio-marker, indicating that the patient is suffering a specific adverse medical condition, by:

generating, using Bayes theorem operating on (a) the conditional likelihood kernel and (b) predicted probability density functions of internal state variables for subsequent time step ($t_{k+1}$), posterior probability density functions for the plurality of the internal state variables for the subsequent time step ($t_{k+1}$); and generating, for the for a particular bio-marker internal state variable, which is a hidden internal state variable, and based on the posterior probability density functions for the subsequent time step ($t_{k+1}$), a probability that the particular bio-marker internal state variable exceeds the corresponding pre-defined threshold for that particular internal state variable bio-marker; and generating, for display, on a display device, a graphical depiction of the risk that the patient is suffering the specific adverse medical condition.

14. The computer program product of claim 13, wherein the particular bio-marker comprises a hidden internal state variable, which hidden internal state variable is not measured directly.

15. The computer program product of claim 14, wherein:

the set of sensors includes (i) a heart rate sensor, and (ii) a pulse oximetry sensor;

the physiological data comprises heart rate from the heart rate sensor and oxygen level from the pulse oximetry sensor;

the particular bio-marker comprises mixed venous oxygen saturation; and the corresponding threshold is mixed venous oxygen saturation at or below a level indicating a patient state of inadequate oxygen delivery.

16. The computer program product of claim 14, wherein:

the set of sensors includes (i) a heart rate sensor, and (ii) a pulse oximetry sensor and (iii) a respiratory rate sensor;

the physiological data comprises heart rate from the heart rate sensor, oxygen level from the pulse oximetry sensor, and respiratory rate from the respiratory rate sensor;

the particular bio-marker comprises arterial partial pressure of carbon dioxide blood; and the corresponding threshold is arterial partial pressure of carbon dioxide at or above a level indicating a patient state of inadequate ventilation of carbon dioxide.

17. The computer program product of claim 14, wherein:

the set of sensor includes (i) a heart rate sensor, and (ii) a pulse oximetry sensor and (iii) a respiratory rate sensor;

the physiological data comprises heart rate from the heart rate sensor, oxygen level from the pulse oximetry sensor, and respiratory rate from the respiratory rate sensor;

the particular bio-marker comprises blood pH; and the corresponding threshold is a blood pH below a level indicating a patient state of acidosis.

18. The computer program product of claim 15, wherein:

the set of sensor includes (i) a heart rate sensor, and (ii) a pulse oximetry sensor;

the physiological data comprises heart rate from the heart rate sensor and oxygen level from the pulse oximetry sensor;

the particular bio-marker comprises arterial lactate level; and the corresponding threshold is an arterial lactate blood level greater than a level indicating a patient state of hyperlactatemia.

* * * * *